(12) United States Patent
Pellegrino et al.

(10) Patent No.: US 11,737,814 B2
(45) Date of Patent: Aug. 29, 2023

(54) CRYOTHERAPY TREATMENT FOR BACK PAIN

(71) Applicant: Relievant Medsystems, Inc., Minneapolis, MN (US)

(72) Inventors: Richard Pellegrino, Leesburg, VA (US); Paula Papineau, West Bridgewater, MA (US); John S. Crombie, East Hanover, NJ (US); Samit Patel, Palo Alto, CA (US); Thomas Ryan, Austin, TX (US)

(73) Assignee: Relievant Medsystems, Inc., Edina, MN (US)

( * ) Notice: Subject to any disclaimer, the term of this patent is extended or adjusted under 35 U.S.C. 154(b) by 535 days.

(21) Appl. No.: 16/818,092

(22) Filed: Mar. 13, 2020

(65) Prior Publication Data

US 2020/0281646 A1 Sep. 10, 2020

Related U.S. Application Data

(63) Continuation of application No. 16/153,242, filed on Oct. 5, 2018, now Pat. No. 10,588,691, which is a
(Continued)

(51) Int. Cl.
*A61B 18/02* (2006.01)
*A61B 18/14* (2006.01)
(Continued)

(52) U.S. Cl.
CPC ...... *A61B 18/1487* (2013.01); *A61B 17/3472* (2013.01); *A61B 18/148* (2013.01);
(Continued)

(58) Field of Classification Search
CPC .............. A61B 18/1487; A61B 18/148; A61B 18/1492; A61B 18/02; A61B 18/0218;
(Continued)

(56) References Cited

U.S. PATENT DOCUMENTS 3,054,881 A 9/1962 Metz et al.
3,062,876 A 11/1962 Pons, Jr. et al.
(Continued)

FOREIGN PATENT DOCUMENTS

AU 2012244378 B2 5/2015
EP 0040658 12/1981
(Continued)

OTHER PUBLICATIONS

A Novel Approach for Treating Chronic Lower Back Pain, Abstract for Presentation at North American Spine Society 26th Annual Meeting in Chicago, IL on Nov. 4, 2011.
(Continued)

*Primary Examiner* — Thomas A Giuliani
(74) *Attorney, Agent, or Firm* — Knobbe, Martens, Olson & Bear, LLP

(57) ABSTRACT

Methods and systems for modulating intraosseous nerves (e.g., nerves within bone) are provided. For example, the methods and systems described herein may be used to modulate (e.g., denervate, ablate) basivertebral nerves within vertebrae. The modulation of the basivertebral nerves may facilitate treatment of chronic back pain. The modulation may be performed by a neuromodulation device (e.g., an energy delivery device).

20 Claims, 55 Drawing Sheets

Related U.S. Application Data continuation of application No. 15/344,284, filed on Nov. 4, 2016, now Pat. No. 10,111,704, which is a continuation of application No. 14/673,172, filed on Mar. 30, 2015, now Pat. No. 9,486,279, which is a continuation of application No. 13/923,798, filed on Jun. 21, 2013, now Pat. No. 8,992,523, which is a continuation of application No. 13/615,300, filed on Sep. 13, 2012, now abandoned, which is a continuation of application No. 13/612,541, filed on Sep. 12, 2012, now Pat. No. 8,361,067.

(51) Int. Cl.
| | |
|---|---|
| *A61B 17/34* | (2006.01) |
| *A61N 5/00* | (2006.01) |
| *A61B 18/18* | (2006.01) |
| *A61B 90/00* | (2016.01) |
| *A61B 34/30* | (2016.01) |
| *A61B 18/20* | (2006.01) |
| *A61B 18/12* | (2006.01) |
| *A61B 18/00* | (2006.01) |
| *A61B 17/00* | (2006.01) |
| *A61B 18/22* | (2006.01) |
| *A61B 18/16* | (2006.01) |
| *A61B 17/88* | (2006.01) |
| *A61B 17/32* | (2006.01) |
| *A61B 18/08* | (2006.01) |
| *A61N 1/05* | (2006.01) |
| *A61N 7/00* | (2006.01) |

(52) U.S. Cl.
CPC .......... *A61B 18/1492* (2013.01); *A61B 18/18* (2013.01); *A61N 5/00* (2013.01); *A61B 17/320068* (2013.01); *A61B 17/8805* (2013.01); *A61B 17/8819* (2013.01); *A61B 18/02* (2013.01); *A61B 18/082* (2013.01); *A61B 18/1206* (2013.01); *A61B 18/16* (2013.01); *A61B 18/1815* (2013.01); *A61B 18/20* (2013.01); *A61B 18/22* (2013.01); *A61B 2017/00261* (2013.01); *A61B 2017/00331* (2013.01); *A61B 2017/00867* (2013.01); *A61B 2018/00017* (2013.01); *A61B 2018/0044* (2013.01); *A61B 2018/0072* (2013.01); *A61B 2018/00339* (2013.01); *A61B 2018/00434* (2013.01); *A61B 2018/00565* (2013.01); *A61B 2018/00577* (2013.01); *A61B 2018/00589* (2013.01); *A61B 2018/00642* (2013.01); *A61B 2018/00761* (2013.01); *A61B 2018/00791* (2013.01); *A61B 2018/00821* (2013.01); *A61B 2018/126* (2013.01); *A61B 2018/1425* (2013.01); *A61B 2018/1807* (2013.01); *A61B 2018/2005* (2013.01); *A61B 2034/301* (2016.02); *A61B 2090/374* (2016.02); *A61B 2218/002* (2013.01); *A61N 1/0551* (2013.01); *A61N 7/00* (2013.01)

(58) Field of Classification Search
CPC .......... A61B 2018/00577; A61B 2018/00583; A61B 2018/00339; A61B 2018/00434; A61B 2018/0044; A61B 2018/00565; A61B 2018/0212; A61B 2018/025; A61B 2018/0256; A61B 2018/0262; A61B 2018/0293; A61B 17/3472; A61B 17/8805; A61B 17/8819; A61B 2017/00261; A61B 2034/301; A61N 1/0551

USPC ....... 606/20–26; 607/96, 104, 105, 107, 113
See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Born |
| 3,997,408 A | 8/1976 | MacKew |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Durate |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shalov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullett |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley et al. |
| 5,147,355 A | 9/1992 | Friedman et al. |
| 5,156,157 A | 10/1992 | Valenta, Jr. et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |

(56) References Cited

U.S. PATENT DOCUMENTS

| | | |
|---|---|---|
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatshahi |
| 5,226,430 A | 7/1993 | Spear et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder et al. |
| 5,282,468 A | 2/1994 | Klepinski |
| 5,292,321 A | 3/1994 | Lee |
| 5,295,484 A | 3/1994 | Marcus et al. |
| 5,300,085 A | 4/1994 | Yock |
| 5,304,214 A | 4/1994 | DeFord et al. |
| 5,305,756 A | 4/1994 | Entrekin et al. |
| 5,314,463 A | 5/1994 | Camps et al. |
| 5,320,617 A | 6/1994 | Leach |
| 5,324,255 A | 6/1994 | Pasafaro et al. |
| 5,325,860 A | 7/1994 | Seward et al. |
| 5,342,292 A | 8/1994 | Nita et al. |
| 5,342,357 A | 8/1994 | Nardella |
| 5,342,409 A | 8/1994 | Mullett |
| 5,344,435 A | 9/1994 | Turner et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Hamm et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,265 A | 12/1994 | Sand |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Millis et al. |
| 5,449,380 A | 9/1995 | Chin |
| 5,454,373 A | 10/1995 | Koger et al. |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Passafaro et al. |
| 5,484,432 A | 1/1996 | Sand |
| 5,486,170 A | 1/1996 | Winston et al. |
| 5,501,703 A | 3/1996 | Holsheimer et al. |
| 5,505,730 A | 4/1996 | Edwarrds |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Fram et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Silwa, Jr. et al. |
| 5,565,005 A | 10/1996 | Erickson et al. |
| 5,569,242 A | 10/1996 | Lax et al. |
| 5,571,088 A | 11/1996 | Lennox et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Chapelon et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holshiemer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Chapelon et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,153 A | 6/1998 | Eggers et al. |
| 5,766,231 A | 6/1998 | Erickson et al. |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swanson |
| 5,807,237 A | 9/1998 | Tindel |
| 5,807,391 A | 9/1998 | Wijkamp |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |

(56) References Cited

U.S. PATENT DOCUMENTS

| | | |
|---|---|---|
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Marcove et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,374 A | 2/2000 | McDaniel |
| 6,030,402 A | 2/2000 | Thompson et al. |
| 6,032,673 A | 3/2000 | Langberg et al. |
| 6,032,674 A | 3/2000 | Eggers et al. |
| 6,033,411 A | 3/2000 | Preissman et al. |
| 6,035,238 A | 3/2000 | Ingle et al. |
| 6,038,480 A | 3/2000 | Hrdlicka et al. |
| 6,045,532 A | 4/2000 | Eggers et al. |
| 6,046,187 A | 4/2000 | Berde et al. |
| 6,047,214 A | 4/2000 | Mueller et al. |
| 6,050,995 A | 4/2000 | Durgin |
| 6,053,172 A | 4/2000 | Hovda et al. |
| 6,053,909 A | 4/2000 | Shadduck |
| 6,056,745 A | 5/2000 | Panescu et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Whayne et al. |
| 6,073,051 A | 6/2000 | Sharkey et al. |
| 6,074,352 A | 6/2000 | Hynynen et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |

(56) References Cited

U.S. PATENT DOCUMENTS

| | | |
|---|---|---|
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,505,075 B1 | 1/2003 | Weiner |
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman, III et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B1 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 | 3/2004 | Heggeness |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |

(56) References Cited

U.S. PATENT DOCUMENTS

| | | |
|---|---|---|
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B1 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckai et al. |
| 7,569,626 B2 | 8/2009 | Truckai |
| 7,574,257 B2 | 8/2009 | Rittman, III |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |
| 7,682,378 B2 | 3/2010 | Truckai et al. |
| 7,708,733 B2 | 5/2010 | Sanders et al. |
| 7,722,620 B2 | 5/2010 | Truckai et al. |
| 7,731,720 B2 | 6/2010 | Sand et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,780,733 B2 | 8/2010 | Carver et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,543 B2 | 2/2011 | Sand et al. |
| 7,892,235 B2 | 2/2011 | Ellis |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Malecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 | 5/2011 | Boucher et al. |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,972,340 B2 | 7/2011 | Sand et al. |
| 8,000,785 B2 | 8/2011 | Rittman, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | McGuckin, Jr. et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara et al. |
| 8,348,946 B2 | 1/2013 | McClurken et al. |
| 8,348,955 B2 | 1/2013 | Truckai et al. |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,430,887 B2 | 4/2013 | Truckai et al. |
| 8,444,636 B2 | 5/2013 | Shadduck et al. |

(56) References Cited

U.S. PATENT DOCUMENTS

| | | |
|---|---|---|
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |
| 8,540,723 B2 | 9/2013 | Shadduck et al. |
| 8,556,910 B2 | 10/2013 | Truckai et al. |
| 8,556,911 B2 | 10/2013 | Mehta et al. |
| 8,560,062 B2 | 10/2013 | Rittman, III et al. |
| 8,562,598 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,088 B2 | 12/2013 | Stern et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |
| 8,747,359 B2 | 6/2014 | Pakter et al. |
| 8,747,398 B2 | 6/2014 | Behnke |
| 8,758,349 B2 | 6/2014 | Germain et al. |
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |
| 8,814,873 B2 | 8/2014 | Schaller et al. |
| 8,818,503 B2 | 8/2014 | Rittman, III |
| 8,821,488 B2 | 9/2014 | Stewart et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,882,755 B2 | 11/2014 | Leung et al. |
| 8,882,759 B2 | 11/2014 | Manley et al. |
| 8,882,764 B2 | 11/2014 | Pellegrino et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,968,288 B2 | 3/2015 | Brannan |
| 8,989,859 B2 | 3/2015 | Deem et al. |
| 8,992,522 B2 | 3/2015 | Pellegrino et al. |
| 8,992,523 B2 | 3/2015 | Pellegrino et al. |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schultz et al. |
| 9,113,974 B2 | 8/2015 | Germain |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |

(56) References Cited

U.S. PATENT DOCUMENTS

| | | |
|---|---|---|
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |
| 9,345,537 B2 | 5/2016 | Harrison et al. |
| 9,345,538 B2 | 5/2016 | Deem et al. |
| 9,351,739 B2 | 5/2016 | Mahoney et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Banamou et al. |
| 9,532,828 B2 | 1/2017 | Condie et al. |
| 9,549,772 B2 | 1/2017 | Carl |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,681,889 B1 | 6/2017 | Greenhalgh et al. |
| 9,687,255 B2 | 6/2017 | Sennett et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,844,406 B2 | 12/2017 | Edwards et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,913,675 B2 | 3/2018 | Germain |
| 10,028,753 B2 | 7/2018 | Pellegrino et al. |
| 10,028,784 B2 | 7/2018 | Kramer et al. |
| 10,052,152 B2 | 8/2018 | Tegg et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,245,092 B2 | 4/2019 | Germain |
| 10,265,099 B2 | 4/2019 | Pellegrino et al. |
| 10,272,271 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,327,841 B2 | 6/2019 | Germain |
| 10,357,258 B2 | 7/2019 | Patel et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,524,805 B2 | 1/2020 | Zilberman et al. |
| 10,571,611 B2 | 2/2020 | Koenig, II et al. |
| 10,588,691 B2 | 3/2020 | Pellegrino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,898,254 B2 | 1/2021 | Diederich et al. |
| 10,905,440 B2 | 2/2021 | Pellegrino et al. |
| RE48,460 E | 3/2021 | Pellegrino et al. |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 | 7/2021 | Edidin |
| 11,123,103 B2 | 9/2021 | Donovan et al. |
| 11,160,563 B2 | 11/2021 | Patel et al. |
| 11,207,100 B2 | 12/2021 | Donovan et al. |
| 11,234,764 B1 | 2/2022 | Patel et al. |
| 11,291,502 B2 | 4/2022 | Patel et al. |

(56) References Cited

U.S. PATENT DOCUMENTS

| | | |
|---|---|---|
| 11,426,199 B2 | 8/2022 | Donovan et al. |
| 11,471,171 B2 | 10/2022 | Pellegrino et al. |
| 11,471,210 B2 | 10/2022 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hovda et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1* | 11/2001 | Heggeness ............ A61B 18/148 606/41 |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016583 A1 | 2/2002 | Cragg |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0052600 A1 | 5/2002 | Davison et al. |
| 2002/0068930 A1 | 6/2002 | Tasto et al. |
| 2002/0095144 A1 | 7/2002 | Carl |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1 | 9/2002 | Daniel et al. |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0183758 A1 | 12/2002 | Middleton et al. |
| 2002/0188284 A1 | 12/2002 | To et al. |
| 2002/0188290 A1 | 12/2002 | Sharkey et al. |
| 2002/0193708 A1 | 12/2002 | Thompson et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0040742 A1 | 2/2003 | Underwood et al. |
| 2003/0040743 A1 | 2/2003 | Cosman et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1 | 8/2003 | Hovda et al. |
| 2003/0181963 A1 | 9/2003 | Pellegrino et al. |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |
| 2004/0064136 A1 | 4/2004 | Crombie et al. |
| 2004/0064137 A1 | 4/2004 | Pellegrino et al. |
| 2004/0068242 A1 | 4/2004 | McGuckin, Jr. |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120668 A1 | 6/2004 | Loeb |
| 2004/0120891 A1 | 6/2004 | Hill et al. |
| 2004/0133124 A1 | 7/2004 | Bates et al. |
| 2004/0162559 A1 | 8/2004 | Arramon |
| 2004/0186544 A1 | 9/2004 | King |
| 2004/0193151 A1 | 9/2004 | To et al. |
| 2004/0193152 A1 | 9/2004 | Sutton et al. |
| 2004/0220577 A1 | 11/2004 | Cragg et al. |
| 2004/0225228 A1 | 11/2004 | Ferree |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209610 A1 | 9/2005 | Carrison |
| 2005/0209659 A1 | 9/2005 | Pellegrino et al. |
| 2005/0216018 A1 | 9/2005 | Sennett |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1* | 12/2005 | Janssen ............... A61B 18/1206 606/50 |
| 2006/0004369 A1 | 1/2006 | Patel et al. |
| 2006/0036264 A1 | 2/2006 | Selover et al. |
| 2006/0052743 A1 | 3/2006 | Reynolds |
| 2006/0064101 A1 | 3/2006 | Arramon |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |
| 2006/0276749 A1 | 12/2006 | Selmon et al. |
| 2006/0287649 A1 | 12/2006 | Ormsby et al. |
| 2007/0021803 A1* | 1/2007 | Deem ................ A61N 1/36071 607/46 |
| 2007/0027449 A1 | 2/2007 | Godara et al. |
| 2007/0055316 A1 | 3/2007 | Godara et al. |
| 2007/0066987 A1 | 3/2007 | Scanlan, Jr. et al. |
| 2007/0074719 A1 | 4/2007 | Danek et al. |
| 2007/0118142 A1 | 5/2007 | Krueger et al. |
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |

(56) References Cited

U.S. PATENT DOCUMENTS

| | | |
|---|---|---|
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Leuthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149846 A1 | 6/2009 | Hoey et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0298737 A1 | 11/2010 | Koehler |
| 2010/0298822 A1 | 11/2010 | Behnke |
| 2010/0298832 A1 | 11/2010 | Lau et al. |
| 2010/0305559 A1 | 12/2010 | Brannan et al. |
| 2010/0324506 A1 | 12/2010 | Pellegrino et al. |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0152855 A1 | 6/2011 | Mayse et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0270238 A1* | 11/2011 | Rizq .................. A61B 18/02 606/21 |
| 2011/0276001 A1 | 11/2011 | Schultz et al. |
| 2011/0295245 A1 | 12/2011 | Willyard et al. |
| 2011/0295261 A1 | 12/2011 | Germain |
| 2011/0319765 A1 | 12/2011 | Gertner et al. |
| 2012/0029420 A1 | 2/2012 | Vilims |
| 2012/0116266 A1 | 5/2012 | House et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0143341 A1* | 6/2012 | Zipnick ............ A61B 17/32002 623/17.16 |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226145 A1 | 9/2012 | Chang et al. |
| 2012/0226273 A1 | 9/2012 | Nguyen et al. |
| 2012/0239049 A1 | 9/2012 | Truckai et al. |
| 2012/0239050 A1 | 9/2012 | Linderman |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0103022 A1 | 4/2013 | Sutton et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0324993 A1 | 12/2013 | McCarthy et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0275760 A1 | 9/2014 | Lee et al. |
| 2014/0276713 A1 | 9/2014 | Hoey et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |
| 2014/0330332 A1 | 11/2014 | Danek et al. |
| 2014/0336630 A1 | 11/2014 | Woloszko et al. |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0105701 A1 | 4/2015 | Mayer et al. |

(56) References Cited

U.S. PATENT DOCUMENTS

| | | |
|---|---|---|
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 11/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino et al. |
| 2017/0238943 A1 | 8/2017 | Sennett et al. |
| 2017/0246481 A1 | 8/2017 | Mishelevich |
| 2017/0266419 A1 | 9/2017 | Goshayeshgar |
| 2017/0303983 A1 | 10/2017 | Linderman et al. |
| 2017/0312007 A1 | 11/2017 | Harlev et al. |
| 2017/0333052 A1 | 11/2017 | Ding et al. |
| 2018/0021048 A1 | 1/2018 | Pellegrino et al. |
| 2018/0042656 A1 | 2/2018 | Edidin |
| 2018/0055539 A1 | 3/2018 | Pellegino |
| 2018/0103964 A1 | 4/2018 | Patel et al. |
| 2018/0140245 A1 | 5/2018 | Videman |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2019/0029698 A1 | 1/2019 | Pellegrino et al. |
| 2019/0038296 A1 | 2/2019 | Pellegrino et al. |
| 2019/0038343 A1 | 2/2019 | Sutton et al. |
| 2019/0038344 A1 | 2/2019 | Pellegrino et al. |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0282268 A1 | 9/2019 | Pellegrino et al. |

(56) References Cited

U.S. PATENT DOCUMENTS

| | | |
|---|---|---|
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Aiambeigi et al. |
| 2020/0022709 A1 | 1/2020 | Burger et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0214762 A1 | 7/2020 | Pellegrino et al. |
| 2021/0022814 A1 | 1/2021 | Crawford et al. |
| 2021/0113238 A1 | 4/2021 | Donovan et al. |
| 2021/0113239 A1 | 4/2021 | Donovan et al. |
| 2021/0177502 A1 | 6/2021 | Wright et al. |
| 2021/0361350 A1 | 11/2021 | Pellegrino et al. |
| 2021/0361351 A1 | 11/2021 | Pellegrino et al. |
| 2021/0369323 A1 | 12/2021 | Edidin |
| 2021/0386491 A1 | 12/2021 | Shmayahu et al. |
| 2022/0192702 A1 | 6/2022 | Donovan et al. |
| 2022/0296255 A1 | 9/2022 | Patel et al. |

FOREIGN PATENT DOCUMENTS

| | | |
|---|---|---|
| EP | 0584959 | 3/1994 |
| EP | 0597463 | 5/1994 |
| EP | 0880938 | 12/1998 |
| EP | 1013228 | 6/2000 |
| EP | 1059067 | 12/2000 |
| EP | 1059087 | 12/2000 |
| EP | 1294323 B1 | 4/2007 |
| EP | 1938765 A1 | 7/2008 |
| EP | 1471836 B1 | 4/2010 |
| EP | 2785260 B1 | 8/2015 |
| EP | 2965782 | 1/2016 |
| EP | 2205313 B1 | 11/2016 |
| EP | 3097946 A1 | 11/2016 |
| EP | 2913081 B1 | 1/2017 |
| JP | S53-139791 U | 11/1978 |
| JP | 6-47058 | 2/1994 |
| JP | 10-290806 | 11/1998 |
| JP | 2001-037760 | 2/2001 |
| JP | 2005-169012 | 6/2005 |
| WO | WO96/36289 | 11/1996 |
| WO | WO98/27876 | 7/1998 |
| WO | WO98/34550 | 8/1998 |
| WO | WO99/19025 | 4/1999 |
| WO | WO99/44519 | 9/1999 |
| WO | WO99/48621 | 9/1999 |
| WO | WO00/21448 | 4/2000 |
| WO | WO00/33909 | 6/2000 |
| WO | WO00/49978 | 8/2000 |
| WO | WO00/56237 | 9/2000 |
| WO | WO00/67648 | 11/2000 |
| WO | WO00/67656 | 11/2000 |
| WO | WO01/01877 | 1/2001 |
| WO | WO01/45579 | 6/2001 |
| WO | WO01/57655 | 8/2001 |
| WO | WO02/05699 | 1/2002 |
| WO | WO02/05897 | 1/2002 |
| WO | WO02/28302 | 4/2002 |
| WO | WO2002/026319 | 4/2002 |
| WO | WO02/054941 | 7/2002 |
| WO | WO02/067797 | 9/2002 |
| WO | WO02/096304 | 12/2002 |
| WO | WO2006/044794 | 4/2006 |
| WO | WO2007/001981 | 1/2007 |
| WO | WO2007/008954 | 1/2007 |
| WO | WO07/31264 | 3/2007 |
| WO | WO08/001385 | 1/2008 |
| WO | WO08/008522 | 1/2008 |
| WO | WO 2008/076330 A1 | 6/2008 |
| WO | WO 2008/076357 A1 | 6/2008 |
| WO | WO08/121259 | 10/2008 |
| WO | WO 2008/121259 A2 | 10/2008 |
| WO | WO2008/140519 | 11/2008 |
| WO | WO2008/141104 | 11/2008 |
| WO | WO 2008/144709 A2 | 11/2008 |
| WO | WO2009/042172 | 4/2009 |
| WO | WO2009/076461 | 6/2009 |
| WO | WO 2009/124192 | 10/2009 |
| WO | WO 2009/155319 A1 | 12/2009 |
| WO | WO 2010/036865 | 4/2010 |
| WO | WO 2010/111246 A1 | 9/2010 |
| WO | WO 2010/135606 A1 | 11/2010 |
| WO | WO 2011/041038 A2 | 4/2011 |
| WO | WO2011/157714 | 12/2011 |
| WO | WO 2012/024162 A1 | 2/2012 |
| WO | WO 2012/065753 | 3/2012 |
| WO | WO 2012/074932 A2 | 6/2012 |
| WO | WO 2013/009516 A2 | 1/2013 |
| WO | WO2013/134452 | 9/2013 |
| WO | WO2013/168006 | 11/2013 |
| WO | WO 2013/180947 A1 | 12/2013 |
| WO | WO 2014/004051 A2 | 1/2014 |
| WO | WO 2011/157714 | 9/2016 |

OTHER PUBLICATIONS

Antonacci, M. Darryl et al.; Innervation of the Human Vertebral Body: A Histologic Study; Journal of Spinal Disorder, vol. 11, No. 6, pp. 526-531, 1998 Lippincott Williams & Wilkins, Philadelphia.

Arnoldi, Carl C.; Intraosseous Hypertension—A Possible Cause of Low Back Pain?; Clinical Orthopedics and Related Research, No. 115, Mar.-Apr. 1976.

Bailey, Jeannie F., "Innervation Patterns of PGP 9.5-Positive Nerve Fibers within the Human Lumbar Vertebra, Journal of Anatomy", (2011) 218, pp. 263-270, San Francisco, California.

Becker, Stephan, et al., "Ablation of the basivertebral nerve for treatment of back pain: a clinical study," The Spine Journal, vol. 17, pp. 218-223 (Feb. 2017).

Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.

Bogduk, Nikolai, et al.; Technical Limitations to the efficacy of Radiofrequency Neurotomy for Spinal Pain; Neurosurgery vol. 20, No. 4, 1987.

Bogduk, N., The anatomy of the lumbar intervertebral disc syndrome, Med J. Aust. 1976, vol. 1, No. 23, pp. 878-881.

Choy, Daniel SS.J. et al.; Percutaneous Laser Disc Decompression, A New Therapeutic Modality; SPINE vol. 17, No. 8, 1992.

Cosman, E.R. et al., Theoretical Aspects of Radiofrequency Lesions in the Dorsal Root Entry Zone. Neurosurgery, vol. 1, No. 6, 1984, pp. 945-950.

Deardorff, Dana L. et al.; Ultrasound applicators with internal cooling for interstitial thermal therapy; SPIE vol. 3594, 1999.

Dupuy, D.E. et al. Radiofrequency ablation of spinal tumors: Temperature distribution in the spinal canal AJR, vol. 175, pp. 1263-1266, Nov. 2000.

Dupuy, Damian E.; Radiofrequency Ablation: An Outpatient Percutaneous Treatment; Medicine and Health/Rhode Island vol. 82, No. 6, Jun. 1999.

Deramond, H. et al., Temperature Elevation Caused by Bone Cement Polymerization During Vertebroplasty, Bone, Aug. 1999, p. 17S-21S, vol. 25, No. 2, Supplement.

Diederich, C. J. et al., "IDTT Therapy in Cadaveric Lumbar Spine: Temperature and thermal dose distributions, Thermal Treatment of Tissue: Energy Delivery and Assessment," Thomas P. Ryan, Editor, Proceedings of SPIE vol. 4247:104-108 (2001).

Diederich, Chris J. et al.; Ultrasound Catheters for Circumferential Cardiac Ablation; SPIE vol. 3594 (1999).

Esses, Stephen I. et al.; Intraosseous Vertebral Body Pressures; SPINE vol. 17 No. 6 Supplement 1992.

(56) References Cited

OTHER PUBLICATIONS

FDA Response to 510(k) Submission by Relievant Medsystems, Inc. submitted on Sep. 27, 2007 (date stamped on Oct. 5, 2007) and associated documents.

Fields, AJ et al; "Innervation of pathologies in the lumbar vertebral endplate and intervertebral disc", The Spine Journal: Official Journal of the North American Spine Society, vol. 14(3), pp. 513-521 (2014).

Fras M.D., Christian et al., "Substance P-containing Nerves within the Human Vertebral Body: An Immunohistochemical Study of the Basivertebral Nerve", The Spine Journal 3, 2003, pp. 63-67.

Gehl, J., "Electroporation: theory and methods, perspectives for drug delivery, gene therapy, and research", Acta Physiol. Scand., vol. 177, pp. 437-447 (2003).

Goldberg, S.N. et al., Tissue ablation with radiofrequency: Effect of probe size, gauge, duration, and temperature on lesion volume, Acad. Radiol., vol. 2, pp. 399-404 (1995).

Hanai, Kenji et al.; Simultaneous Measurement of Intraosseous and Cerebrospinal Fluid Pressures in the Lumbar Region; SPINE vol. 10, No. 1, 1985.

Heggeness, Michael H. et al., The Trabecular Anatomy of Thoracolumbar Vertebrae: Implications for Burst Fractures, Journal of Anatomy, 1997, pp. 309-312, vol. 191, Great Britain.

Heggeness, Michael H. et al. Discography Causes End Plate Deflection; SPINE vol. 18, No. 8, pp. 1050-1053, 1993, J.B. Lippincott Company.

Heggeness, M. et al. Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.

Hoopes et al., "Radiofrequency Ablation of The Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.

Houpt, Jonathan C. et al.; Experimental Study of Temperature Distributions and Thermal Transport During Radiofrequency Current Therapy of the Intervertebral Disc; SPINE vol. 21, No. 15, pp. 1808-1813, 1996, Lippincott-Raven Publishers.

Kleinstueck, Frank S. et al.; Acute Biomechanical and Histological Effects of Intradiscal Electrothermal Therapy on Human Lumbar Discs; SPINE vol. 26, No. 20, pp. 2198-2207; 2001, Lippincott Williams & Wilkins, Inc.

Kopecky, Kenyon K. et al. "Side-Exiting Coaxial Needle for Aspiration Biopsy"—AJR—1996; 167, pp. 661-662.

Lehmann, Justus F. et al.; Selective Heating Effects of Ultrasound in Human Beings; Archives of Physical Medicine & Rehabilitation Jun. 1966.

Letcher, Frank S. et al.; The Effect of Radiofrequency Current and Heat on Peripheral Nerve Action Potential in the Cat; U.S. Naval Hospital, Philadelphia, PA. (1968).

Lotz JC, et al.; "The Role of the Vertebral End Plate in Low Back Pain", Global Spine Journal, vol. 3, pp. 153-164 (2013).

Lundskog, Jan; Heat and Bone Tissue-/an experimental investigation of the thermal properties of bone tissue and threshold levels for thermal injury; Scandinavian Journal of Plastic and Reconstructive Surgery Supplemental 9, From the Laboratory of Experimental Biology, Department of anatomy, University of Gothenburg, Gothenburg, Sweden, Goteborg 1972.

Martin, J.B. et al., Vertebroplasty: Clinical Experience and Follow-up Results, Bone, Aug. 1999, pp. 11S-15S, vol. 25, No. 2, Supplement.

Massad, Malek M.D. et al.; Endoscopic Thoracic Sympathectomy: Evaluation of Pulsatile Laser, Non-Pulsatile Laser, and Radiofrequency-Generated Thermocoagulation; Lasers in Surgery and Medicine; 1991; pp. 18-25.

Mehta, Mark et al.; The treatment of chronic back pain; Anaesthesia, 1979, vol. 34, pp. 768-775.

Nau, William H., Ultrasound interstitial thermal therapy (USITT) in the prostate; SPIE vol. 3594, Jan. 1999.

Rashbaum, Ralph F.; Radiofrequency Facet Denervation A Treatment alternative in Refractory Low Back Pain with or without Leg Pain; Orthopedic Clinics of North America—vol. 14, No. 3, Jul. 1983.

Rosenthal, D.I., Seminars in Musculoskeletal Radiology, vol. 1, No. 2., pp. 265-272 (1997).

Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.

Shealy, C. Norman; Percutaneous radiofrequency denervation of spinal facets Treatment for chronic back pain and sciatica; Journal of Neurosurgery/vol. 43/Oct. 1975.

Sherman, Mary S.; The Nerves of Bone, The Journal of Bone and Joint Surgery, Apr. 1963, pp. 522-528, vol. 45-A, No. 3.

Solbiati, L. et al. Hepatic metastases: Percutaneous radio-frequency ablation with cooled-tip electrodes. Interventional Radiology, vol. 205, No. 2, pp. 367-373 (1997).

Stanton, Terry, "Can Nerve Ablation Reduce Chronic Back Pain ?" AAOS Now Jan. 2012.

The AVAmax System—Cardinal Health Special Procedures, Lit. No. 25P0459-01—www.cardinal.com (copyright 2007).

Tillotson, L. et al. Controlled thermal injury of bone: Report of a percutaneous technique using radiofrequency electrode and generator. Investigative Radiology, Nov. 1989, pp. 888-892.

Troussier, B. et al.; Percutaneous Intradiscal Radio-Frequency Thermocoagulation A Cadaveric Study; SPINE vol. 20, No. 15, pp. 1713-1718, 1995, Lippincott-Raven Publishers.

Ullrich, Jr., Peter F., "Lumbar Spinal Fusion Surgery" Jan. 9, 2013, Spine-Health (available via wayback machine Internet archive at http://web.archive.org/web/20130109095419/http://www/spine-health.com/treatment/spinal-fusion/lumbar-spinal-fusion-surgery).

Osteocool™ Pain Management Brochure, Baylis Medical, copyright 2011.

Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.

Rahme et al., The modic vertebral endplate and marrow changes: pathologic significance and relation to low back pain and segmental instability of the lumbar spine. American Journal of Neuroradiology 29.5 (2008): 838-842; http://www.ajnr.org/content/29/5/838.

Macadaeg et al, A prospective single arm study of intraosseous basivertebral nerve ablation for the treatment of chronic low back pain: 12-month results. North American Spine Society Journal; May 27, 2020, 8 pages.

Vadala et al., "Robotic Spine Surgery and Augmented Reality Systems: A State of the Art", Neurospine Epub Mar. 31, 2020; revised: Feb. 22, 2020; accepted: Feb. 24, 2020; retrieved on [Jun. 10, 2022]. Retrieved from the internet URL:https://www.ncbi.nlm.nih.gov/pmc/articles/PMC7136092/pdf/ns-2040060-030.pdf entire document.

* cited by examiner

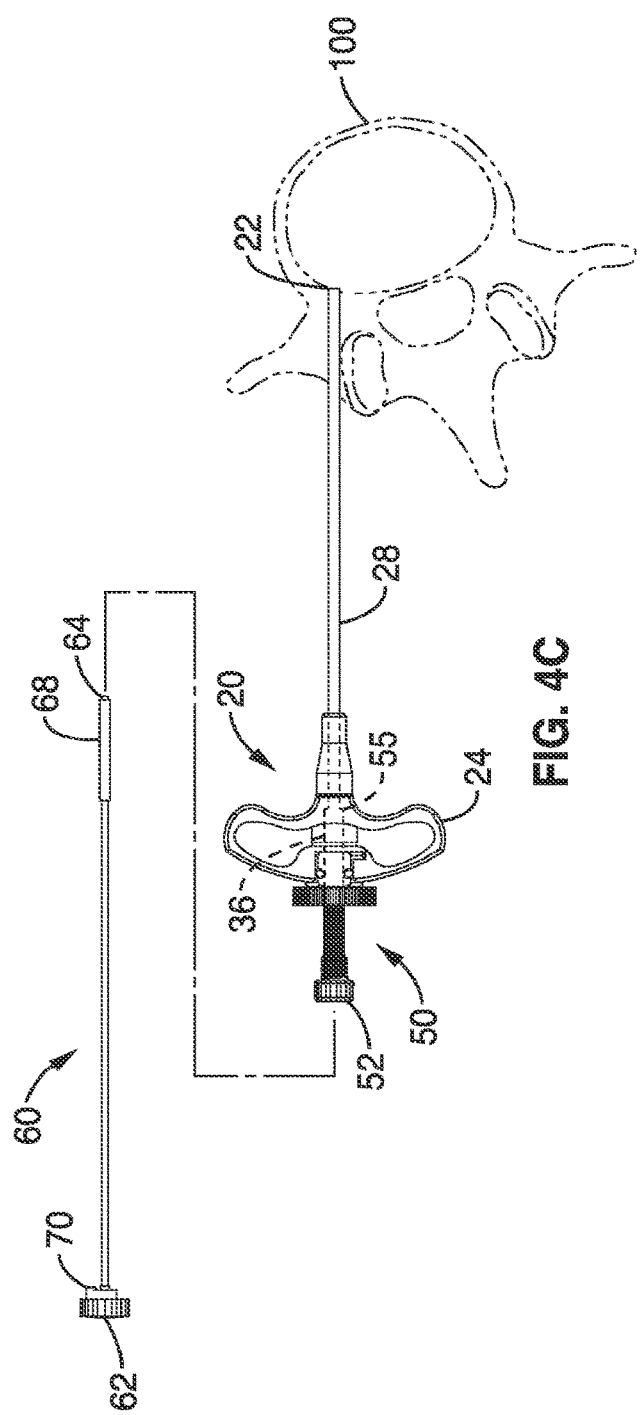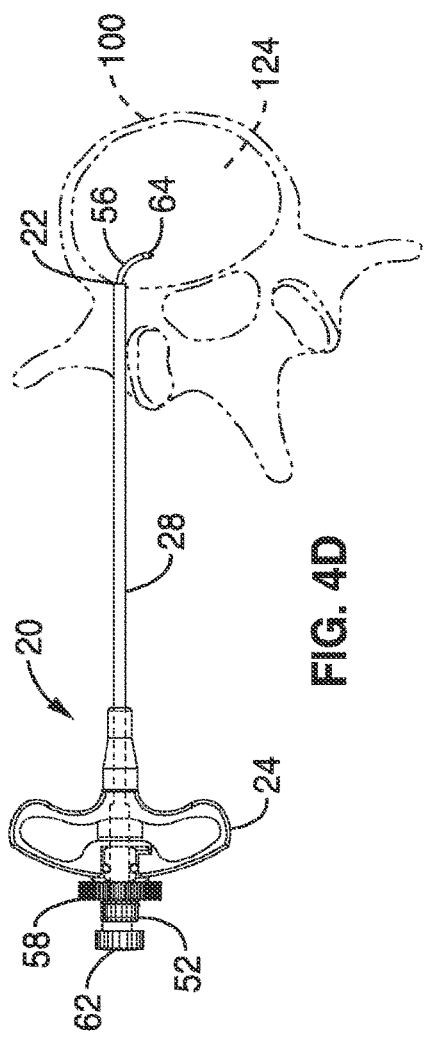
FIG. 4C
FIG. 4D

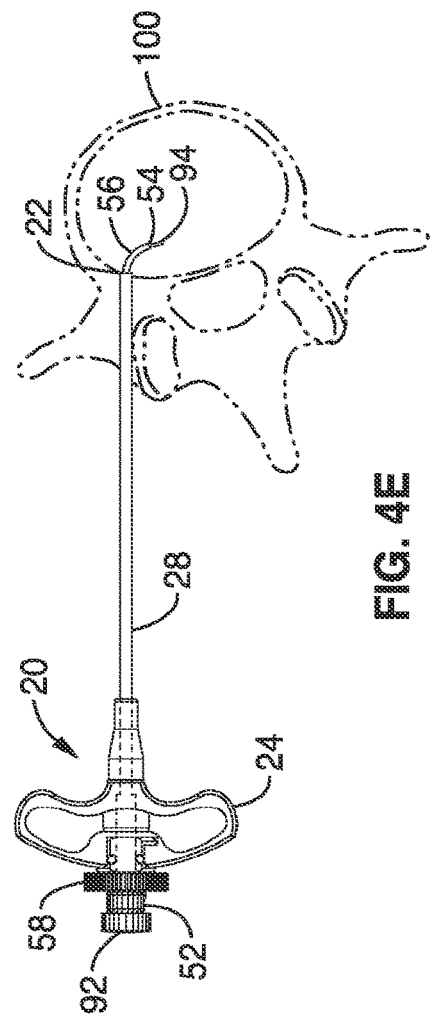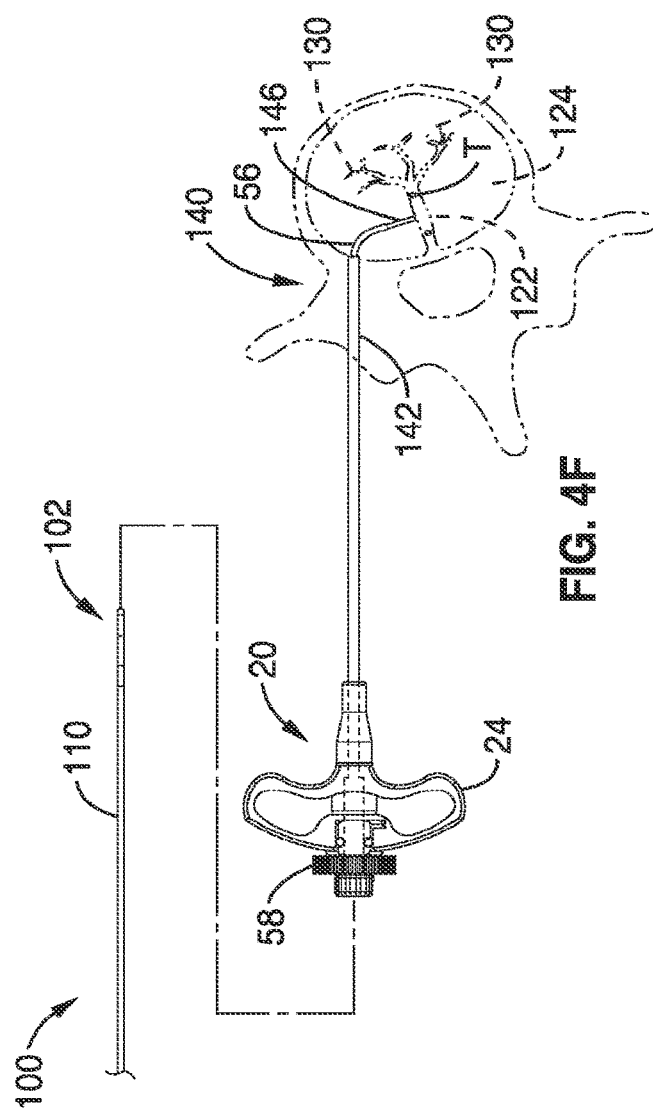

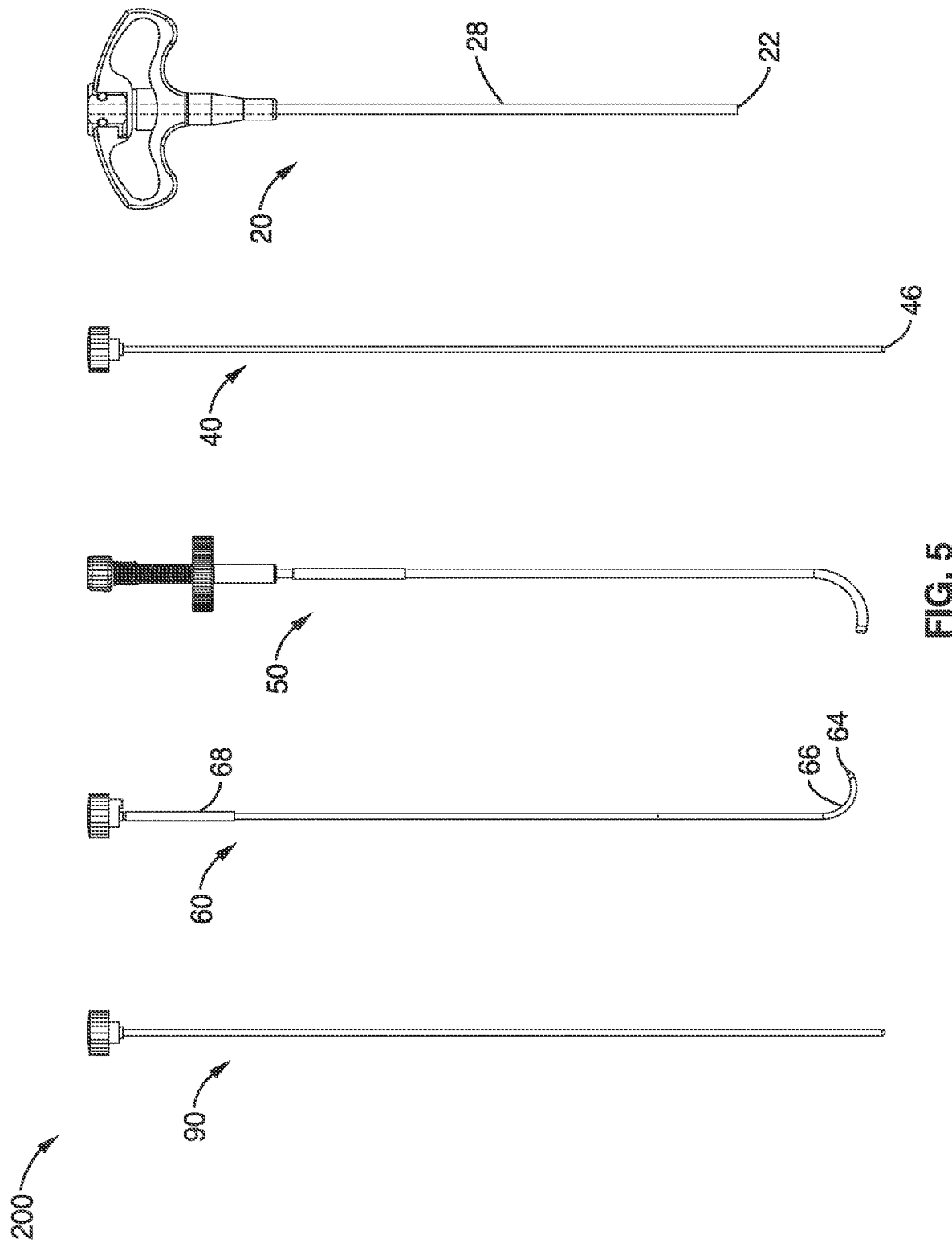

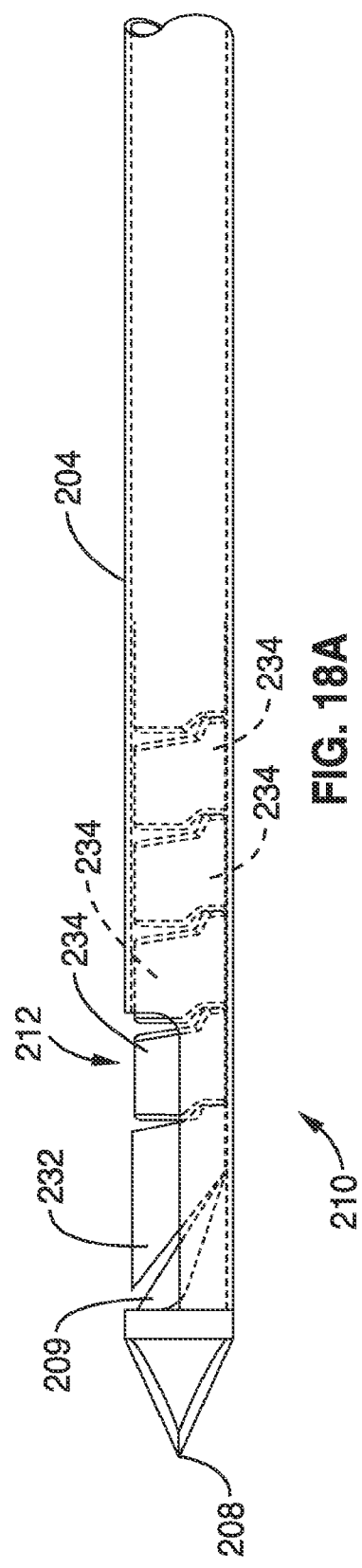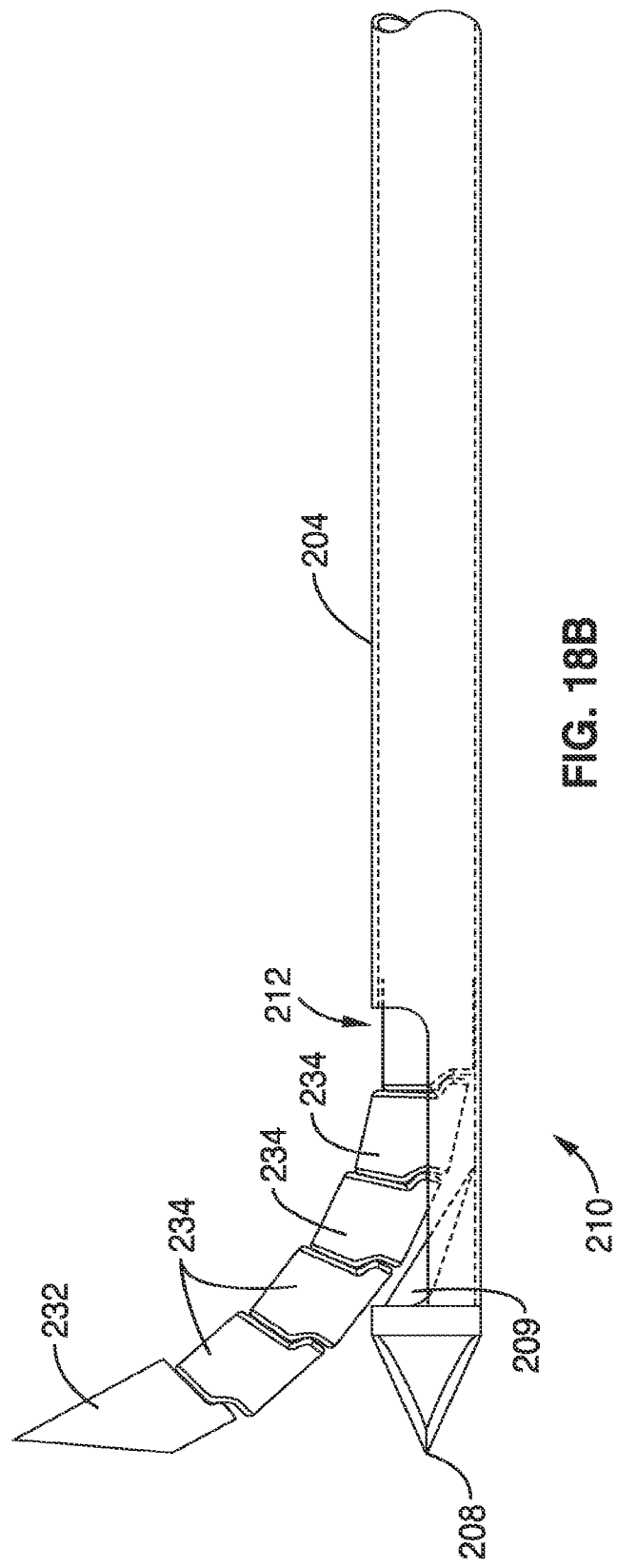

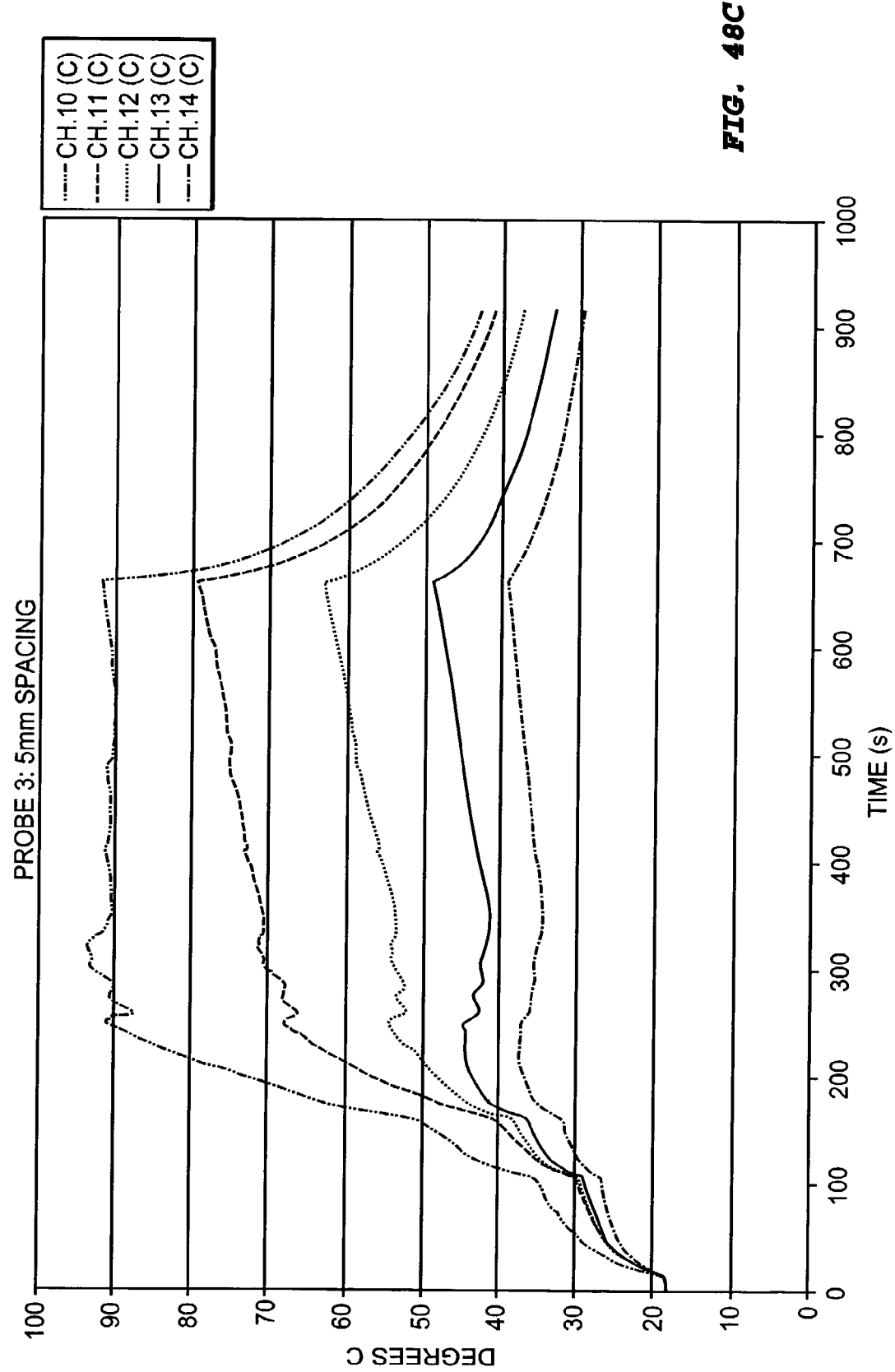

CRYOTHERAPY TREATMENT FOR BACK PAIN

CROSS-REFERENCE TO RELATED APPLICATIONS

This application is a continuation of U.S. application Ser. No. 16/153,242, filed Oct. 5, 2018, now U.S. Pat. No. 10,588,691, which is a continuation of U.S. application Ser. No. 15/344,284, filed Nov. 4, 2016, now U.S. Pat. No. 10,111,704, which is a continuation of U.S. application Ser. No. 14/673,172, filed Mar. 30, 2015, now U.S. Pat. No. 9,486,279, which is a continuation of U.S. application Ser. No. 13/923,798, filed Jun. 21, 2013, now U.S. Pat. No. 8,992,523, which is a continuation of U.S. application Ser. No. 13/615,300, filed Sep. 13, 2012, now abandoned, which is a continuation of U.S. application Ser. No. 13/612,541, filed on Sep. 12, 2012, now U.S. Pat. No. 8,361,067, the content of each of which is incorporated herein by reference in its entirety. The content of each of U.S. application Ser. No. 12/683,555, filed on Jan. 7, 2010, now U.S. Pat. No. 8,613,744; U.S. application Ser. No. 12/566,895, filed on Sep. 25, 2009, now U.S. Pat. No. 8,419,730; and U.S. Provisional Application No. 61/100,553 filed on Sep. 26, 2008; is also incorporated herein by reference in its entirety. While priority is not claimed thereto in the present application, U.S. application Ser. No. 12/683,555 is a continuation-in-part of U.S. application Ser. No. 11/123,766, filed on May 6, 2005, now U.S. Pat. No. 7,749,218, which is a divisional of U.S. application Ser. No. 10/260,879, filed Sep. 30, 2002, now U.S. Pat. No. 6,907,884. While priority is not claimed thereto in the present application, U.S. application Ser. No. 12/683,555 is also a continuation-in-part of U.S. application Ser. No. 12/566,895, filed on Sep. 25, 2009, now U.S. Pat. No. 8,419,730, which claims priority to U.S. Provisional Application No. 61/100,553 filed on Sep. 26, 2008.

FIELD

Various embodiments of the invention pertain generally to generating passageways through tissue and to treatment or monitoring of intraosseous nerves, and more particularly to creating curved paths in bone and to treatment of basivertebral nerves within vertebral bodies of the spine.

BACKGROUND

Back pain is a very common health problem worldwide and is a major cause for work-related disability benefits and compensation. Back pain may arise from strained muscles, ligaments, or tendons in the back and/or structural problems with bones or spinal discs. The back pain may be acute or chronic. Treatments for chronic back pain vary widely and include physical therapy and exercise, chiropractic treatments, rest, pharmacological therapy such as pain relievers or anti-inflammatory medications, and surgical intervention such as vertebral fusion, discectomy or disc repair. Existing treatments can be costly, addictive, temporary, ineffective, and/or can increase the pain or require long recovery times.

SUMMARY

The technique of accessing the vertebral body through minimally invasive means has been developed through the surgical techniques used in vertebroplasty and kyphoplasty. Although accessing the vertebral segments of the spine through the pedicle and into the lateral/anterior section of the body of the vertebra is a primary method of placing a treatment device or neuromodulation device (e.g. a bone cement delivery device, a chemical agent delivery device, and/or an RF probe) into the vertebra, it can be difficult to place a probe in the posterior midline section of the vertebra. Furthermore, accessing the posterior midline section of the S1 segment of the spine can be difficult with a straight linear access route. In several embodiments, a probe or other treatment device (e.g., neuromodulation device) advantageously is capable of navigating to the posterior section of the S1 vertebral segment, as well as to the same target area within a lumbar vertebral segment. In addition, in accordance with several embodiments, vertebral segments in the cervical and thoracic regions of the spine may also be targeted.

In order to accurately and predictably place a treatment device (e.g., neuromodulation device such as an energy or fluid delivery catheter or probe) in the posterior section of a lumbar vertebral body, a sacral vertebral body or other level vertebral body, the device or probe may navigate to the target area through varying densities of bone in some embodiments. However, due to the varying densities of bone, it can be difficult to navigate a probe in bone and ensure its positioning will be in the posterior (e.g., posterior to the midline) or posterior midline section of the vertebral body. Accordingly, several embodiments of the invention are directed to a system and method for generating a path in bone that predictably follows a predetermined curved path. The neuromodulation devices described herein can be configured to perform any of the method steps recited herein.

Several embodiments of the invention are directed to systems and methods to deploy and navigate a flexible treatment instrument, such as a neuromodulation device (e.g., a radiofrequency (RF) bipolar probe, a microwave energy delivery device, a fluid or agent delivery device) within bone. Although the systems and methods described herein are primarily directed to navigating through the bone of a vertebral member of the spine, and particularly to treat the basivertebral nerve (BVN) of a vertebral member, the treatment may be applied to any tissue segment of the body.

Several embodiments of this invention advantageously provide the ability to navigate a curve or angle within varying densities of cancellous bone and create a straight channel at the end of the navigated curve or angle.

In accordance with several embodiments, a method of therapeutically treating a vertebral body having an outer cortical bone region and an inner cancellous bone region, and a BVN having a trunk extending from the outer cortical bone region of the vertebral body into the inner cancellous region of the vertebral body and a plurality of branches extending from the trunk to define a BVN junction or terminus, comprises the steps of: a) inserting one or more energy devices into the vertebral body, and b) exclusively depositing energy within the inner cancellous bone region of the vertebral body between, but exclusive of, the BVN junction and the outer cortical bone region, to denervate the BVN. In some embodiments, the method comprises depositing, or delivering, energy, fluid, or other substance at or proximate (e.g., posterior to) the BVN junction, or terminus. In some embodiments, a delivery probe for delivering a non-energy therapeutic is provided instead of, or in addition to, the energy device.

In some embodiments, a tube-within-tube system comprises a deployable curved tube (e.g. comprised of Nitinol or other flexible, elastic, or shape memory material) that deploys from a straight cannula. The tube can be pre-curved to create an angular range of approximately 0° to approximately 180° (e.g., from approximately 45° to approximately 110°, from approximately 15° to approximately 145°, from approximately 30° to approximately 120°, from approximately 60° to approximately 90°, from approximately 10° to approximately 45°, overlapping ranges thereof, or any angle within the recited ranges), when fully deployed from the straight cannula. The design of the curve can be such that a flexible element (e.g., probe carrying a treatment device) can navigate through the angular range of deployment of the curved tube. The curved tube can allow the flexible element to navigate through a curve within cancellous bone tissue without veering off towards an unintended direction.

Cancellous bone density varies from person to person. Therefore, creating a curved channel within varying density cancellous bone may not predictably or accurately support and contain a treatment device as it tries to navigate the curved channel. With some embodiments, the flexible element is deployed into the bone through the curved tube, which supports the flexible element as it traverses through the curve, thereby preventing the flexible element from channeling its own path. When the flexible element (e.g., energy or agent delivery probe) departs from the tube, it can do so in a linear direction towards the target zone or location. In accordance with several embodiments, this design allows the user to predictably and accurately deploy the flexible element (e.g., treatment device) towards the target zone or location regardless of the density of the cancellous bone.

One embodiment of the invention comprises a system for channeling a path into bone. The system may comprise a trocar having a central channel and opening at its distal tip, and a cannula sized to be received in said central channel and to be delivered to the distal opening. The cannula may comprise a deflectable or deformable tip with a preformed curve such that the tip straightens while being delivered through the trocar and regains its preformed curve upon exiting and extending past the distal opening of the trocar to generate a curved path in the bone corresponding to the preformed curve of the deflectable or deformable tip. At least the distal tip or distal section of the cannula may comprise a resiliently deformable material (such as Nitinol or other shape memory material). The cannula may comprise a central passageway or lumen having an internal diameter configured to allow a treatment device to be delivered through the central passageway to a location beyond the curved path in the bone.

In one embodiment, the system further includes a straight stylet configured to be installed in the trocar, wherein the straight stylet comprises a sharp distal tip that is configured to extend beyond the distal opening of the trocar to pierce the bone as the trocar is being delivered to a treatment location within the bone (e.g., within the inner cancellous bone region of a vertebral body).

The system may further include one or more straightening stylets configured to be introduced in the cannula, wherein the straightening stylet comprises a rigid construction configured to straighten the distal tip of the curved cannula when positioned in the trocar. In some embodiments, the straightening stylet further comprises a sharp distal end to pierce the bone, and the straightening stylet and curved cannula are installed or inserted in the trocar in place of the straight stylet as the trocar is delivered into the bone.

In some embodiments, the system further comprises a curved stylet having an outer radius sized to fit within the central passageway of the curved cannula. The curved stylet is configured to be installed or inserted in the curved cannula while the curved cannula is extended past the distal opening of the trocar, the curved stylet configured to block the distal opening of the curved cannula while being delivered into the bone. In some embodiments, the curved stylet advantageously has a curved distal end corresponding to the curve of the curved cannula.

In one embodiment, the curved stylet has a sharp distal tip configured to extend past the curved cannula to pierce the bone as the cannula is delivered past the distal opening of the trocar. The curved stylet also may advantageously comprise an angled distal tip configured to further support and maintain the curved stylet radius as it is delivered past the distal opening of the trocar and into bone. The curved stylet and the curved cannula may have mating proximal ends (e.g., visual indicia or corresponding physical mating elements) that align the curve of the curved stylet with the curve of the curved cannula.

In one embodiment, the system further includes a straight channeling stylet configured to be installed in the curved cannula after removing the curved stylet, wherein the straight channeling stylet is flexibly deformable to navigate the curved cannula yet retain a straight form upon exiting the curved cannula. The straight channeling stylet may have a length longer than the curved cannula such that it creates a linear path beyond the distal end of the curved cannula when fully extended. Curved and/or straightening stylets may be used for non-spinal embodiments.

In accordance with several embodiments, a method for channeling a path into bone to a treatment location in the body of a patient is provided. The method includes, in one embodiment, inserting a trocar having a central channel and an opening at its distal tip into a region of bone at or near the treatment location, and delivering a cannula through the central channel and to the distal opening. In one embodiment, the cannula comprises a deflectable or deformable tip with a preformed curve such that the tip straightens while being delivered through the trocar and regains its preformed curve upon exiting the trocar, and extending the cannula past the distal opening of the trocar to generate a curved path in the bone corresponding to the preformed curve of the deflectable tip. In some embodiments, a treatment device is delivered through a central passageway or lumen in the cannula to the treatment location beyond the curved path. The treatment device may facilitate or effect energy delivery, fluid delivery, delivery of an agent, etc.

In one embodiment, inserting a trocar into a region of bone comprises inserting a stylet into the trocar such that the stylet extends beyond the distal opening of the trocar, and inserting the stylet and trocar simultaneously into the region of bone such that the stylet pierces the bone as the trocar is being delivered to a treatment location.

In one embodiment, delivering a cannula through the central channel comprises inserting a straightening stylet into the central passageway of the cannula and inserting the straightening stylet and straightened cannula simultaneously into the trocar. In one embodiment, the straightening stylet comprises a rigid construction configured to straighten the curved distal tip of the cannula. In one embodiment, the straightening stylet further comprises a sharp distal end to pierce the bone. In one embodiment, the straightening stylet and cannula are installed simultaneously along with the trocar as the trocar is delivered into the bone.

In one embodiment, extending the cannula past the distal opening is performed by inserting a curved stylet into the central passageway of the curved cannula such that a distal tip of the curved stylet extends to at least the distal opening of the curved cannula and simultaneously extending the curved cannula and curved stylet from the distal end of the trocar such that the curved stylet blocks the distal opening of the curved cannula while being delivered into the bone.

In some embodiments, the curved stylet has a curved distal end corresponding to the curve of the curved cannula such that the curved stylet reinforces the curved shape of the curved cannula as the curved cannula is extended past the distal opening of the trocar. The curved stylet may have a sharp distal tip so that when the curved stylet extends past the distal opening of the curved cannula the curved stylet is configured to pierce the cancellous bone tissue as the curved cannula is delivered past the distal opening of the trocar.

In some embodiments, the curved stylet is then removed from the curved cannula, and a straight channeling stylet is inserted into the curved distal end of the cannula. The straight channeling stylet can be flexibly deformable to navigate the curved cannula, yet retain a straight form upon exiting the curved cannula. The straight channeling stylet can advantageously be longer than the curved cannula to create a linear channel beyond the distal tip of the curved cannula.

In some embodiments, the trocar is inserted through a cortical bone region and into a cancellous bone region of a vertebral body, and the curved cannula is extended though at least a portion of the cancellous bone region to a location at or near a target treatment location. A target treatment location may comprise a BVN within the vertebra, and treatment may be delivered to the target treatment location to modulate (e.g., denervate, ablate, stimulate, block, disrupt) at least a portion of the BVN (e.g., terminus or junction or a portion of the BVN between the terminus or junction and the posterior wall). In one embodiment, a portion of the BVN is modulated by delivering focused, therapeutic heating (e.g., a thermal dose) to an isolated region of the BVN. In another embodiment, a portion of the BVN is modulated by delivering an agent to the treatment region to isolate treatment to that region. In accordance with several embodiments of the invention, the treatment is advantageously focused on a location of the BVN that is upstream of one or more branches of the BVN.

In accordance with several embodiments, a kit for channeling a path into bone is provided. The kit comprises a trocar having a central channel and opening at its distal tip, and a cannula selected from a set of cannulas sized to be received in the central channel and delivered to the distal opening. The cannula has a deflectable or deformable distal tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula comprises a central passageway or lumen having an internal diameter configured to allow a treatment device to be delivered through the central passageway or lumen to a location beyond the curved path within bone, wherein the set of cannulas comprises one or more cannulas that have varying preformed curvatures at the distal tip.

In some embodiments, the one or more cannulas have a varying preformed radius at the distal tip. In addition, the one or more cannulas may each have distal tips that terminate at varying angles with respect to the central channel of the trocar. The length of the distal tips may also be varied. The angle of the distal tip with respect to the central channel of the trocar may vary from 0 degrees to 180 degrees (e.g., from 10 degrees to 60 degrees, from 15 degrees to 45 degrees, from 20 degrees to 80 degrees, from 30 degrees to 90 degrees, from 20 degrees to 120 degrees, from 15 degrees to 150 degrees, overlapping ranges thereof, or any angle between the recited ranges). The kit may further include a straight stylet configured to be installed in the trocar, the straight stylet comprising a sharp distal tip that is configured to extend beyond the distal opening of the trocar to pierce the bone as the trocar is being delivered to a treatment location within the bone. The kits may be adapted for non-spinal embodiments.

In some embodiments, the kit includes a set of curved stylets having an outer radius sized to fit within the central passageway of the curved cannula, wherein each curved stylet is configured to be installed in the curved cannula while the curved cannula is extended past the distal opening of the trocar. The curved stylet may be configured to block the distal opening of the curved cannula while being delivered into the bone. In one embodiment, each curved stylet has a varying curved distal end corresponding to the curve of a matching curved cannula in the set of curved cannulas. The curved stylet may have a sharp distal tip configured to extend past the curved cannula to pierce the bone as the cannula is delivered past the distal opening of the trocar.

In some embodiments, the kit includes a set of straight channeling stylets wherein one of the set of stylets is configured to be installed in the cannula after removing the curved stylet. The straight channeling stylet can be flexibly deformable to navigate the curved cannula yet retain a straight form upon exiting the curve cannula. Each of the straight channeling stylets can have a varying length longer than the curved cannula such that the straight channeling stylet creates a predetermined-length linear path beyond the distal end of the curved cannula when fully extended.

In accordance with several embodiments, a system for channeling a path into bone comprising a trocar with a proximal end, a distal end and a central channel disposed along a central axis of the trocar and extending from the proximal end toward the distal end is provided. The trocar, in one embodiment, comprises a radial opening at or near the distal end of the trocar, the radial opening being in communication with the central channel. The system further comprises, in one embodiment, a curveable or steerable cannula sized to be received in said central channel and delivered from the proximal end toward said radial opening. In several embodiments, the curveable cannula comprises a curveable and/or steerable distal end configured to be extended laterally outward from the radial opening in a curved path extending away from the trocar, and a central passageway having a diameter configured allow a treatment device (e.g., probe, catheter) to be delivered through the central passageway to a location beyond the curved path.

In several embodiments, the curveable cannula comprises a proximal end having a proximal body. In one embodiment, the proximal end of the trocar comprises a housing. The housing may comprise a proximal recess configured to allow reciprocation (e.g., alternating back-and-forth motion or other oscillatory motion) of the proximal body of the curveable cannula. The proximal recess of the housing may be in communication with the central channel of the trocar. In several embodiments, a proximal body of the curveable cannula is configured to be releasably restrained with respect to translation within the trocar housing. In several embodiments, the system comprises a probe sized to fit within the central channel of the cannula. The probe may comprise a proximal end configured to be releasably restrained with respect to translation within the proximal body of the curveable cannula. In one embodiment, the probe comprises mating threads that mate with corresponding mating threads of a distal recess of the drive nut so as to allow controlled translation of the probe with respect to the drive nut.

In several embodiments, a spine therapy system is provided. In one embodiment, the system comprises a trocar having a proximal end, a distal end and a central channel. The central channel can be disposed along a central axis of the trocar and extend from the proximal end toward the distal end. In one embodiment, the trocar comprises a radial opening at or near the distal end of the trocar, the radial opening being in communication with the central channel. In one embodiment, the trocar is configured to be deployed through a cortical bone region and into a cancellous bone region of a vertebral body. In one embodiment, a curveable cannula is configured (e.g., sized) to be received in said central channel and delivered from the proximal end toward the radial opening. The curveable cannula may comprise a central passageway and a curveable and/or steerable distal end configured to be extended laterally outward from the radial opening in a curved path extending away from the trocar. The curved path may be generated through at least a portion of the cancellous bone region of the vertebral body. In one embodiment, a treatment device or probe is configured to be delivered through the central passageway to a location beyond the curved path. The trocar, curveable cannula, and/or treatment device can have a sharp distal end or tip configured to penetrate bone tissue. In some embodiments, the distal ends of the trocar, curveable cannula, and/or treatment device are rounded or blunt. In some embodiments, the distal ends of the trocar or curved or curveable cannula have a full radius on the inside and/or outside diameter to prevent other devices from catching when being pulled back into the distal end after being delivered out of the distal end.

In accordance with several embodiments, a method for channeling a path into bone to a treatment location in the body of a patient is provided. The bone may be within or proximal a vertebral body, or may be non-spinal (e.g., knee or other joints). In one embodiment, the method comprises inserting a trocar into a region of bone near the treatment location. In one embodiment, the trocar comprises a proximal end, a distal end, and a central channel disposed between the two ends. In one embodiment, the method comprises delivering a curveable cannula through the central channel and to a radial opening at or near the distal end of the curveable cannula. In one embodiment, the method comprises deploying the curveable cannula laterally outward from the radial opening in a curved path extending away from the trocar. In one embodiment, the method comprises steering the curveable cannula (e.g., via a pull cord coupled to the distal tip of the curveable cannula or via other steering mechanisms) to bias the curveable cannula in the curved path. Energy and/or another diagnostic or therapeutic agent is then optionally delivered to the treatment location.

In accordance with several embodiments, a method of treating back pain is provided. In some embodiments, the method comprises identifying a vertebral body for treatment (e.g., a target for treatment of chronic back pain). In some embodiments, the method comprises identifying a treatment zone, area or site within the inner cancellous bone region of the vertebral body. In some embodiments, the treatment zone, area or site is within a posterior section of the vertebral body (e.g., posterior to an anterior-posterior midline, within the area between 20% and 50% of the distance from the posterior wall of the vertebral body). In some embodiments, the treatment zone comprises a location corresponding to the mid-height of the vertebra from an anterior-posterior view. In some embodiments, a border of the treatment zone is at least 1 cm (e.g., between 1-2 cm, 2-3 cm, 3-4 cm, or more) from the posterior wall of the vertebral body. In some embodiments, the treatment zone is determined by measuring the distance from the posterior wall to the basivertebral foramen as a percentage of the total distance from the posterior wall to the anterior wall of the vertebral body.

In some embodiments, identifying a treatment zone is performed preoperatively using imaging methods such as magnetic resonance imaging (MRI) or computed tomography (CT) imaging modalities. In some embodiments, the treatment zone, site, or location corresponds to a location that is about mid-height between the superior and inferior endplate surfaces of the vertebral body (which may be identified by imaging methods from an anterior-posterior view). In some embodiments, the treatment zone, site or location is identified by measuring the distance from the posterior wall of the vertebral body to the basivertebral foramen from images (e.g., (e.g., anteroposterior and/or lateral MRI or CT images) of the vertebral body as a percentage of the total distance from the posterior wall to the anterior wall of the vertebral body. In some embodiments, inserting the neuromodulation device within the treatment zone is performed under visualization (e.g., using fluoroscopy). In some embodiments, positioning a distal end portion of the neuromodulation device within the treatment zone comprises positioning the distal end portion (and any active elements such as electrodes located at the distal end portion) at a location corresponding to the measured distance percentage described above. In some embodiments, the percentage is a standardized distance percentage that is not individually measured for the individual subject or vertebral body being treated. In some embodiments, the treatment zone, site, or location corresponds to a location at or proximate (e.g., posterior to) a terminus of the basivertebral foramen.

In some embodiments, the method comprises inserting a curved cannula through the outer cortical bone region of the vertebral body and into the inner cancellous bone region of the vertebral body. The curved cannula can comprise a flexible catheter, tube, or other conduit having a pre-curved or steerable distal end. The curved cannula may comprise Nitinol, PEEK, or other thermoplastic, shape memory or resiliently deformable material. In some embodiments, the method comprises inserting a neuromodulation device within the curved cannula. The neuromodulation device can comprise an energy delivery device, a fluid delivery device, or an agent delivery device. The fluid may or may not comprise an agent, such as a chemical agent. In one embodiment, the chemical agent comprises a lytic agent.

In various embodiments, the energy delivery device is configured to deliver radiofrequency energy, microwave energy, light energy, thermal energy, ultrasonic energy, and/or other forms of electromagnetic energy, and/or combinations of two or more thereof. In accordance with several embodiments, the energy is configured to heat tissue within bone (e.g., a vertebral body) sufficient to modulate (e.g., denervate, ablate) intraosseous nerves (e.g., basivertebral nerves or other nerves located partially or fully within bone). In other embodiments, the energy is configured to treat tissue outside the spine, for example in non-spinal joints or in non-orthopedic applications (e.g., cardiac, pulmonary, renal, or treatment of other organs and/or their surrounding nerves). The temperature of the energy may be in the range of between 40° C. and 100° C., between 50° C. and 95° C., between 60° C. and 80° C., between 75° C. and 95° C., between 80° C. and 90° C., overlapping ranges thereof, or any temperature between the recited ranges. In some embodiments, the temperature and length of treatment can be varied as long as the thermal dose is sufficient to modulate (e.g., at least temporarily denervate, ablate, block, disrupt) the nerve. In some embodiments, the length of treatment (e.g., delivery of energy) ranges from about 5 to about 30 minutes (e.g., about 5 to 15 minutes, about 10 to 20 minutes, about 15 to 25 minutes, about 20 to 30 minutes, overlapping ranges thereof, 15 minutes, or about any other length of time between the recited ranges). In some embodiments, the neuromodulation device comprises a sensor to measure nerve conduction of the nerve at the treatment zone.

The energy delivery device may comprise one or more probes (e.g., a radiofrequency probe). In some embodiments, the probe comprises one or more electrodes configured to generate a current to heat tissue within bone. In one embodiment, the probe comprises a bipolar probe having two electrodes. The two electrodes may comprise an active electrode and a return electrode. In one embodiment, the active electrode comprises a tip electrode positioned at the distal tip of the radiofrequency probe and the return electrode comprises a ring electrode spaced proximally from the active electrode with insulation material between the two electrodes. In one embodiment, the return electrode comprises a tip electrode positioned at the distal tip of the probe (e.g., a radiofrequency probe) and the active electrode comprises a ring electrode spaced proximally from the return electrode. The two electrodes may be spaced about 1 mm, 2 mm, 3 mm, 4 mm, 5 mm, 6 mm, 7 mm, 8 mm, 9 mm or 1 cm apart. In various embodiments, the electrodes comprise cylindrical electrodes, tip electrodes, plate electrodes, curved electrodes, circular electrodes, or other shapes. In some embodiments, the electrodes comprise an electrode array. In various embodiments, the frequency of the energy can be between about 100 kHz and 1 MHz, between 400 kHz and 600 kHz, between 300 kHz and 500 kHz, between 350 kHz and 600 kHz, between 450 kHz and 600 kHz, overlapping ranges thereof, or any frequency within the recited ranges.

In one embodiment, the energy delivery device comprises an ultrasound probe having one or more ultrasound transducers. The ultrasound probe may be configured to deliver high-intensity focused ultrasonic energy, low-intensity ultrasonic energy or other forms of ultrasonic energy sufficient to modulate the nerve. The ultrasound energy may be used for cavitation or non-cavitation. In one embodiment, the energy delivery device comprises a laser or light energy delivery device configured to deliver light energy sufficient to modulate the nerve. In one embodiment, the energy delivery device is configured to deliver radiation sufficient to modulate the nerve. In one embodiment, the energy delivery device comprises a microwave energy delivery device comprising one or more microwave antennas configured to deliver microwave energy sufficient to effect modulation of the nerve.

In one embodiment, a fluid delivery device is used to effect a temperature change in a location in the disc. For example, the fluid delivery device may be used to deliver a cryoablative fluid. In another embodiment, the fluid delivery device may be used to deliver a cooling fluid to cool a region in conjunction with a therapy that generates heat. In some embodiments, a distal portion of the curved cannula is shaped so as to guide a distal end of the neuromodulation device towards the midline of the vertebral body (or other treatment area outside the spine). In some embodiments, a proximal end of the fluid delivery device is coupled to a fluid source or reservoir (e.g., syringe, fluid pump). In some embodiments, the fluid delivery device comprises a catheter, tube, sleeve, needle, cannula, wicking device, or other conduit configured to deliver fluid. The fluid may comprise neurolytic agents, chemotherapy agents, radioactive substances, medications, drugs, pharmaceuticals, alcohols, acids, solvents, cooling agents, nerve blocking agents, and/or other chemical agents.

In some embodiments, the method comprises advancing the distal end of the neuromodulation device out of a distal opening of said cannula and into the inner cancellous bone region of the vertebral body or treatment area. The distal opening may be an axial opening or a radial opening. In some embodiments, the method comprises positioning the distal end of said neuromodulation device within, at or proximate the treatment zone, area site, or location of the vertebral body or treatment area.

In some embodiments, the method comprises effecting modulation of at least a portion of a nerve (e.g., basivertebral nerve or intraosseous nerve) using the neuromodulation device. The modulation (e.g., neuromodulation) can comprise partial or complete and/or temporary or permanent blocking, disruption, denervation or ablation of the nerve. In various embodiments, the modulation comprises radiofrequency ablation, microwave energy ablation, chemical ablation, cryoablation, ultrasonic ablation, laser ablation, thermal ablation, thermal heating, cooling, mechanical severing, neuromodulation, and/or stimulation of the nerve. In one embodiment, stimulation of the nerve is performed to block the travel of signals indicative of pain. Stimulation may comprise mechanical, electrical, or electromechanical stimulation. The stimulation may be continuous or pulsed.

In accordance with several embodiments, a method of treating pain (e.g., back pain) is provided. In some embodiments, the method comprises identifying a treatment zone, such as a vertebral body for treatment (e.g., an identified source of pain or location likely to treat pain). In some embodiments, the treatment zone comprises a basivertebral residence zone within which a portion of the basivertebral nerve (e.g., main trunk, junction, terminus of basivertebral foramen, etc.) is likely to reside. In some embodiments, the treatment zone is identified without knowing the precise location of the basivertebral nerve. In some embodiments, the method comprises identifying a treatment zone, site, region or location within the inner cancellous bone region within a posterior section of the vertebral body. The posterior section may comprise a section posterior to an anterior-posterior midline or a region within a distance between about 10% and about 50%, between about 20% and about 50%, between about 10% and about 40% of the distance from the posterior wall. In some embodiments, the method comprises inserting a distal end portion of the neuromodulation device (e.g., energy and/or fluid delivery probe), and any active elements disposed thereon, within or proximate the treatment zone. In some embodiments, the method comprises thermally inducing modulation of a function of a basivertebral nerve within the vertebral body with the energy delivery probe.

In some embodiments, the method comprises generating a curved path within the inner cancellous bone region towards a midline of the vertebral body with a cannula having a pre-curved distal end portion to facilitate access to the posterior section of the vertebral body. In some embodiments, insertion of the neuromodulation device through a curved cannula allows for access straight through (e.g., concentrically through) the pedicle in a transpedicular approach instead of an off-center access, which may be difficult for some levels of vertebrae due to anatomic constraints. In some embodiments, the method comprises inserting the neuromodulation device within the curved path created by the cannula. In some embodiments, the cannula is shaped so as to guide a distal end portion of the neuromodulation device towards the midline of the vertebral body. In some embodiments, the method comprises inserting a stylet within the cannula that is adapted to penetrate bone tissue of the vertebral body beyond the curved path created by the cannula.

In accordance with several embodiments, a method of therapeutically heating a vertebral body to treat back pain is provided, In some embodiments, the method comprises identifying a residence zone of a basivertebral nerve within the inner cancellous bone region of the vertebral body. In some embodiments, the method comprises inserting two electrodes into the vertebral body. In some embodiments, the method comprises positioning the two electrodes within or proximate the residence zone. In some embodiments, the method comprises generating a heating zone between the two electrodes to heat the basivertebral nerve. For example, a first electrode may be activated to generate a current between the first electrode and a second electrode. The current may generate heat within the bone tissue. The heating zone may comprise an inner resistive heating zone and an outer conductive heating zone. In some embodiments, the heating zone is configured to have a radius or diameter between about 0.5 cm and 2 cm (e.g., 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm). In accordance with several embodiments, forming heating zones (and in some cases, lesions) of a specific size and shape can be improved by adjusting parameters such as diameter and active length of electrodes, initial and steady-state power input, length of treatment, and device control temperature.

In some embodiments, inserting two electrodes into the vertebral body comprises inserting a first energy delivery probe having a first electrode within the inner cancellous bone region and positioning a second energy delivery probe having a second electrode within the inner cancellous bone region. In some embodiments, inserting two electrodes into the vertebral body comprises inserting a single energy delivery probe having two electrodes within the inner cancellous bone region.

In some embodiments, positioning the two electrodes within or proximate the residence zone comprises positioning the electrodes at a location such that a single heating treatment modulates (e.g., denervates, ablates) the entire basivertebral nerve system without requiring separate downstream modulation (e.g., denervation, ablation) treatments. In some embodiments, positioning the two electrodes of within or proximate the residence zone comprises positioning the two electrodes to straddle the residence zone. In some embodiments, positioning the two electrodes within or proximate the residence zone comprises positioning a first electrode on a first side of the vertebral body and positioning a second electrode on a second side of the vertebral body.

In accordance with several embodiments of the invention, methods and systems allow for positioning of a treatment device in contact with or in close proximity to a basivertebral nerve without knowing the precise location of the basivertebral nerve. In attempting to place at least one electrode in close proximity to the BVN, the approaches disclosed in the teachings of the art are somewhat problematic. In particular, although the location of the BVN is somewhat well known, the BVN is radiolucent and so its precise location can not be easily identified by an X-ray. Since the BVN is also extremely thin, knowingly placing the electrode in close proximity to the BVN may be problematic in some cases. Moreover, in one embodiment, since certain RF electrodes appear to heat only a fairly limited volume of bone, misplacement of the electrode vis-à-vis the BVN may result in heating a volume of bone that does not contain the BVN. "Close proximity" with regard to the intraosseous or basivertebral nerve can mean located at a position such that the nerve is modulated upon activation of the neuromodulation device or delivery of fluid or other substances by the neuromodulation device.

For example, and now referring to FIGS. 20 and 21, there is provided a representation of a treatment scheme involving the placement of a conventional bipolar electrode device in close proximity to an intraosseous nerve (ION). In these figures, the ION is represented by the solid line identified as ION, while the vertically-disposed dotted lines identify the edges of the zone within which the practitioner believes the ION likely resides (i.e., the ION residence zone, or "IRZ"). As shown in FIGS. 20 and 21, if the ION is substantially in the center of the ION residence zone, then placement of the bipolar electrode either on the left hand boundary of the ION residence zone (as in FIG. 20) or substantially in the middle of the ION residence zone (as in FIG. 21) satisfactorily locates the electrodes in a region that allows the current flowing from the electrodes to flow across the ION. In several embodiments, since the current flowing across the ION may resistively and conductively heat the local bone tissue and the ION may be heated to therapeutically beneficial temperatures, these scenarios may provide beneficial treatment of the ION.

However, now referring to FIG. 22, if the ION is substantially at the right edge of the ION residence zone, then placement of the bipolar electrodes on the left hand side of the ION residence zone fails to locate the electrodes in a region that allows the current flowing from the electrodes to flow across the ION. Accordingly, current flowing across the electrodes can not resistively heat the ION. Moreover, since bone is a heat sink that may effectively limit the heat transport to about 0.5 cm, the heat produced by the electrodes may be effectively dissipated before it can reach the ION by conduction.

Similarly, now referring to FIG. 23, if the ION is substantially at the left edge of the ION residence zone, then placement of the bipolar electrodes in the middle of the ION residence zone fails to locate the electrodes in a region that allows the current flowing from the electrodes to flow across the ION. Again, current flowing across the electrodes may not resistively heat the ION, and the heat sink quality of bone may effectively dissipate the heat produced by the electrodes before it can reach the ION by conduction.

Moreover, even if the precise location of the BVN were known, it has been found to be difficult to access the posterior portion of the BVN from a transpedicular approach with a substantially straight probe, especially for some levels of the vertebrae that have anatomical constraints.

Therefore, in accordance with several embodiments, the systems and methods described herein allow the practitioner to heat the basivertebral nerve without having to know the precise location of the basivertebral nerve, and without having to precisely place the electrode tip next to the portion of the basivertebral nerve to be treated, while still allowing the practitioner to access the vertebral body straight (e.g., concentrically) through the pedicle.

The terms "modulation" or "neuromodulation", as used herein, shall be given their ordinary meaning and shall also include ablation, permanent denervation, temporary denervation, disruption, blocking, inhibition, therapeutic stimulation, diagnostic stimulation, inhibition, necrosis, desensitization, or other effect on tissue. Neuromodulation shall refer to modulation of a nerve (structurally and/or functionally) and/or neurotransmission. Modulation is not limited to nerves and may include effects on other tissue.

Several embodiments of the invention relate to the production of a large but well-controlled heating zone within bone tissue to therapeutically treat (e.g., modulate) an ION within the heating zone. Other embodiments provide modulation of non-spinal tissue (e.g., nerves).

Now referring to FIGS. 24-25, there is provided a representation of an embodiment in which electrodes $E_1$ and $E_2$, respectively, disposed on probes (not shown) treat (e.g., modulate) the ION. FIG. 24 provides a schematic representation of the electric field EF produced in the bone tissue by activation of the electrodes. In this case, the electric field is relatively thin. FIG. 25 provides a schematic representation of the total heating zone (THZ) produced by the electric field of FIG. 24 including both an inner resistive heating zone IR (represented by open circles) and an outer conductive heating zone OC (represented by closed circles). In this case, the inner resistive zone is produced by the joule heating of bone tissue disposed within the electric field EF, while the outer conductive zone is heated by conduction of heat from the resistive heating zone.

Still referring to FIG. 25, the positioning of two (e.g., an active and return) electrodes of an energy-transmitting device in a manner that allows the electrodes to straddle the ION residence zone (IRZ) provides a large but well-controlled total heating zone (IR+OC) within bone tissue to therapeutically treat the ION within the heating zone. Since the total heating zone is large and the electrodes straddle the IRZ, there is a high level of confidence that a portion of the ION will be present within the total heating zone. Since the total heating zone is well controlled, there is no danger (as with monopolar systems) that current flowing from the active electrode will undesirably affect collateral tissue structures Now referring to FIG. 26, if the ION is in fact substantially in the center of the ION residence zone, then placement of the two (e.g., bipolar) electrodes in a manner that straddles the ION residence zone allows the production of a total heating zone between the electrodes that includes a portion of the ION therein.

Moreover, embodiments of the invention allow the practitioner to therapeutically treat the ION even when the ION is in fact located at the edges of the ION residence zone IRZ. Now referring to FIGS. 27 and 28, if the ION is located substantially at the right edge (as in FIG. 27) or the left edge (as in FIG. 28) of the ION residence zone IRZ, then placement of the two (e.g., bipolar) electrodes in a manner that straddles the ION residence zone still allows the production of a total heating zone between the electrodes that includes a portion of the actual ION therein.

Therefore, in one embodiment, the straddling of the ION residence zone satisfactorily locates the electrodes so that the total heating zone produced by the electrode activation includes the ION irrespective of the actual location of the ION within the ION residence zone IRZ, thereby ensuring that the electrodes heat the ION to therapeutically beneficial temperatures.

Therefore, some embodiments provide a method of therapeutically treating a bone having an intraosseous nerve ION defining first and second sides of the bone, comprising inserting an energy device having an active and a return electrode into the bone, and placing the active electrode on the first side of the bone and the return electrode on the second side of the bone to define a total heating zone therebetween. A sufficiently high frequency voltage may then be applied between the active and return electrodes to generate a current therebetween to resistively heat the total heating zone sufficient to denervate the ION.

Several embodiments provide a very controlled total heating zone which exists substantially only between the paired electrodes. In accordance with several embodiments, the consequent ability to both modulate the BVN with substantial certainty and to minimize the volume of bone tissue affected by the heating appears to be novel in light of the conventional bone-related technology.

Accordingly, some embodiments of the invention are advantageous because they allow the clinician to create a sufficiently large heating zone for therapeutically treating the ION (e.g., BVN) without requiring direct access to the ION. Some embodiments of the invention are particularly advantageous because such embodiments: (i) do not require knowing the precise location of the ION, (ii) do not require directly accessing the ION, and/or (iii) have a controlled heating profile that allows a clinician to avoid heating adjacent structures such as the healthy adjacent cancellous bone tissue, the spinal cord or opposing vertebral endplates.

In accordance with several embodiments, there is provided a method of therapeutically treating a vertebral body having a BVN defining first and second sides of the vertebral body In one embodiment, the method comprises determining a BVN residence zone within which the BVN likely resides, the BVN residence zone having a first side and a second side, inserting an energy device having an active and a return electrode into the vertebral body, placing the active electrode on the first side of the residence zone and the return electrode on the second side of the residence zone to define a total heating zone therebetween, and applying a sufficiently high frequency voltage between the active and return electrodes to generate a current therebetween to resistively heat the total heating zone to a temperature sufficient to denervate the BVN.

Further aspects of embodiments of the invention will be discussed in the following portions of the specification. With respect to the drawings, elements from one figure may be combined with elements from the other figures.

BRIEF DESCRIPTION OF THE DRAWINGS

Several embodiments of the invention will be more fully understood by reference to the following drawings which are for illustrative purposes only:

FIGS. 4A-4F illustrate a method for accessing the BVN with an embodiment of the system.

FIG. 5 shows an alternative system for generating a curved path in bone

FIGS. 18A and 18B are side views of the distal end of the system of FIG. 8 with the curveable cannula in a stowed and deployed position respectively.

FIGS. 48A-48C present the temperatures recorded by thermocouples T0-T14.

DETAILED DESCRIPTION

Several embodiments of the invention are directed to systems and methods to deploy and navigate a treatment instrument, such as a neuromodulation device (e.g., a radiofrequency (RF) bipolar probe, a microwave energy delivery device, a fluid or agent delivery device) within bone. Although the systems and methods described herein are primarily directed to navigating through the bone of a vertebral member of the spine, and particularly to treat the basivertebral nerve (BVN) of a vertebral member, the treatment may be applied to any nerve and/or to any tissue segment of the body.

In accordance with several embodiments, the systems and methods of treating back pain or facilitating neuromodulation of intraosseous nerves described herein can be performed without surgical resection, without general anesthesia, and/or with virtually no blood loss. In some embodiments, the systems and methods of treating back pain or facilitating neuromodulation of intraosseous nerves described herein facilitate easy retreat if necessary. In accordance with several embodiments of the invention, successful treatment can be performed in challenging or difficult-to-access locations and access can be varied depending on bone structure. One or more of these advantages also apply to treatment of tissue outside of the spine (e.g., other orthopedic applications or other tissue).

Tube-in-Tube

Figure 1:
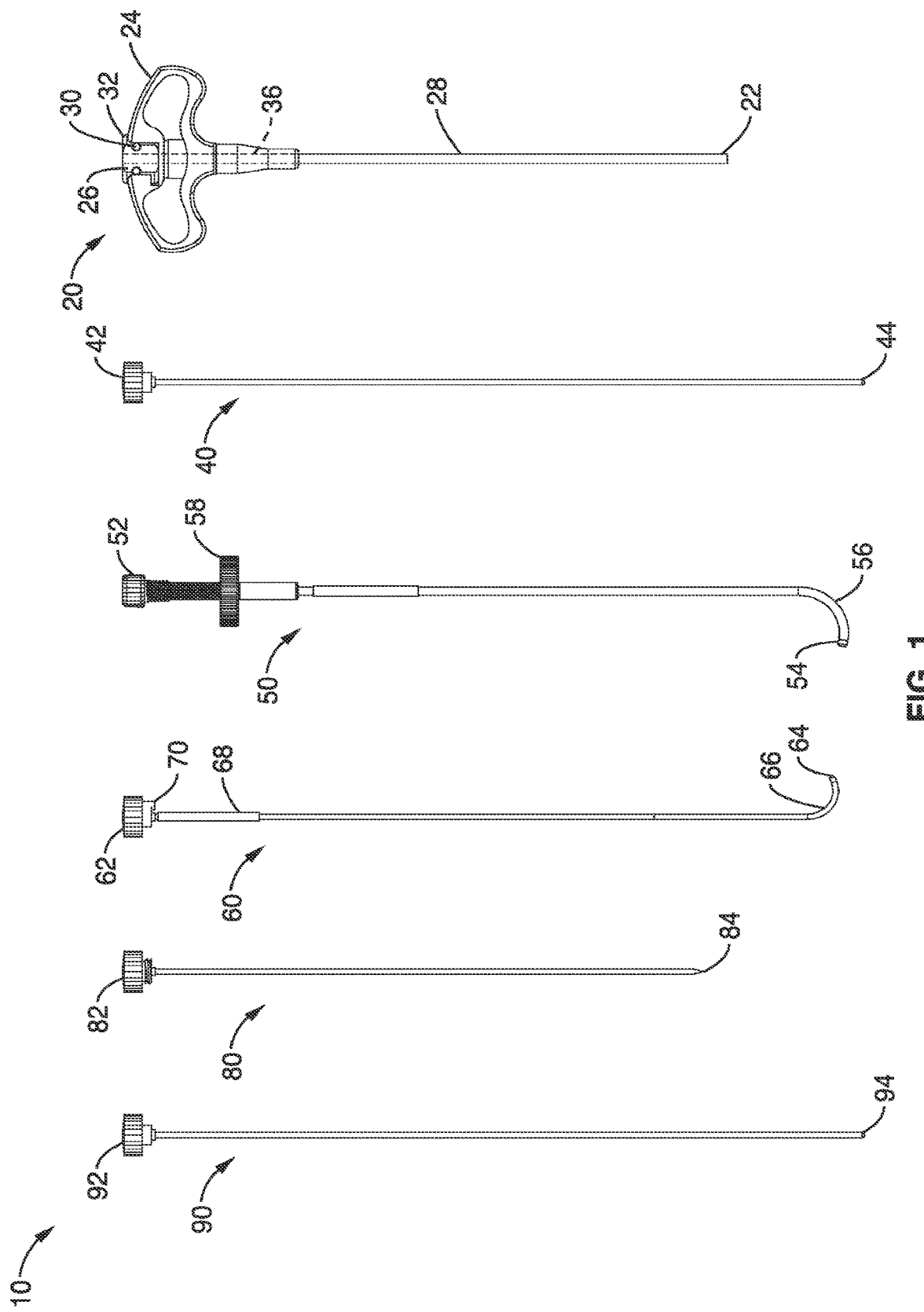
FIG. 1 is a system for generating a curved path in bone according to certain embodiments of the invention.
Figure 2:
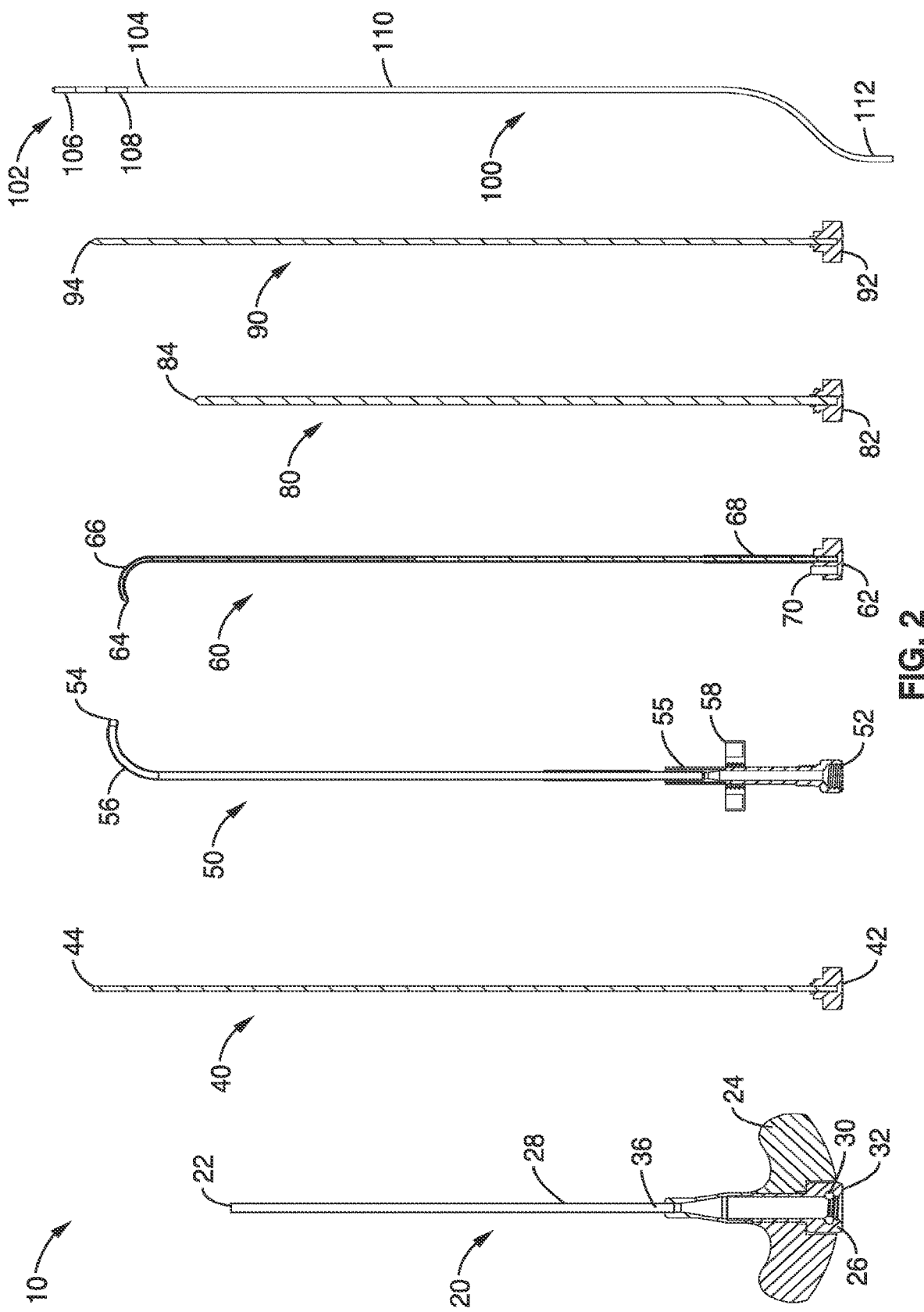
FIG. 2 is a sectional view of the system of FIG. 1.

FIGS. 1 and 2 illustrate an embodiment comprising a system or kit 10 for forming a path through bone. The system comprises a having a needle trocar 20 (the main body of the instrument set). The trocar 20 comprises an elongate shaft 28 having a handle 24 at its proximal end 32 and a central lumen 36 passing through to the distal end 22 of the trocar 20. The central lumen 36 is generally sized to allow the other instruments in the system 10 to be slideably introduced into the patient to a treatment region. System 10 further comprises a straight stylet 80 having a sharp-tipped needle 84 at its distal end that is used with the needle trocar 20 to create the initial path through the soft tissue and cortical shell to allow access to the cancellous bone, a curved cannula 50 that is used to create/maintain the curved path within the bone/tissue. A straightening stylet 40 may be used to straighten out the curve and load the curved cannula 50 into the needle trocar 20. A curved stylet 60 may be used in conjunction with the curved cannula 50 to create the curved path within the bone/tissue, and a channeling stylet 90 is used to create a working channel for a treatment device (such as RF probe 100) beyond the end of the curved path created by the curved cannula 50.

The surgical devices and surgical systems described may be used to deliver numerous types of treatment devices to varying regions of the body. Although the devices and systems are particularly useful in navigating through bone, in one embodiment they may also be used to navigate through soft tissue, or through channels or lumens in the body, particularly where one lumen may branch from another lumen.

The following examples illustrate the system 10 applied to generating a curved bone path in the vertebral body, and more particularly for creating a bone path via a transpedicular approach to access targeted regions in the spine. In particular, the system 10 may be used to deliver a treatment device to treat or ablate intraosseous nerves, and in particular that basivertebral nerve (BVN). Although the system and methods provide significant benefit in accessing the BVN, in one embodiment, the system 10 may similarly be used to create a bone path in any part of the body (such as the humerus, femur, pelvis, fibula, tibia, ulna, radius, etc.)

Figure 3:
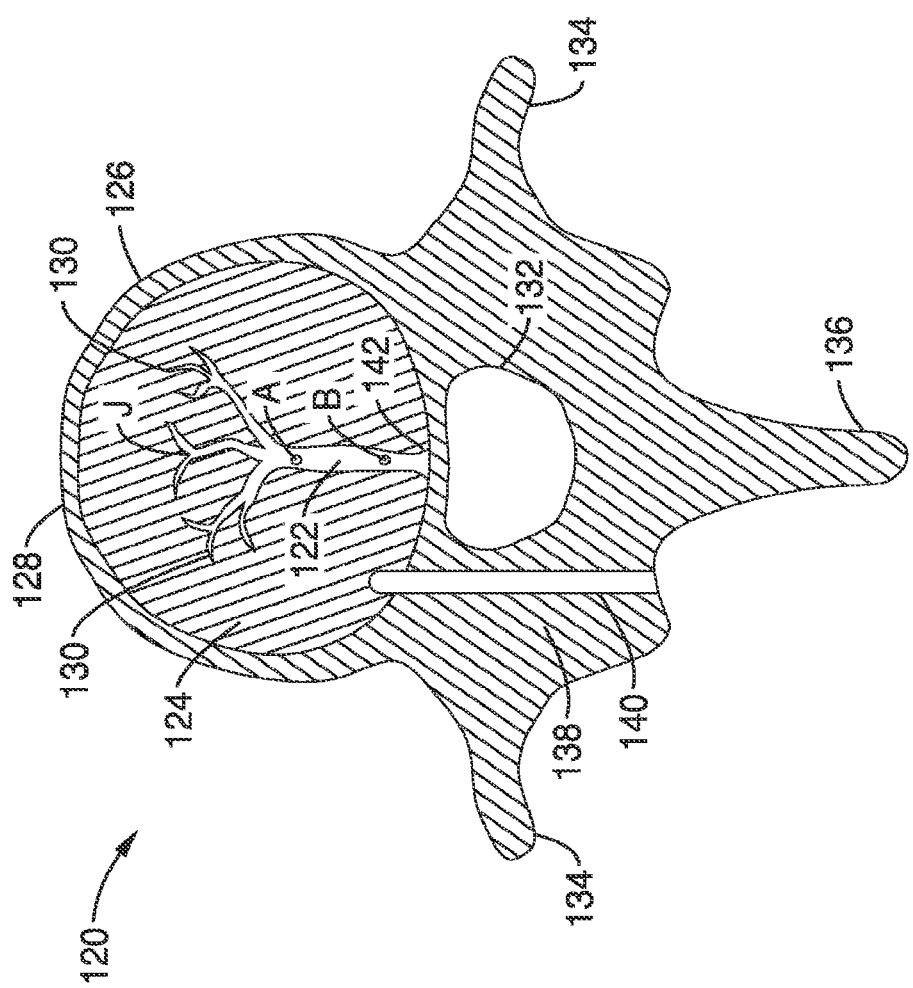
FIG. 3 illustrates a sectioned view of a vertebral body with a path bored through the cortical shell.

FIG. 3 illustrates a cross-sectional view of a vertebra 120. Recently, the existence of substantial intraosseous nerves 122 and nerve branches 130 within human vertebral bodies (basivertebral nerves) has been identified. The basivertebral nerve 122 has, at least one exit 142 point at a location along the nerve 122 where the nerve 122 exits the vertebral body 126 into the vertebral foramen 132. Minimally invasive interventional treatments for lower back pain is a promising alternative to existing non-surgical conservative therapy or spinal surgery treatments, including spinal fusion. The basivertebral nerve may provide innervation to the trabecular bone of the vertebral body. The basivertebral nerves accompany the basivertebral vessels that enter the vertebrae through the large posterior neurovascular foramen. The basivertebral nerves may comprise segments having lengths between 5 and 8 mm and diameters of 0.25 to 0.5 mm. The basivertebral nerve is believed to conduct pain receptive signals from intraosseous sources. Accordingly, modulation (e.g., defunctionalization, ablation) of the basivertebral nerve is provided in several embodiments herein to reduce chronic or acute back pain.

In accordance with several embodiments, the basivertebral nerves are at, or in close proximity to, the exit point 142. In some embodiments, the exit point 142 is the location along the basivertebral nerve where the basivertebral nerve exits the vertebra. Thus, the target region of the BVN 122 is located within the cancellous portion 124 of the bone (i.e., to the interior of the outer cortical bone region 128), and proximal to the junction J of the BVN 122 having a plurality of branches 130. Treatment in this target region is advantageous because only a single portion of the BVN 122 need be effectively treated to modulate (e.g., denervate or otherwise affect the entire BVN system. Treatment, in accordance with one embodiment, can be effectuated by focusing in the region of the vertebral body located between 60% (point A) and 90% (point B) of the distance between the anterior and posterior ends of the vertebral body. In some embodiments, treatment is located at or proximate (e.g., posterior to) the junction J. In some embodiments, treatment of the BVN 122 in locations more downstream than the junction J requires the denervation of each branch 130. The target region may be identified or determined by pre-operative imaging, such as from MRI or CT images. In various embodiments, treatment can be effectuated by focusing in the region of the vertebral body located at a region that is more than 1 cm from the outer cortical wall of the vertebral body, within a region that is centered at or about 50% of the distance from the posterior outer wall of the vertebral body to the anterior outer wall, and/or within a region that is between 10% and 90% (e.g., between about 10% and about 60%, between about 5% and about 65%, between about 10% and about 55%, or overlapping ranges thereof) of the distance from the posterior outer wall of the vertebral body to the anterior outer wall.

In various embodiments, the junction J is located at a location of the terminus of the vertebral foramen, at the junction between a main trunk of the BVN 122 and the initial downstream branches, at a location corresponding to a junction between at least one of the initial downstream branches and its respective sub-branches, or other locations along the BVN 122.

In one approach for accessing the BVN, the patient's skin is penetrated with a surgical instrument which is then used to access the desired basivertebral nerves, i.e., percutaneously. In one embodiment, a transpedicular approach is used for penetrating the vertebral cortex to access the BVN 122. A passageway 140 is created between the transverse process 134 and spinous process 136 through the pedicle 138 into the cancellous bone region 124 of the vertebral body 126 to access a region at or near the base of the nerve 122. In one embodiment, a postereolateral approach (not shown) may also be used for accessing the nerve. The transpedicular approach, postereolateral approach, basivertebral foramen approach, and other approaches are described in more detail in U.S. Pat. No. 6,699,242, herein incorporated by reference in its entirety.

FIGS. 4A-F illustrate a method for accessing the BVN with the system 10. First, the straight stylet 80 is inserted in aperture 26 at the proximal end 32 of needle trocar 20. The straight stylet 80 is advanced down the central lumen 36 (see FIG. 2) of the trocar 20 until the proximal stop 82 abuts against handle 24 of the trocar 20, at which point the distal tip 84 of straight stylet protrudes out of the distal end 22 of the trocar 20. In accordance with several embodiments, the tip 84 of the straight stylet 80 comprises a sharp tip for piercing soft tissue and bone.

Figure 4A:
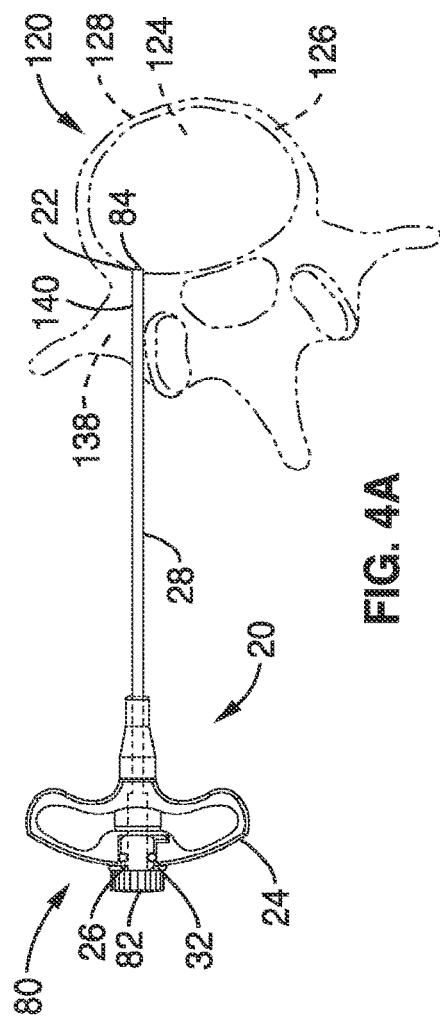

Referring now to FIG. 4A, in some embodiments, the assembly (trocar 20 and straight stylet 80) is advanced through soft tissue to the surface of the bone. Once the proper alignment is determined, the assembly may be advanced through the cortical shell of pedicle 138 and into the cancellous interior 124 of the bone.

In some embodiments, after the proper depth is achieved, the straight stylet 80 is removed from the trocar 20, while the trocar 20 remains stationary within the vertebra 120. The straightening stylet 40 may be inserted into proximal aperture 52 (see FIG. 2) of the curved cannula 50 and advanced along the central lumen of the curved cannula 50 until the stop 42 of the stylet 40 abuts up to the proximal end of the curved cannula. In some embodiments, this forces the distal tip of the straight stylet through the curved section 56 of the curved cannula 50 to straighten out the curve 56. In some embodiments, the straight stylet comprises a hard, noncompliant material and the distal end 56 of the curved cannula 50 a compliant, yet memory retaining material (e.g. Nitinol, formed PEEK, etc.) such that the curved 56 section yields to the rigidity of the straightening stylet 40 when installed, yet retains its original curved shape when the stylet 40 is removed.

Figure 4B:
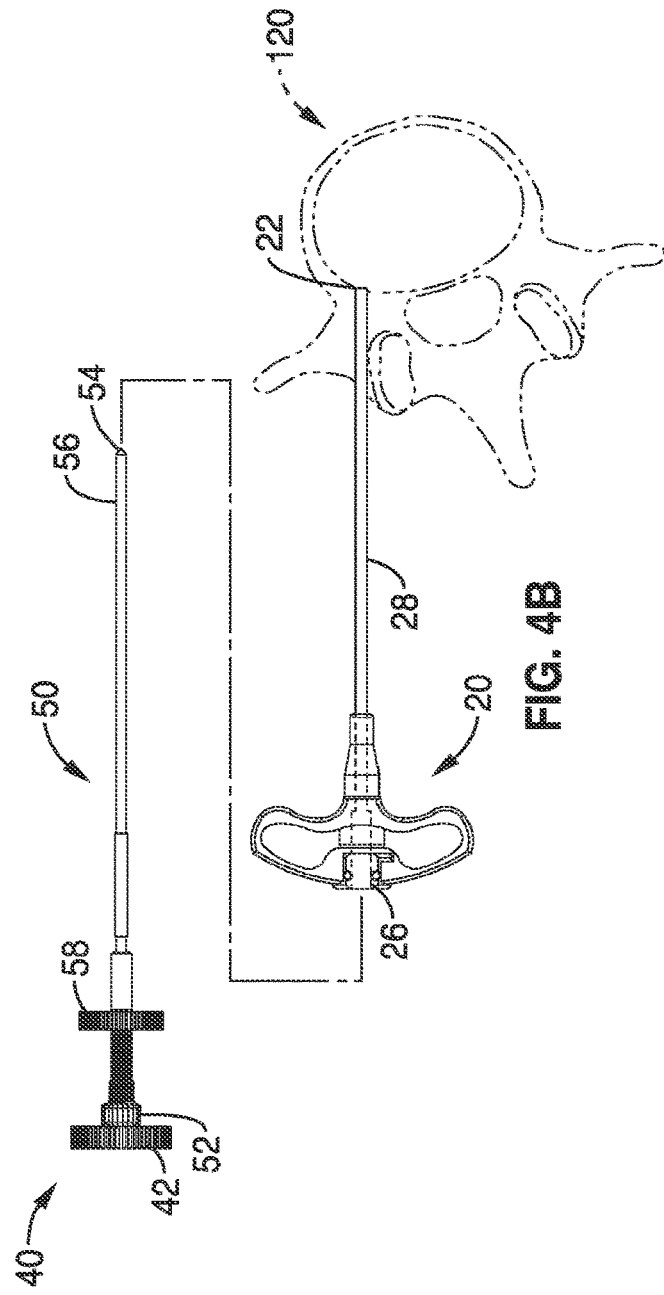

As shown in FIG. 4B, once the straightening stylet 40 is secure and the curved cannula 50 is straight, they may be inserted together into the needle trocar 20 and secured. Proper alignment (e.g. prevent rotation, orient curve direction during deployment) may be maintained by aligning a flat on the upper portion 58 of the curved cannula 50 to an alignment pin secured perpendicularly into the needle trocar 20 handle 24. Other alignment elements may also be used (e.g., visual indicia such as lines, text, shapes, orientations, or coloring). In some embodiments, once the curved cannula 50 is secure, the straightening stylet 40 is removed, while the curved cannula 50 remains stationary within the trocar 20.

Referring to FIG. 4C, the curved stylet 60 can then straightened out by sliding the small tube 68 proximally to distally on its shaft towards the distal tip 64 or from the distal tip 64 proximally on its shaft towards the proximal end 62. In some embodiments, once the curved distal tip 66 is straightened out and fully retracted inside the small tube 68, the curved stylet 60 is inserted into the proximal aperture 52 of the curved cannula 50, which still resides inside the needle trocar 20. As the curved stylet 60 is advanced into the curved cannula 50, the small tube 68 may be met by a stop 55 (see FIG. 4C). As the curved stylet 60 continues to advance, the small tube 68 may be held inside the handle of the curved cannula 50. This can allow the curve of the stylet 60 to be exposed inside the curved cannula 50. To create the maximum force, the curve of the two parts (50 & 60) may be aligned. To facilitate alignment, the cap on the curved stylet 60 can have an alignment pin 70 which engages with alignment notch 52 on the proximal end of the curved cannula 50. Other alignment elements may also be used (e.g., visual indicia such as lines, text, shapes, orientations, or coloring).

Once the stylet 60 is fully seated and aligned with the curved cannula 50, the tip of the curved stylet 60 may protrude from the tip of the curved cannula 50 by about ⅟₁₆ to ³⁄₁₆ inches. This protrusion can help to drive the curve in the direction of its orientation during deployment.

Referring now to FIG. 4D, with the curved stylet 60 and the curved cannula 50 engaged, the locking nut 58 at the top of the curved cannula 50 may be rotated counter clockwise to allow the cannula 50 and stylet 60 to be advanced with relation to the needle trocar 20 such that the proximal end 52 about against 58, advancing the curved cannula 50 and stylet 60 beyond the distal opening of trocar 20 to generate a curved path in the cancellous bone region 124. As the curved cannula 50 and stylet 60 are advanced they can curve at a radius of 0.4 to 1.0 inches through cancellous bone and arc to an angle between approximately 0° to approximately 180° (e.g., from approximately 5° to approximately 110°, from approximately 45° to approximately 110°, from approximately 15° to approximately 145°, from approximately 30° to approximately 120°, from approximately 60° to approximately 90°, from approximately 10° to approximately 45°, overlapping ranges thereof, or any angle within the recited ranges). Once the curved cannula 50 and stylet 60 are deployed to the intended angle, the locking nut at the top of the curved cannula 50 may be engaged with the needle trocar 20 to stop any additional advancement of the curved stylet cannula assembly.

Figure 7B:
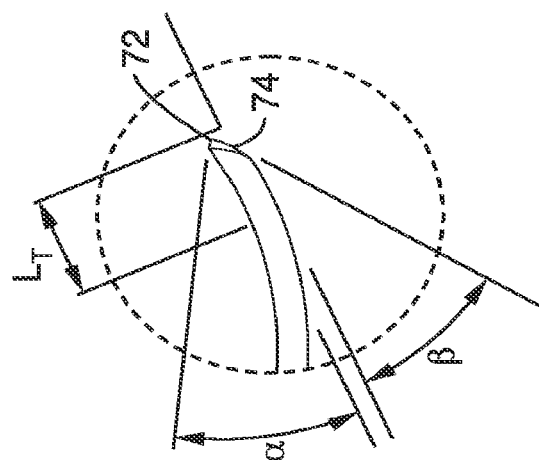
FIGS. 7A-7B show a curved stylet.
Figure 7A:
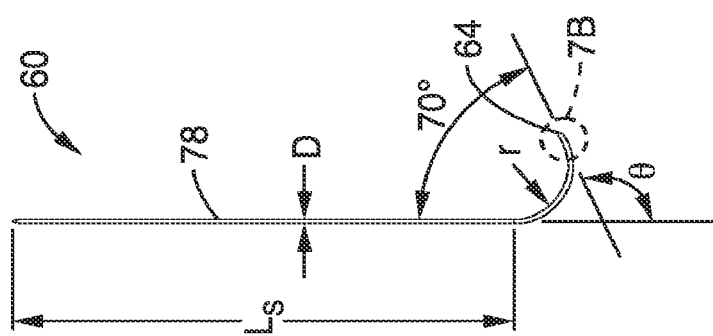

Referring to FIGS. 7A-7B illustrate the tip of a curved stylet 60, which has been formed with two angles. To help the curve deployment in the proper direction, the curve 66 of the curved stylet 60 may be shaped in a predetermined orientation. The angle on the inside of the curve 72 may be less than the angle on the outside of the curve 74. This disparity in angles helps the stylet cannula assembly (collectively 50, 60) curve in the bone as bone pushes against outside curve face 74, thereby ensuring the curve radius is maintained during deployment, according to one embodiment.

Referring now to FIG. 4E, the curved stylet 60 may then be removed and replaced by the channeling stylet 90. The tip 94 of the channeling stylet 90 may be advanced beyond the end 54 of the curved cannula 50 towards the intended target treatment zone.

Referring now to FIG. 4F, in some embodiments, once the channeling stylet 90 reaches the target treatment zone, it is removed, thereby creating a working channel 146. In some embodiments, channel 140 generally has a first section 142 that crosses the cortical bone of the pedicle 138, followed by a curved path 144. These sections may be occupied by curved cannula 50 such that a treatment device fed through the cannula 50 will have to follow the curve of the cannula 50 and not veer off in another direction. The channel 140 may further comprise the linear extension 146 in the cancellous bone 124 to further advance the treatment device toward the treatment site T. In some embodiments, the treatment site T corresponds to a location of a terminus of the nerve 122 (e.g., terminus of the basivertebral foramen or the junction between a main trunk of the basivertebral nerve and its sub-branches). In some embodiments, the treatment site or location T is identified without knowing the precise location of the basivertebral nerve 122.

With the trocar 20 and curved cannula 50 still in place, a treatment device (e.g. treatment probe 100 shown in FIG. 2) with an active element 102 on the distal end 104 of elongate flexible catheter 110 may be delivered to the target treatment location T to perform a localized treatment. In some embodiments, the target treatment location T is identified prior to introduction of the trocar 20 by magnetic resonance (MR) imaging, computed tomography (CT) imaging, or other imaging modalities. The introduction of the trocar 20, curved cannula 50, treatment device, and/or other instruments can be visualized in real time using fluoroscopic or other imaging to ensure proper introduction and orientation within the target treatment location. In accordance with several embodiments, the treatment (e.g., neuromodulation) can be performed at multiple levels of vertebrae (simultaneously or sequentially with one, two, three or more treatment devices). The levels may be adjacent or spaced apart. For example, treatments can be performed at the L4 and L5 levels, at the L3-L5 levels, at the L5 and S1 levels, or at other combinations of lumbar, sacral, cervical or thoracic vertebral levels. In some embodiments, a single treatment system or device (e.g., a generator and one or more radio frequency probes) or multiple treatment systems or devices (e.g., two or more generators each with one, two, three or more radiofrequency probes) are used to administer the treatment. In one embodiment, multiple treatment probes can be daisy-chained or otherwise reversibly or integrally coupled to (or integral with) each other and/or to a single generator or other energy generation module to simultaneously treat multiple levels of vertebrae that are spaced apart. A "y" shaped device may be used in some embodiments. In various embodiments, the treatment devices comprise one, two, three or more energy sources (e.g., electrodes) that can be connected by one or more connection members or elements to space the energy sources apart to simultaneously treat multiple levels of vertebrae. Simultaneous treatment of two or more vertebrae may be treated with radiofrequency or other therapeutic modalities (ultrasound, radiation, steam, microwave, laser, cryoablation, etc.). Different therapeutic modalities or different energy levels of the same therapeutic modality that work simultaneously are provided in some embodiments.

In one embodiment, the active element 102 is delivered to the treatment site and activated to deliver therapeutic treatment energy. In various embodiments, the treatment device comprises a probe, catheter, antenna, wire, tube, needle, cannula, sleeve, or conduit. The treatment device may comprise an RF delivery probe having bipolar electrodes 106 and 108 that deliver a therapeutic level of heating (e.g., thermal dose) to modulate (e.g., stimulate or ablate) at least a portion of the nerve 122.

In some embodiments, the treatment device comprises a microwave energy delivery device comprising one or more antennas. In some embodiments, the treatment device comprises a chemical ablation or cryoablation device comprising a fluid conduit for delivery (e.g., injection) of fluids, chemicals or agents (e.g., neurolytic agents) capable of ablating, stimulating, denervating, blocking, disrupting, or otherwise modulating nerves. In some embodiments, the treatment device comprises an ultrasound delivery device having one or more transducers or a laser energy delivery device comprising one or more light delivery elements (e.g., lasers, such as fiber optic lasers or vertical cavity surface emitting lasers (VCSELs), or light emitting diodes (LEDs)).

According to several embodiments of the invention, many treatment modalities can be delivered to the treatment site for modulation of nerves or other tissue (e.g., neuromodulation, ablation, temporary or permanent denervation, stimulation, inhibition, blocking, disruption, or monitoring). For example, treatment may be affected by monopolar or tripolar RF, ultrasound, radiation, steam, microwave, laser, or other heating means. These modalities may be delivered to the treatment site through one or more of the embodiments of systems and/or methods disclosed herein, and treatment applied such that the nerve is heated to the desired level for the desired duration (e.g., a sufficient thermal dose is applied) to affect stimulation, denervation, ablation or the desired therapeutic effect.

For example, the ultrasonic energy can be controlled by dosing, pulsing or frequency selection to achieve the desired heating level for the desired duration. Similarly, microwave treatment may be applied using a microwave energy delivery catheter and/or one or more antennas. Microwaves may be produced with a frequency in the range of 300 GHz to 300 MHz, between 1 GHz and 5 GHz, between 2 GHz and 10 GHz, between 10 GHZ and 100 GHz, 100 GHz and 300 GHz, between 50 GHz and 200 GHz, between 200 GHz and 300 GHz, or overlapping ranges thereof. Pulses of between 1-5 seconds, between 2-3 seconds, between 0.5 seconds-2 seconds, between 4-5 seconds, between 5-10 seconds, between 10-30 seconds, or overlapping ranges between, in duration may be generated. In some embodiments, a single pulse, 1-3 pulses, 2-4 pulses, 3-8 pulses, 8-20 pulses, or overlapping ranges between, may be generated.

Radiation therapy may use radiation sources comprising any one of a number of different types, such as, but not limited to, particle beam (proton beam therapy), cobalt-60 based (photon or gamma-ray source such as that found in the GammaKnife), or linear accelerator based (e.g., linac source). The dose of radiation delivered to the patient will typically range between 10 Gy and 70 Gy. However, because the treatment region is contained within the large bony mass of the vertebral body, higher doses may be contemplated, as there is little risk to surrounding tissues that are more vulnerable. The dose may be varied based on the treatment volume, or other variables such as treatment time and dose concentration. A prescription of 35 instances of a 2 Gy dose might be replaced by 15 instances of a 3 Gy dose, a technique known as "hypofractionation." Taken to its logical extreme, this might be replaced with a single 45 Gy dose if the dosage delivered to healthy tissue can be reduced significantly. An identification dose may in some embodiments be used prior to the treatment dose, for example, to elicit some response form the patient relating to the patient's pain. The identification dose is generally a much smaller dose than treatment dose TD, so as not to damage healthy tissue. An exemplary dose may range from 0.5 Gy to 5 Gy. However, this range may also change based on considerations such as anatomy, patient, etc.

Additionally or alternatively, the treatment device may comprise a fluid or agent delivery catheter that deposits an agent or fluid, e.g. bone cement, phenol, alcohol, neurotoxin, inhibitory or stimulatory drug, chemical, or medicament, for neuroablation or permanent or temporary denervation, or other therapeutic agent, to the treatment site or location T. Growth factors, stein cells, gene therapy or other biological therapeutic agents may also be delivered.

In some embodiments, cryogenic cooling may be delivered for localized treatment of the BVN or an intraosseous nerve using, for example, liquid nitrogen, liquid nitrous oxide, liquid air, or argon gas. Cryotherapy may be delivered in one or more freeze cycles. In several embodiments, two freeze-thaw cycles are used. In some embodiments, 3-5 freeze-thaw cycles are used. In some embodiments, a single freeze-thaw cycle is used In some embodiments, a desired temperature of the tissue is $-40°$ C. to $-50°$ C., $-20°$ C. to $-40°$ C., $-35°$ C. to $-45°$ C., $-50°$ C. to $-80°$ C., or overlapping ranges thereof. The desired temperature may be maintained for 5-20 minutes, 10-15 minutes, or greater than 10 minutes, depending on the temperature and thermal dose desired. Furthermore, treatment may be effected by any mechanical destruction and or removal means capable of severing or denervating the BVN. For example, a cutting blade, bur, electrocautery knife or mechanically actuated cutter typically used in the art of orthoscopic surgery may be used to effect denervation of the BVN.

In addition to or separate from treating (e.g., modulating) the BVN or an intraosseous nerve, a sensor may be delivered to the region to preoperatively or postoperatively measure nerve conduction at the treatment region. In this configuration, the sensor may be delivered on a distal tip of a flexible probe that may or may not have treatment elements as well.

In accordance with several embodiments, the goal of the treatment may be ablation, or necrosis of the target nerve or tissue, or some lesser degree of treatment to denervate the BVN. For example, the treatment energy or frequency may be just sufficient to stimulate the nerve to block the nerve from transmitting signals (e.g. signals indicating pain) without ablation or necrosis of the nerve. The modulation may be temporary or permanent.

In several embodiments, the therapeutic modalities described herein (including energy or agent delivery) modulates neurotransmission (e.g., neurotransmitter synthesis, release, degradation and/or receptor function, etc.). In some embodiments, signals of nociception are affected. Effects on neurokinin A, neuropeptide Y, substance P, serotonin and/or other signaling pathways are provided in some embodiments. Calcium and/or sodium channel effects are provided in one embodiment. In some embodiments, G-protein coupled receptors are affected.

Once the treatment is complete, the probe 100 may be withdrawn. The curved cannula 50 may then be withdrawn into the needle trocar 20. The needle trocar 20 with the curved cannula 50 may then be removed and the access site may be closed as prescribed by the physician or other medical professional.

In the above system 10, the design of the curves 56 and 66 of the curved cannula 50 and curved stylet 60 is such that a flexible element (e.g., distal portion of the treatment device) can navigate through the angular range of deployment of the curved cannula 50 (e.g., Nitinol or other material tube). The curved cannula 50 allows the flexible element to navigate through a curve within bone without veering off towards an unintended direction. Cancellous bone density varies from person to person. Therefore, creating a curved channel within varying density cancellous bone 124 will generally not predictably or accurately support and contain the treatment device as it tries to navigate the curved channel.

With the system 10, the treatment device 100 is deployed into the bone through the curved cannula 50 (e.g., Nitinol tube), which supports the flexible element (e.g., distal portion of the treatment device) as it traverses through the curve. When it departs from the tube, it will do so in a linear direction along path 146 towards the target zone. In accordance with several embodiments, this advantageously allows the user to predictably and accurately deploy the treatment device towards the target zone or location T regardless of the density of the cancellous bone.

In some embodiments, a radius of curvature that is smaller than that which can be achieved with a large diameter Nitinol tube may be advantageous. To achieve this, the curved portion of the curved cannula 50 may take one of several forms. In one embodiment, the curved cannula 50 is formed from a rigid polymer (e.g., formed PEEK) that can be heat set in a particular curve. If the polymer was unable to hold the desired curve, an additional stylet (e.g. curved stylet 60) of Nitinol, flexible stainless steel, shape memory material, metallic or metallic-based material, or other appropriate material, may also be used in conjunction with the polymer tube to achieve the desired curve. In some embodiments, the stylet comprises a braided tube, rod, or wire. In some embodiments, the stylet comprises a non-braided tube, rod, or wire, or combinations thereof. This proposed combination of material may encompass any number or variety of materials in multiple different diameters to achieve the desired curve. These combinations only need to ensure that the final outside element (e.g. trocar 20) be "disengageable" from the internal elements and have an inner diameter sufficient to allow the desired treatment device 100 to pass to the treatment region T. In accordance with several embodiments, the treatment region T is in a posterior section (e.g., posterior to a midline) of the vertebral body. The treatment region T may correspond to an expected location of a terminus of a basivertebral foramen.

In one embodiment, the curved cannula 50 may comprise a Nitinol, shape memory material, stainless steel or other metallic tube having a pattern of reliefs or cuts (not shown) in the wall of the tube (particularly on the outer radius of the bend). The pattern of cuts or reliefs could allow the tube to bend into a radius tighter than a solid tube could without compromising the integrity of the tubing wall. The curved portion of the curved cannula 50 may comprise a different material than the main body of the curved cannula or the same material.

FIG. 5 illustrates a second embodiment of the system or kit 200 that may be used to reduce the number of steps required for the procedure. The second embodiment includes a needle trocar 20, straightening stylet 40, used with the needle trocar 20 and the curved cannula 50 to create the initial path through the soft tissue and cortical shell to allow access to the cancellous bone, curved stylet 60 used in conjunction with the curved cannula 50 to create the curved path within the bone/tissue, and channeling stylet 90 used to create a working channel for a treatment device (e.g., probe) beyond the end of the curved path created by the curved stylet.

In an embodiment of the method, the straightening stylet 40 is inserted into the curved cannula 50 and secured. In this embodiment, the straightening stylet 40 has a sharp tip 46 designed to penetrate bone. Once the straightening stylet 40 is secure and the curved cannula 50 is straight, they are inserted into the needle trocar 20 and secured. In tone embodiment, the curved cannula 50 and straightening stylet 40 are inserted into the shaft 28 of the trocar 20 only as far as to have sharp tip 46 of the straightening stylet 40 protrude from the distal end 22 of the trocar 20. Proper alignment is maintained by aligning a flat on the upper portion of the curved cannula 50 with a pin secured perpendicularly into the needle trocar 20 handle. Other alignment elements may also be used (e.g., visual indicia such as lines, text, shapes, orientations, or coloring).

Figure 6:
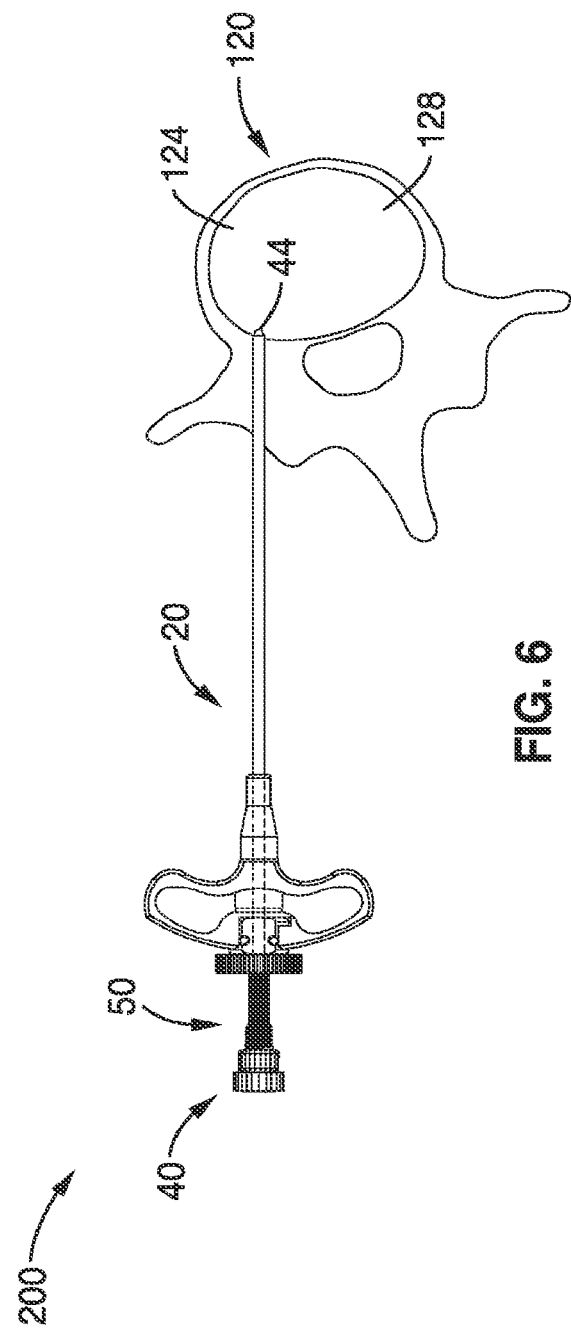
FIG. 6 shows the system of FIG. 5 being installed in a vertebral body.

Referring now to FIG. 6, once the curved cannula 50 is secure, the assembly (trocar 20, curved cannula 50, and straightening stylet 40) may be advanced through soft tissue to the surface of the bone. After finding the proper alignment at the pedicle 138 of vertebra 120, the assembly (trocar 20, curved cannula 50, and straightening stylet 40) may be advanced through the cortical shell 128 and into the cancellous interior 124 of the bone.

After the proper depth is achieved, the straightening stylet 40 may be removed. The curved stylet 60 may then be straightened out by sliding the small tube 68 on its shaft towards the distal tip 64. In some embodiments, the curved distal tip 66 is straightened out and fully retracted inside the small tube 68, and then the curved stylet 60 is inserted into the curved cannula 50, which still resides inside the needle trocar 20. Once the curved stylet 60 is inserted into the curved cannula 50, the small tube 68 may be met by a stop 55 (see FIG. 4C). As the curved stylet 60 continues to advance, the small tube 68 may be held inside the handle of the curved cannula 50. This can allow the curve of the stylet 60 to be exposed inside the curved cannula 50.

To create a maximum force, it may be advantageous that the curves of the two parts (50 & 60) are aligned. To ensure alignment, the cap on the curved stylet 60 may have an alignment pin, which engages with a notch on the top of the curved cannula 50. Other alignment elements may also be used (e.g., visual indicia such as lines, text, shapes, orientations, or coloring).

When the stylet 60 is fully seated and aligned with the curved cannula 50, the tip of the curved stylet 60 may protrude from the tip of the curved cannula 50 by about 1/16 to 3/16 inches. This protrusion can help to drive the curved cannula 50 in the direction of its orientation during deployment. Once the curved stylet 60 and the curved cannula 50 are engaged, the lock nut at the top of the curved cannula 50 may be rotated counter clockwise to allow the cannula 50 and stylet 60 to be advanced with relation to the needle trocar 20 (as shown in FIG. 4D). As the curved cannula and stylet are advanced they generate a curved path toward the treatment location T. Once the curved cannula 50 and stylet 60 are deployed to the intended angle, the lock nut at the top of the curved cannula 50 may be engaged with the needle trocar 20 to stop any additional advancement of the curved stylet cannula assembly.

The curved stylet 60 may then be removed and replaced by the channeling stylet 90. In some embodiments, the channeling stylet 90 is advanced beyond the end of the curved cannula 50 (see FIG. 4E) towards the intended target treatment zone, thereby creating a working channel for the active element to be inserted. Once the channeling stylet 80 reaches the target treatment zone, it can be removed and replaced by the treatment device 100, which can be delivered to the treatment site T and activated.

Once the treatment is complete, the treatment device 100 can be withdrawn. In some embodiments, the curved cannula 50 is then withdrawn into the needle trocar 20. The needle trocar 20 with the curved cannula 50 can then be removed and the access site can be closed as prescribed by the physician or other medical professional.

FIGS. 7A and 7B illustrate detailed views of a Nitinol or other shape memory material wire, rod or tube for the curved stylet 60 (proximal end not shown). The wire comprises a shaft 78 having constant diameter D and a length $L_s$ that may vary according to the application and desired depth to the treatment location. The wire has a preformed distal tip that is curved to have a radius r that redirects the distal tip 64 at an angle θ with the shaft. As shown in FIG. 7A, angle θ is shown to be approximately 110°. However, in one embodiment, the preformed tip may have an angle ranging from a few degrees (slight deflection off axis), to up to 180° (e.g. directing back toward the proximal end).

As shown in FIG. 7B detailing the distal tip 64, the tip may have a distal extension $L_T$ that extends away from the shaft 78. To promote channeling along a path that follows radius r, the distal tip 64 is configured with dual-plane bevels 74 and 72. Plane 74 is offset at angle β, and plane 72 is offset at angle α. This configuration can allow for the stylet and/or curved cannula to travel through bone in a path correlating to the specified curve in the stylet and/or cannula.

In the example illustrated in FIGS. 7A and 7B, the curved stylet 60 may have a shaft length $L_S$ of approximately 2-5 inches (e.g., 3.6 in.), diameter D of approximately 0.02-0.06 inches (e.g., 0.040 in.), and a distal tip length $L_T$ of about 0.08-0.16 inches (e.g., 0.125 in.), a radius r of about 0.2-0.6 inches (e.g., 0.4 in.), and angle β=35° and angle α=31°. The angles may vary by up to about 10 degrees, up to 15 degrees, or up to 20 degrees in either direction. It should be noted that the above dimensions are for illustration only, and may vary depending on the anatomy and tissue type. For example, the modulation devices disclosed herein can be used, in some embodiments, to modulate nerves or treat tissue in other areas of the spine. Non-spinal applications are also contemplated. For example, denervation of renal nerves, cardiac ablation and other non-spinal treatment can be accomplished according to several embodiments described herein.

Any of the embodiments described herein may be provided as a kit of instruments to treat different regions of the body. For example, the location, orientation and angle of the treatment device with respect to the trocar 20 may be varied by providing a set of instruments at varying increments. This may be achieved by varying the curvature (56, 66) in the curved cannula 50 and curved stylet 60. The curvature may be varied by varying the radius of curvature r, the insertion depth (shaft length $L_S$ and tip length $L_T$, and/or the final exit angle θ with respect to the trocar 20 central bore. Thus, the physician or other clinician may select a different kit for treating a lumber spine segment as opposed to a cervical spine segment, as the anatomy will dictate the path that needs to be channeled.

Thus, when treating different spine segments, a set out of the kit may be selected to match the vertebra (or other region being treated). For example, delivering the treatment device at or near the BVN junction or terminus for a lumbar vertebra may have a different angle than for a sacral or cervical vertebra, and may vary from patient to patient. The set may be selected from the kit intraoperatively, or from a pre-surgery diagnostic evaluation (e.g. radiographic imaging of the target region).

Tube in Windowed Tube

Figure 8:
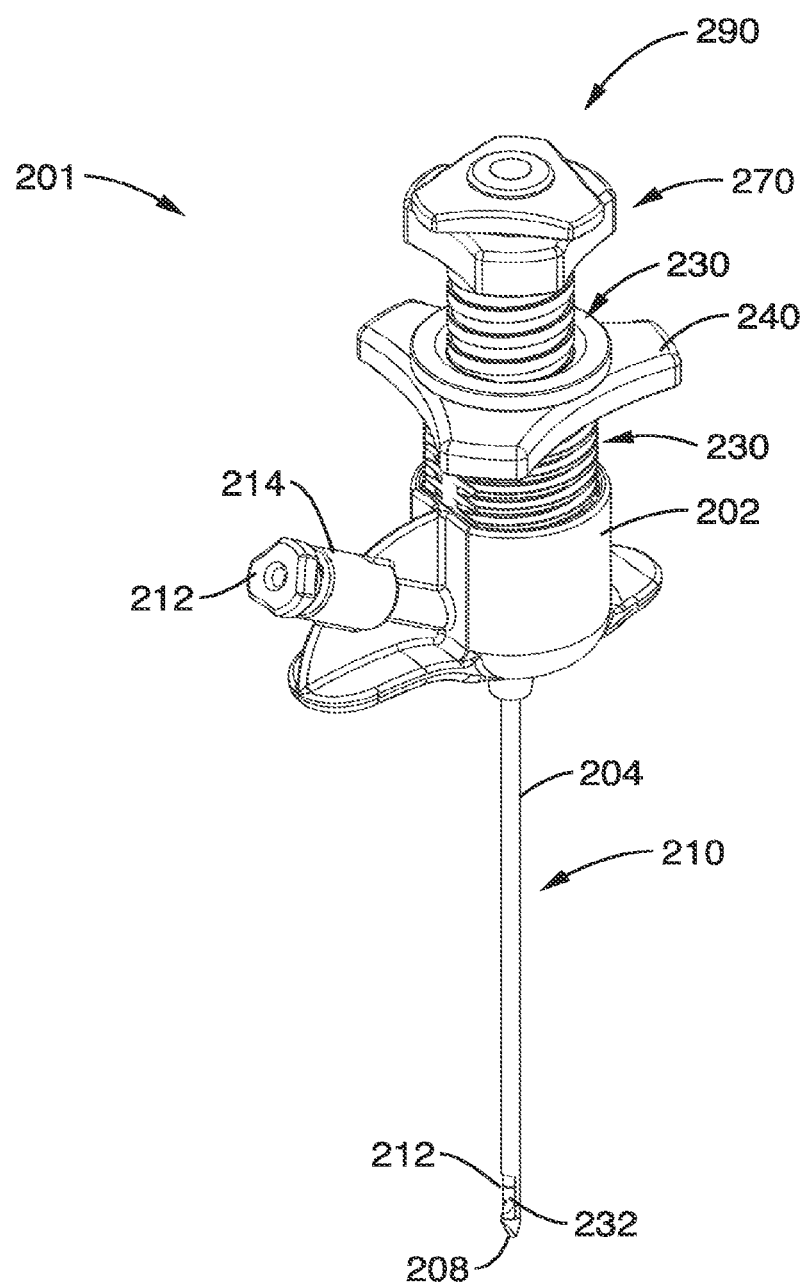
FIG. 8 illustrates a perspective view of a system for generating a curved path in bone.

FIGS. 8-18B illustrate a system 201 for generating a curved path in bone. FIG. 8 shows a perspective view of system 201 in a configuration ready for deployment within a patient's body. System 201 comprises an introducer/trocar 210 having a proximal end housing 202 coupled to an elongate delivery tube 204. The distal end tip 208 has a sharpened and/or beveled tip to facilitate entry into and delivery through at least a portion of a bony mass such as the vertebral body. The proximal end of the assembly (e.g., drive nut 270), may comprise a hard, rigid material to allow the trocar 210 to be tapped into place with a mallet or the like.

The elongate delivery tube 204 comprises a laterally positioned radial opening or window 212 disposed just proximal or at the distal tip 208. The window 212 provides radial access from the central channel 218 of tube 204 so that an instrument or probe (e.g. probe 250 distal end) may be delivered at an angle (e.g. non-axial) with respect to the tube axis or central channel 218.

Figure 9:
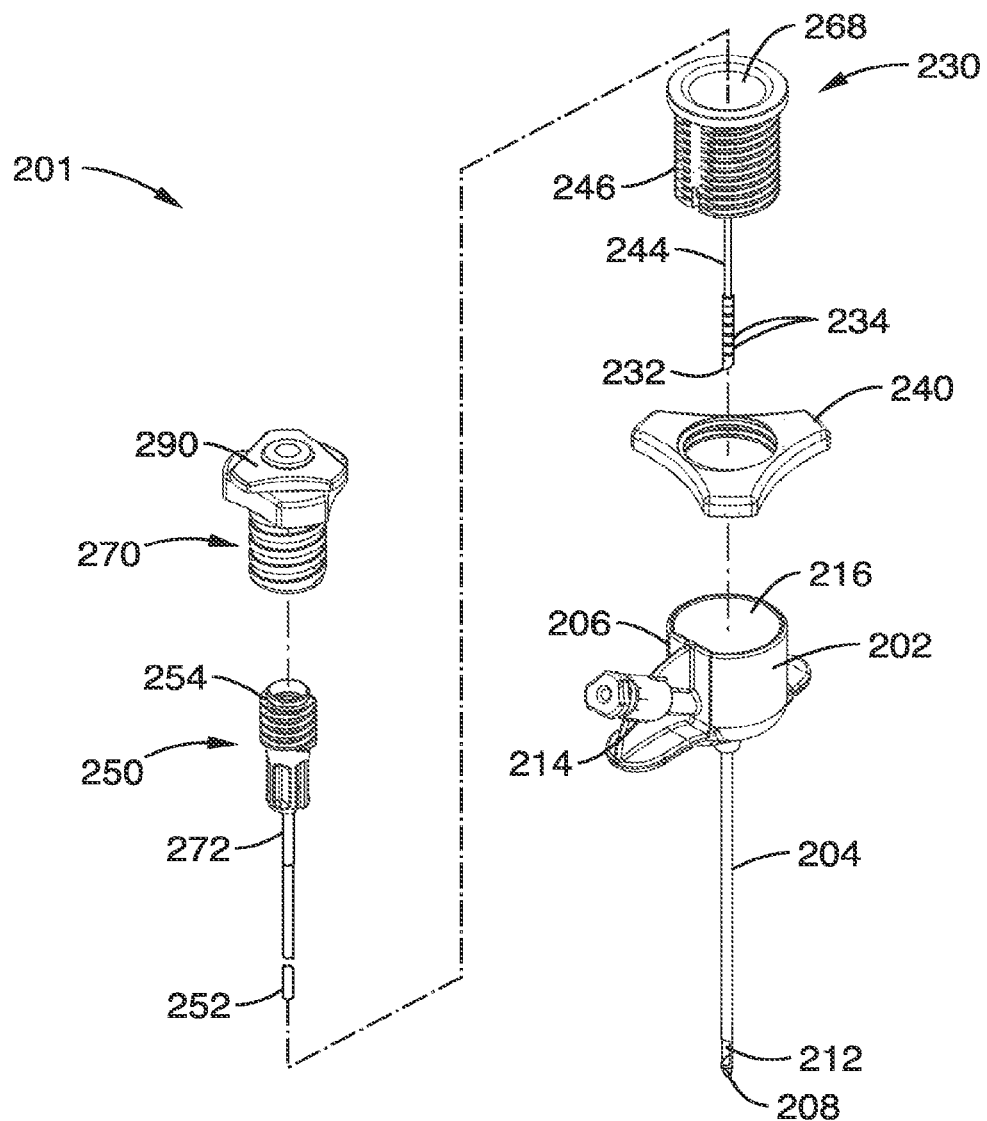
FIG. 9 is an exploded view of the system of FIG. 8.

FIG. 9 illustrates an exploded view of system 201 prior to delivery within a patient. While it is preferred that the trocar 210 is introduced to a location near the target treatment site as a whole assembly shown in FIG. 8, in one embodiment, the trocar may be introduced to the location by itself, with the additional components being positioned once the trocar 210 is in place. In such a configuration, a stylet (not shown) may be positioned down the central channel 218 of the trocar 204 so as to block the aperture 212 from bone fragments or other tissue matter entering in channel 218. The stylet may have a hard, widened proximal end to allow the trocar 210 to be tapped into place.

The proximal end 206 of trocar housing 202 comprises a centrally-located, counter-bore or recess 216 that is in communication with trocar channel 218. Trocar recess 216 allows placement and reciprocation of curveable cannula 230 within the trocar recess 216 and trocar central channel 218. The curveable cannula 230 may be held in place at a specified location within the trocar recess 216 via a stop nut 240 that is threaded about proximal body 246 of the curveable cannula 230. The curveable cannula 230 also comprises a central recess 268 within proximal body 246 that is centrally aligned with cannula channel 245. Central recess 268 and cannula channel 245 are configured to receive and allow reciprocation of probe 250, which is threaded into drive nut 270. In several embodiments, the drive nut 270 comprises a hardened proximal surface suitable for applying an impact force to advance one or more of the trocar, curveable cannula, or probe through bone.

FIGS. 10A-10E schematically illustrate the system 201 in various stages of deployment. FIGS. 11, 13, 15 and 16 illustrate section views of the proximal end of system 201 through the various stages embodied in FIGS. 10A-E. Correspondingly, FIGS. 12 and 14, illustrate close-up views of the distal end of system 201 through various the stages embodied in FIGS. 10A-10E.

Figure 11:
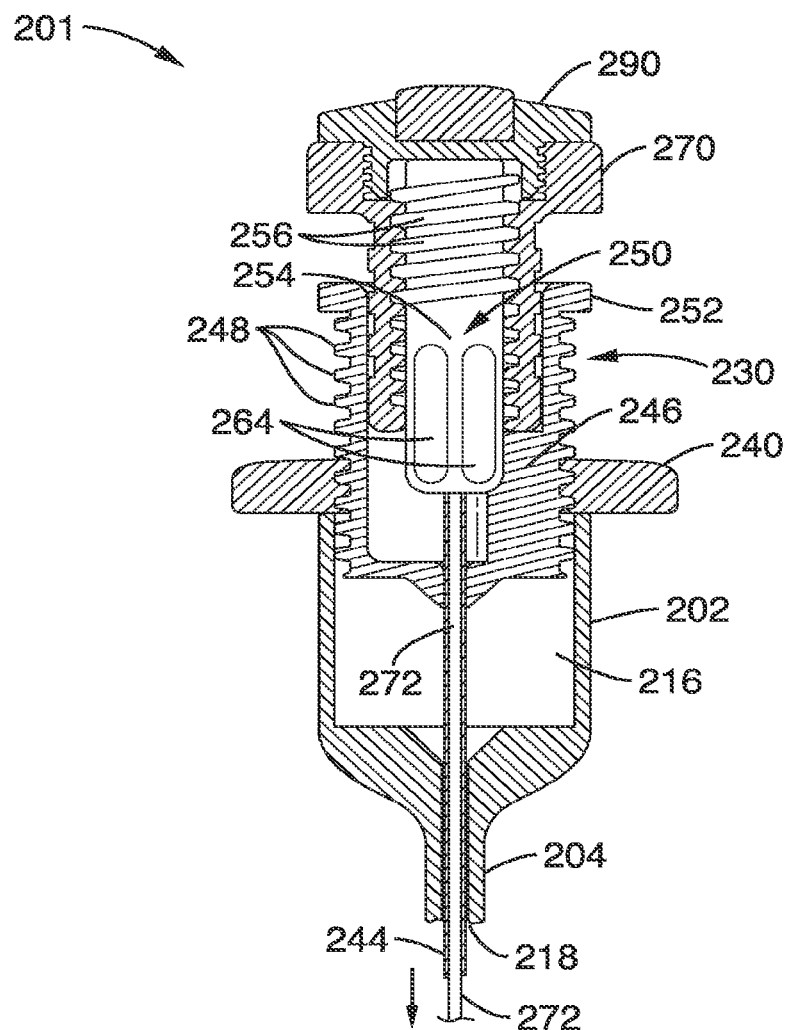
FIG. 11 is a section view of the proximal end of the system of FIG. 8 during introduction of the system into the body.
Figure 12:
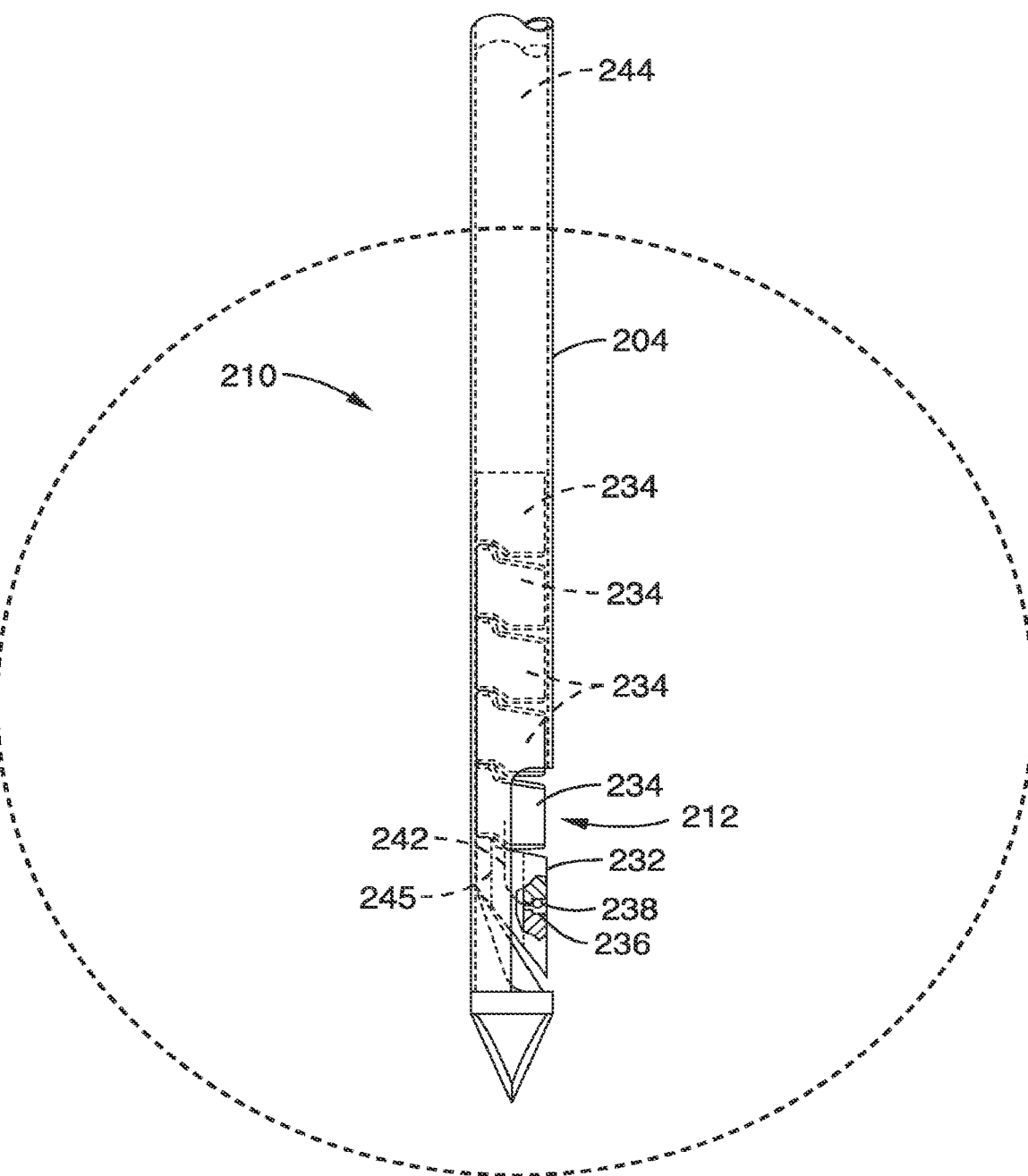
FIG. 12 is a side view of the distal end of the system of FIG. 8 during introduction of the system into the body.

FIG. 11 illustrates a sectional view of the proximal end of system 201 in an un-deployed state prior to or during insertion of the trocar 210 to the desired treatment location in the patient. For delivery into a vertebral body 120 (e.g. to access the BVN), the trocar 210 may be delivered through pedicle 138 via channel 140 (as shown in FIG. 3). Channel 140 may be a pre-drilled hole, or may be generated by insertion of the sharpened tip 208 into the bone. To facilitate insertion, the proximal surface 292 of cap 290 of the drive nut 270 may comprise a rigid material (e.g. stainless steel or the like) so that a mallet or similar device may strike surface 292 to tap the trocar body 204 into place.

During insertion of the trocar 210, the stop nut 240 may be threaded distally along external threads 248 of the proximal body 246 of the curveable cannula 230 to restrict motion of the cannula 230 distally down trocar recess 216. This restrained motion may keep the distal end 232 of the cannula 230 from prematurely deploying while the trocar 210 is being delivered.

In accordance with several embodiments, the distal end of the curveable cannula is deformable so as to be delivered in a straight configuration through the trocar and deployed in a curved configuration outward from the radial opening at an angle with respect to the central axis. As shown in FIG. 12, the distal tip 233 of the curveable cannula 230 comprises a series of tubular mating links 234 each having a central bore to provide a continuous cannula channel 245 along with cannula tube 244. The mating links 234 may be configured to cause the distal tip 233 of the curveable cannula to articulate into a curved shape and be steerable. Cannula channel 245 extends from central cannula recess 268 of the proximal body 246 to the distal link 232 at tip 233. Distal link 232 comprises a beveled tip 233 to facilitate the curveable cannula 230 generating a path through bone as detailed below. Distal link 232 may also comprise a hard material (e.g. stainless steel, thermoplastic, or the like) to provide a rigid leading edge for the curveable cannula 230.

The mating links 234 are held together with a cord 242 that runs from the proximal body 246 of the curveable cannula 230, and terminates at an aperture 236 in the distal link 232. In some embodiments, the distal end of cord 242 terminates at a ball 238 that is disposed in a counter-bore, countersink, or like retaining surface of the aperture 236 to retain the cord within the distal link 232.

Figures 10A, 10B:
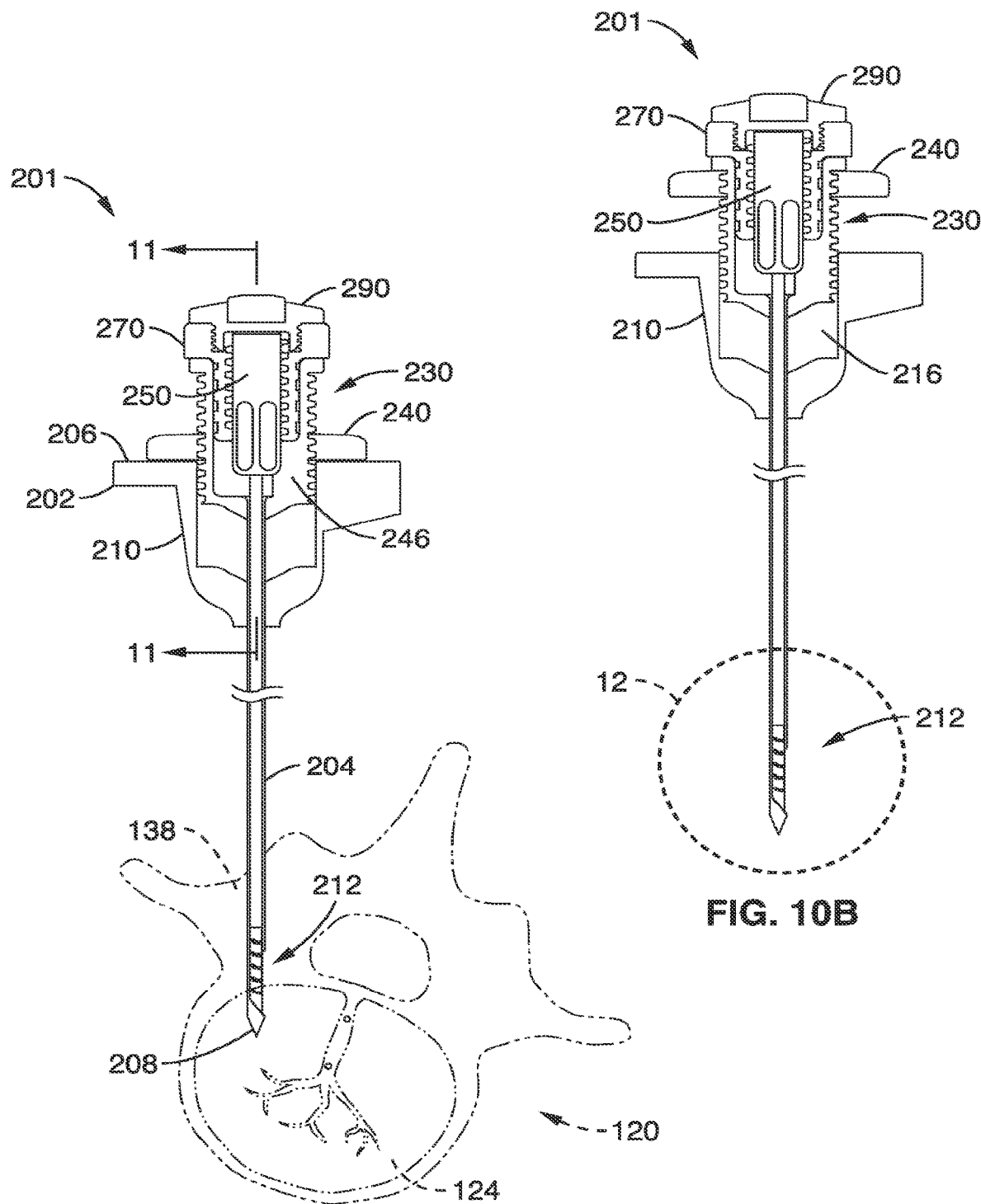
FIG. 10A-10E show schematic diagrams of the system of FIG. 8 at various stages of deployment during a procedure.
Figures 10C, 10D:
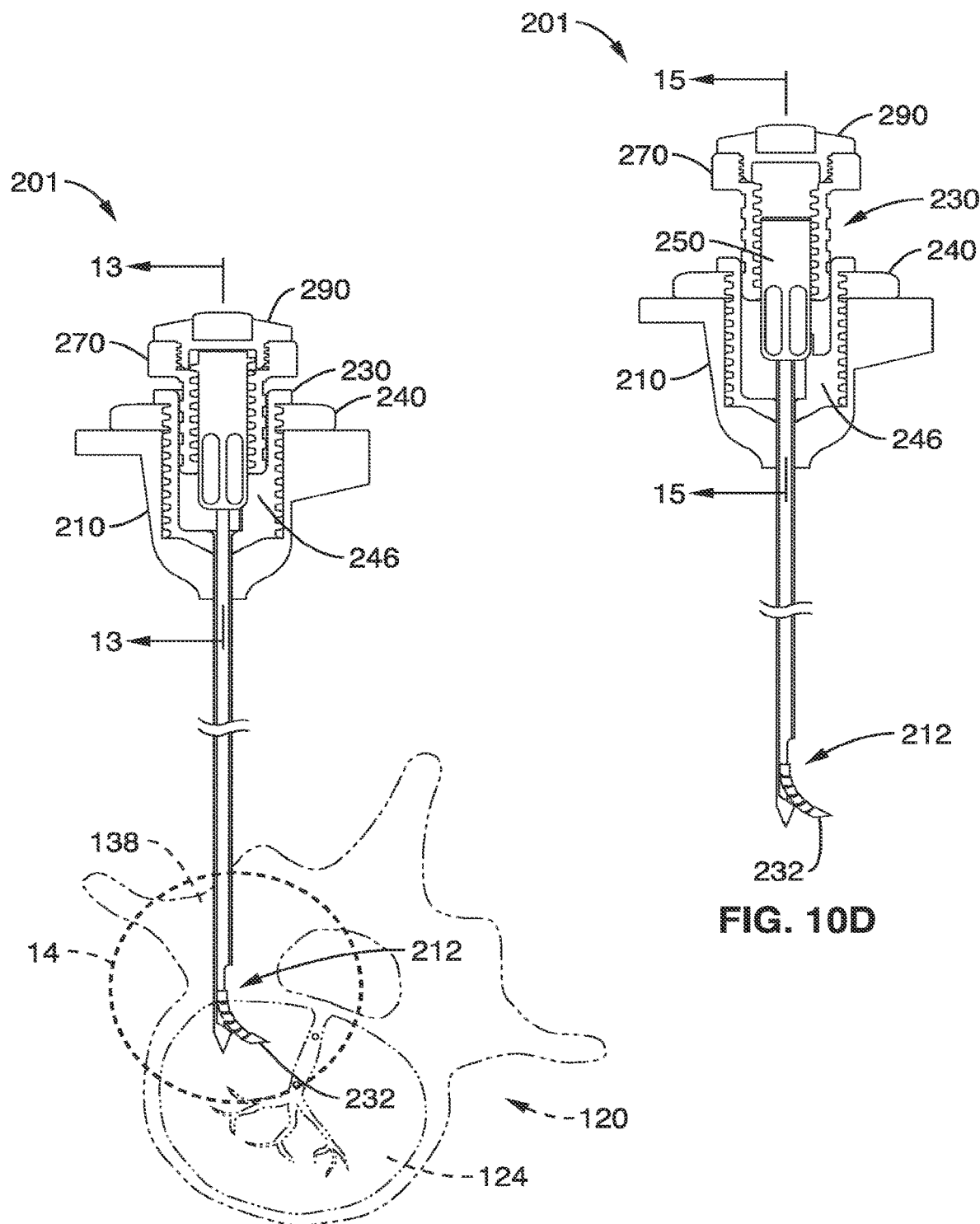
Figure 10E:
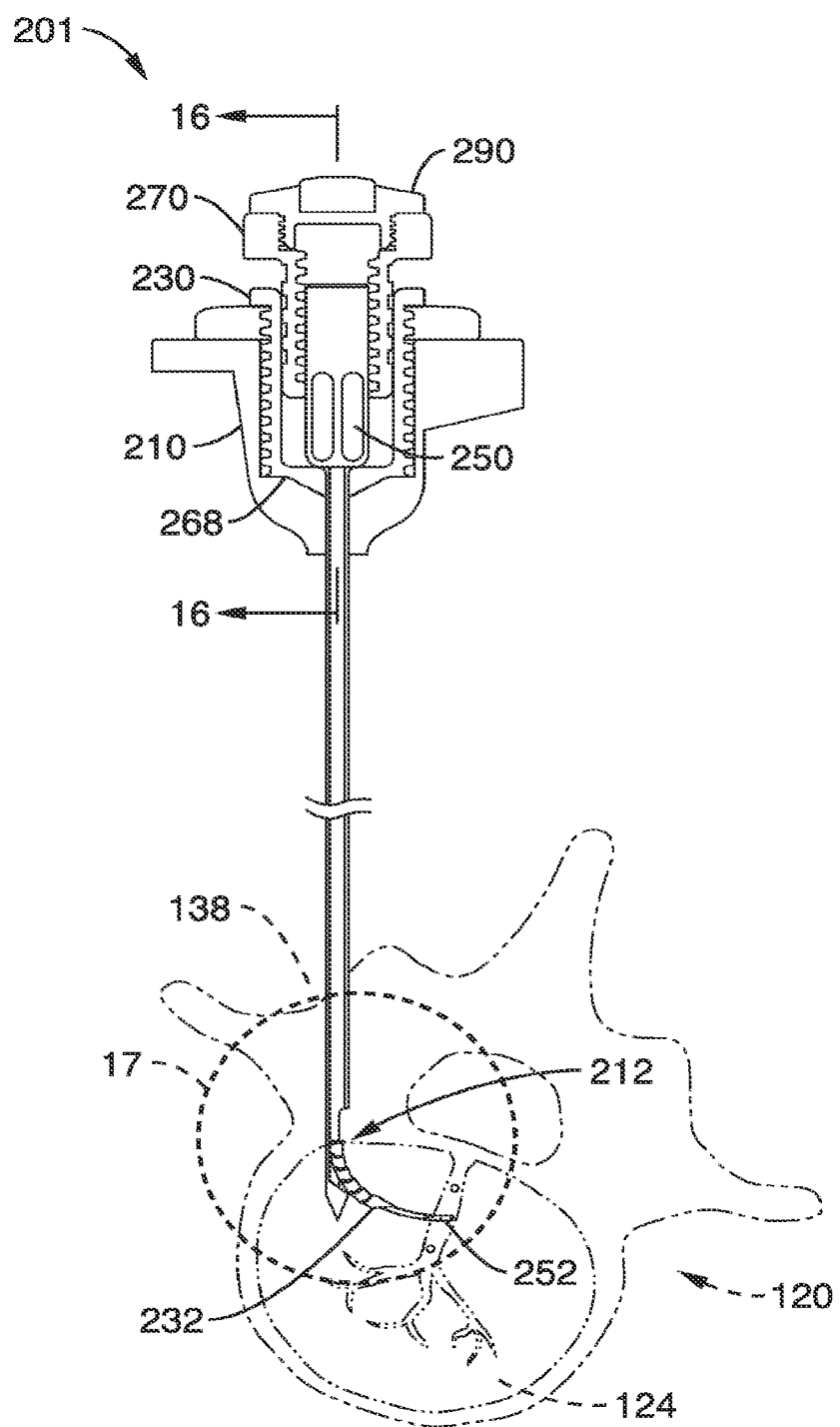

Referring now to FIG. 10B, once the trocar 210 is in place, stop nut 240 is threaded proximally along external threads 248 of the proximal end 246 of the curveable cannula 230 to allow motion of the cannula 230 distally downward in recess 214.

Figure 13:
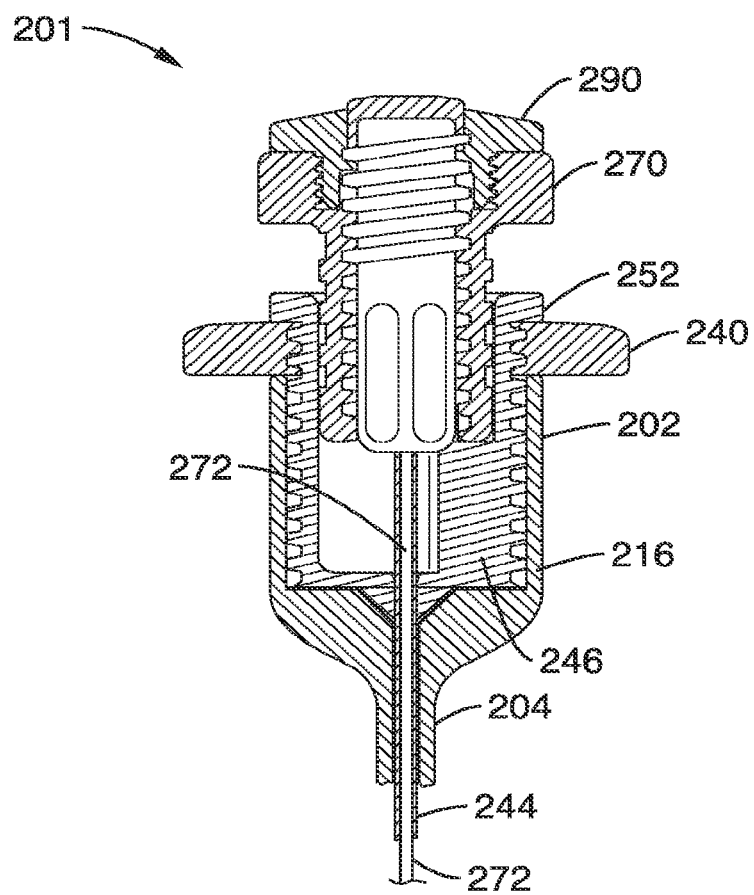
FIG. 13 is a section view of the proximal end of the system of FIG. 8 after deploying the curveable cannula into the body.
Figure 14:
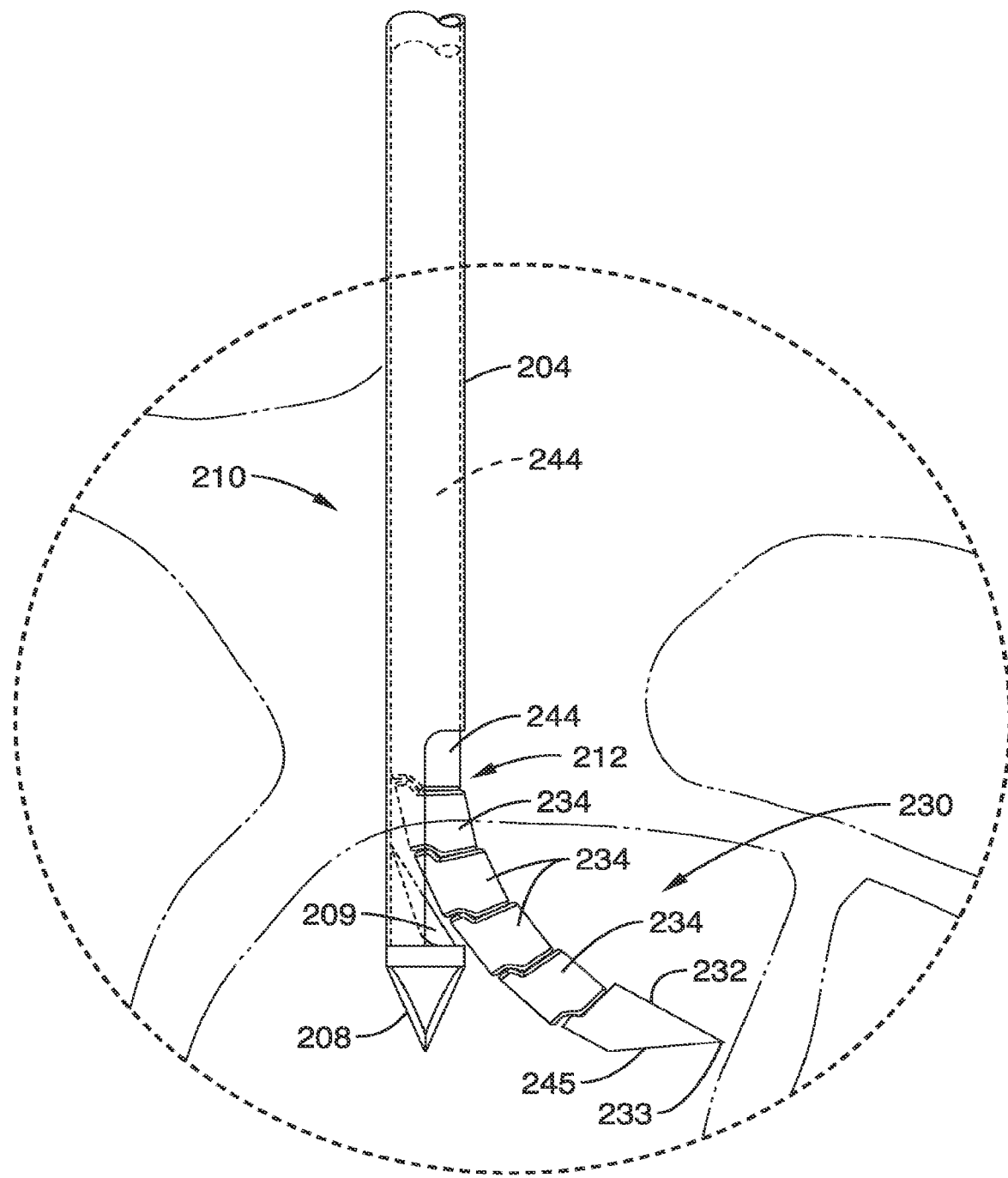
FIG. 14 is a side view of the distal end of the system of FIG. 8 after deploying the curveable cannula into the body.

The proximal body 246 of curveable cannula 230 may then be deployed downward within trocar recess 216, as shown in section view in FIG. 13. As there may be resistance from the bony mass of the vertebral body (or other bony mass), the cannula 230 may be tapped downward by striking the proximal surface of cap 290 (e.g. with a mallet or the like) while holding the trocar at housing 202. In several embodiments, the motion of proximal body 246 pushes tube 244 distally within channel 218 of the trocar body 204. This motion forces the leading edge 232 and trailing mating links 234 out of the radial window 212 in tube 204, as shown in FIG. 14. The distal end of opening or window 212 comprises a ramp 209 to facilitate the leading edge 232 out the window 212 at the proper angle with respect to the trocar tube 204 central axis, and without catching or getting stuck at the distal end of the trocar 210.

In some embodiments, a pull cord 242 is coupled to the distal tip of the curveable cannula 230, the pull cord extending to the proximal end of the trocar 210. In addition to the ramp 209, the curved path of the distal tip 233 is facilitated by tension provided by cord 242, which forces the mating links 232, 234 to arch upon the applied tension. The pull cord may be configured to apply a tensile force to the distal end of the curveable cannula to bias the curveable cannula into a curved configuration. In some embodiments, the cord 242 is coupled to male-threaded dial 212 (see FIG. 8) to act as a pull cord to apply said tension. The dial 212 may be turned clockwise or counterclockwise within internal-threaded arm 214 to increase or relieve the tension on the cord 242, thereby providing steering of the distal tip 233 while the curveable cannula 230 is advanced down trocar body 204 and out window 212 (e.g. increased tension provides a sharper radius, decreased tension provides a more relaxed or no radius.) The tensile force applied to the distal tip of the curveable cannula 230 may be controlled from the proximal end of the trocar to steer the curveable cannula 230 along a desired path.

Alternatively, cord 242 may comprise a memory material such as a Nitinol wire that fastens the tube 244 and links 232, 234 in a preformed curved-shape. The cord 246 in this configuration stretches to allow the curveable cannula 230 to be delivered into and stowed in a linear form within channel 218, and retracts when not restrained in channel 218 to drive a curved path when exiting window 212.

As shown in FIGS. 13 and 14, the curveable cannula 230 is fully deployed, with the proximal end 246 disposed at the bottom of recess 216, and the distal tip 233 in a deployed orientation forming a curved path (along with trailing links 234) through the bone at the treatment site. In this configuration, the probe 250 is restrained from axial motion (in the distal direction) with respect to the curved cannula 230, because it is threaded inside a threaded recess portion of drive nut 270, which is restrained from distal motion by stop 258 in the proximal end 246.

Figure 15:
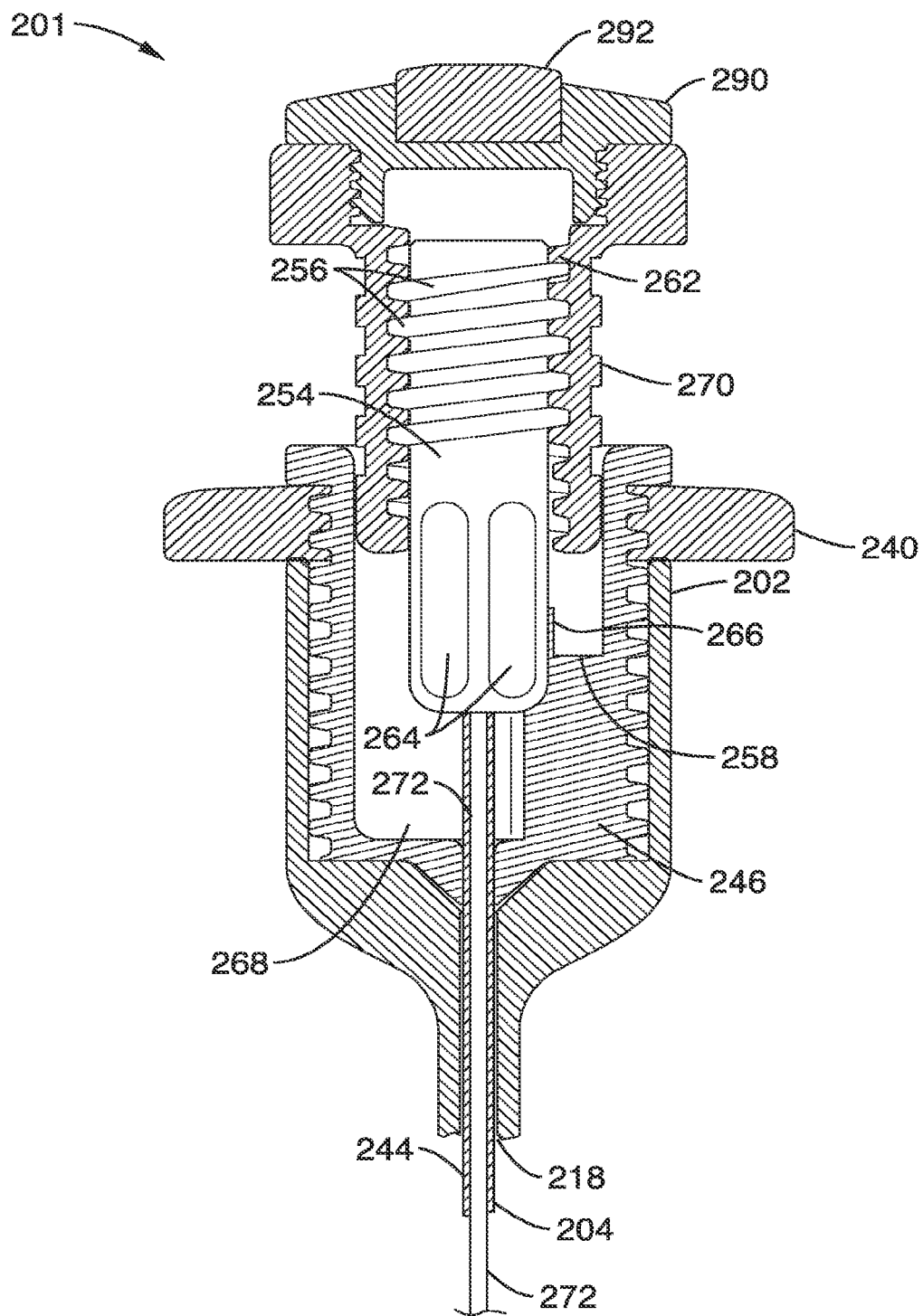
FIG. 15 is a section view of the proximal end of the system of FIG. 8 with the drive nut retracted.

As shown in FIG. 15, the drive nut 270 may be raised (proximally advanced out of cavity 268) with respect to the curveable cannula 230 and probe proximal body 254 by rotating the drive nut 270. The proximal body 254 of the probe 250 comprises a male thread 256 that mates with the female internal threads 262 in a distal recess of the drive nut 270. The thread pattern 256/262 may be opposite of the thread pattern between the stop nut 240 and proximal end 246 of the curveable cannula 230 (e.g. right-handed thread vs. left-handed thread), so that rotation of the drive nut 270 does not result in rotation of the curveable cannula 230.

Furthermore, the proximal end 254 of the probe 250 comprises a plurality of vertical grooves 264, at least one of which interfaces with key 266 of the curveable cannula 230. This interface only allows axial motion of the proximal body 264 with the curveable cannula 230, and restricts rotation of the proximal body 264 with the curveable cannula 230. Thus, rotation of the drive nut 270 may only result in proximal translation of the drive nut 270. As seen in FIG. 15, the probe proximal body 254 is now free to move downward in cavity 268.

Figure 16:
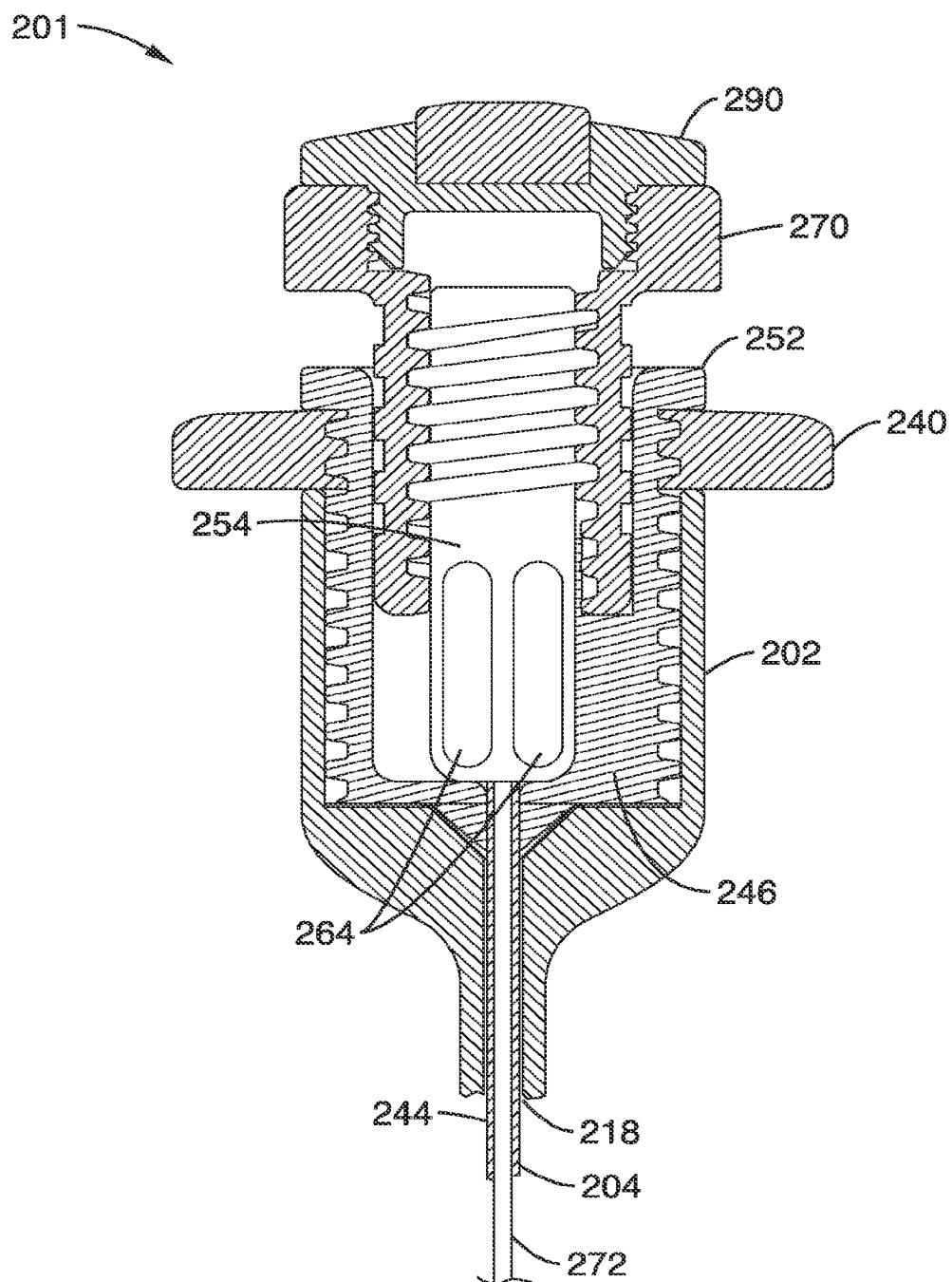
FIG. 16 is a section view of the proximal end of the system of FIG. 8 after deploying the probe into the body.
Figure 17:
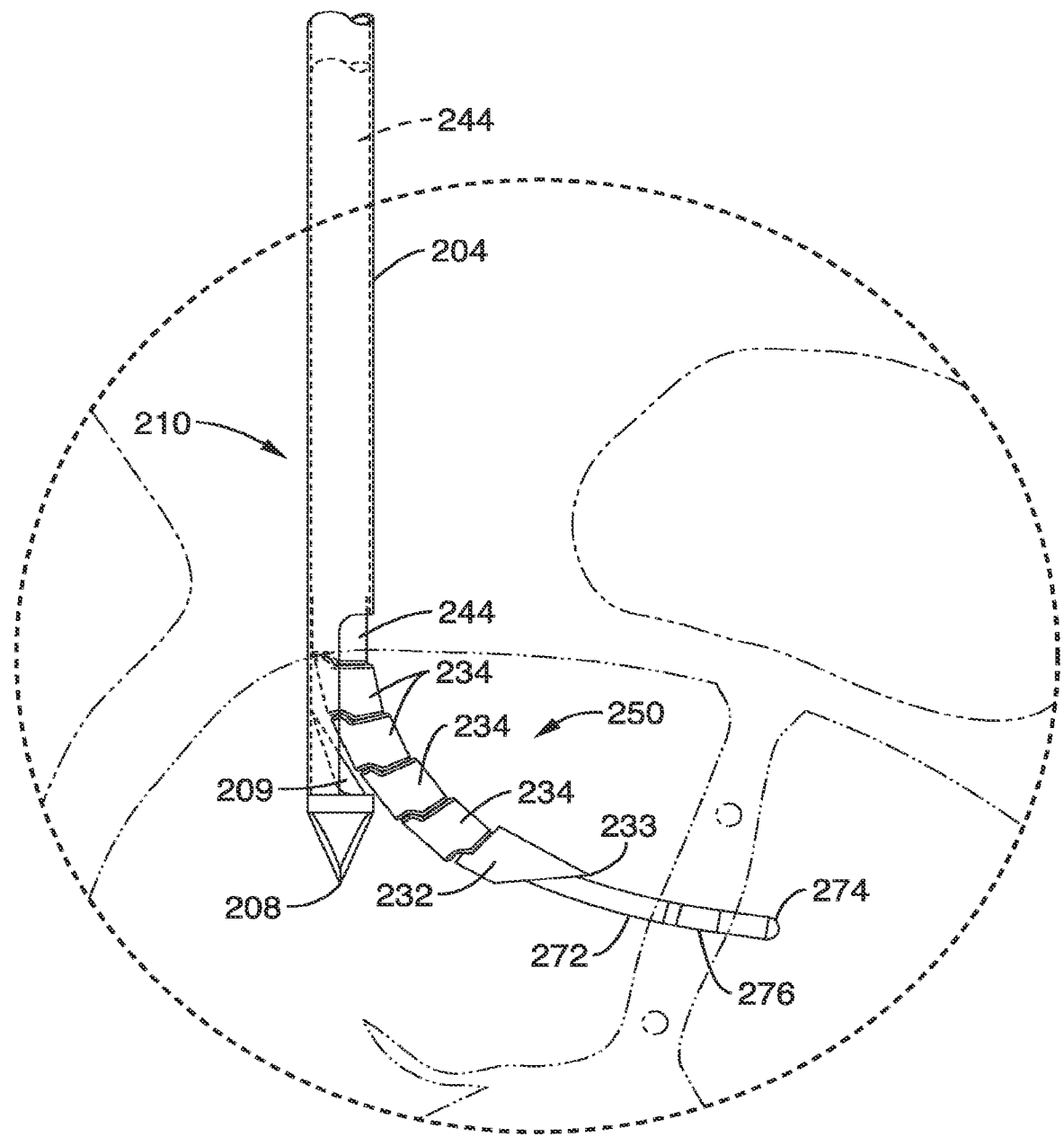
FIG. 17 is a side view of the distal end of the system of FIG. 8 after deploying the probe into the body.

Referring now to FIGS. 16 and 17, the system 201 is shown in a fully deployed state, with the distal shaft of the probe 250 advanced beyond distal end 233 of the curveable cannula central channel 245. In several embodiments, this deployment is achieved by advancing the proximal body 254 within the cavity 268 of the curveable cannula 230. In several embodiments, the proximal body 254 and drive nut 270 are advanced as a unit within cavity 268 (e.g., by tapping the cap 290), thereby providing an impact force to advance the probe tip 274 out of the cannula 230 and through tissue and/or bone to reach the desired treatment or diagnostic location within the body.

In one embodiment, a channeling stylet (such as stylet 90 shown in kit 10 of FIG. 1) may also be used to create a working channel beyond the end of the curved path created by the curveable cannula 230 prior to deploying a probe for treatment or diagnostic purposes.

Once the distal tip 274 of the probe 250 is positioned at the desired location, treatment of the target tissue may be performed. As shown in FIG. 17, probe distal end 274 may comprise a first electrode 274 configured to deliver a therapeutic amount of RF energy to the target location. In the configuration shown in FIG. 17, the probe 250 comprises a bipolar probe with a return electrode 276, however, in various embodiments, the probe 250 comprises any treatment instrument or device described herein.

Cap 290 may further be configured to include (e.g. a self contained unit) a power source (e.g. battery) and receptacles (not shown) to couple to the probe 250, thereby supplying the energy to deliver a therapeutic level of energy to the tissue. In this configuration, the cap 290 may have sufficient power to deliver one or more metered doses of energy specifically measured to modulate (e.g., denervate) at least a portion of the BVN of a vertebral body.

The cap 290 may be threaded (or otherwise releasable coupled) into drive nut 270 to be interchangeable depending on the application or step of the procedure. For example, a cap 290 having a reinforced/hardened surface 292 used for driving the system 201 into the bone may be replaced by another cap having couplings (not shown) for probe 250, an internal power supply (not shown), or couplings for an external power supply/controller (not shown) for delivering energy for treatment and/or diagnosis of a region of tissue. For embodiments wherein a fluid and/or agent is delivered to the target tissue, the cap 290 may be configured to facilitate delivery of the fluid through a probe having one or more fluid delivery channels. In some embodiments, the interchangeable cap 290 is configured to provide access to the probe 250 for providing a therapeutic energy.

FIGS. 18A and 18B are side views of the distal end of the system 201 with the curveable cannula 230 in a stowed and deployed position respectively. The distal link 232 and trailing links 234 are configured to have mating/interlocking surfaces that allow the distal end of the cannula to curve in one direction. The more distal link of a mating pair will have an extension 235 that mates with a correspond depression 237 in the link proximal to it. This allows the links to rotate with respect to each other to create a curved distal end as shown in FIG. 18B.

Figure 19A:
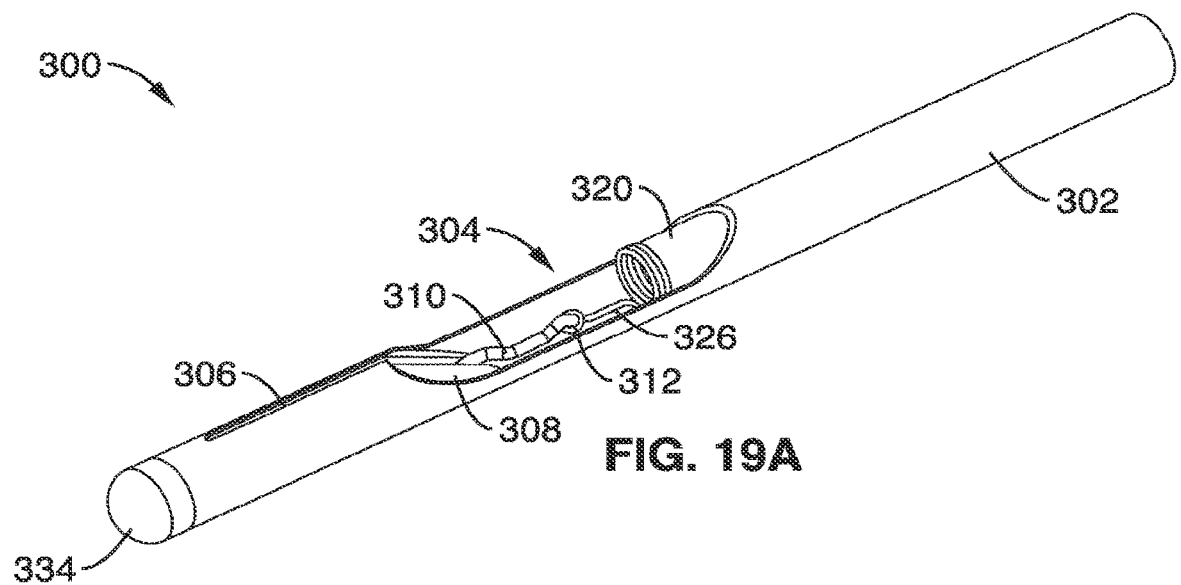
FIG. 19A illustrates a perspective view of an alternative system for generating a curved path in bone.
Figure 19B:
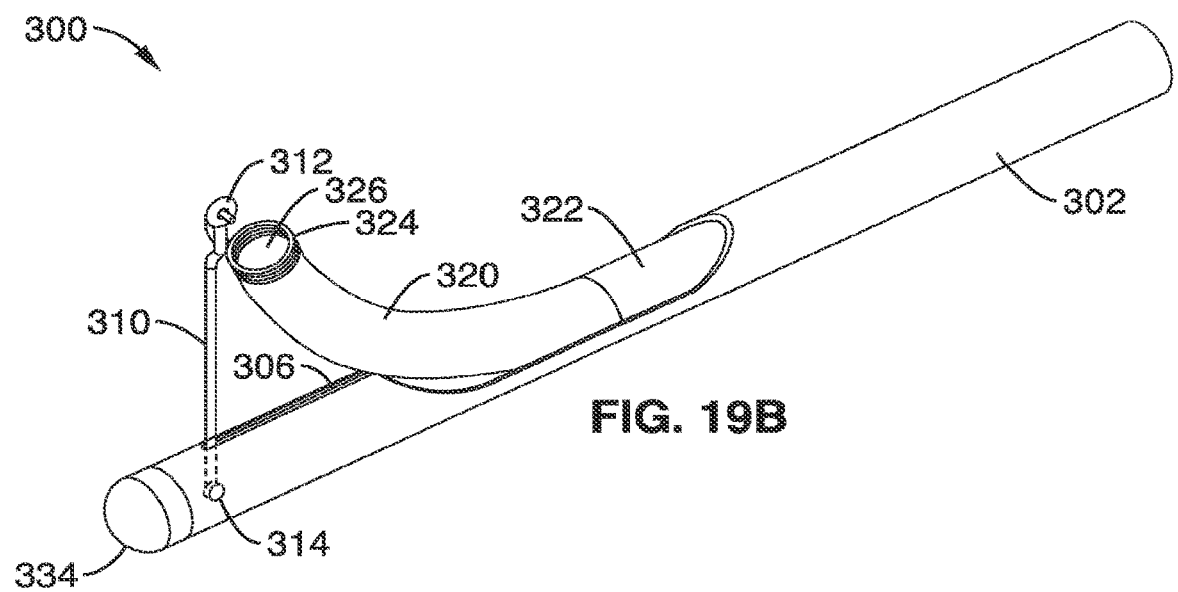
FIG. 19B illustrates the system of FIG. 19A in a deployed configuration.
Figure 20:
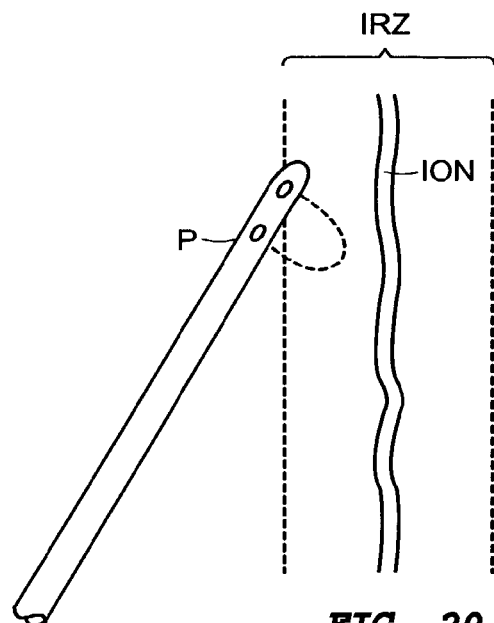
FIGS. 20 and 21 depict the treatment of the BVN with a bipolar electrode.
Figure 21:
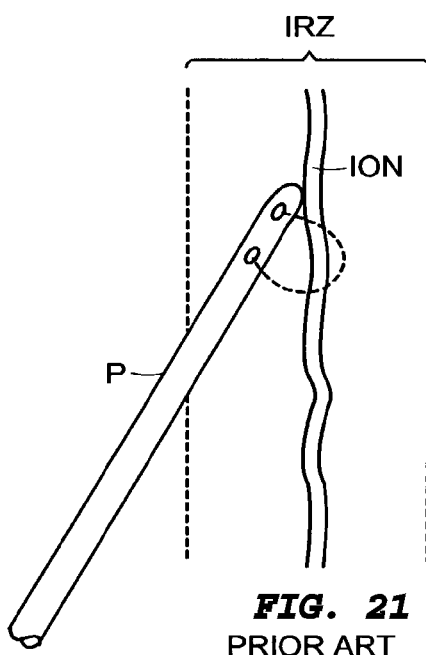
Figure 22:
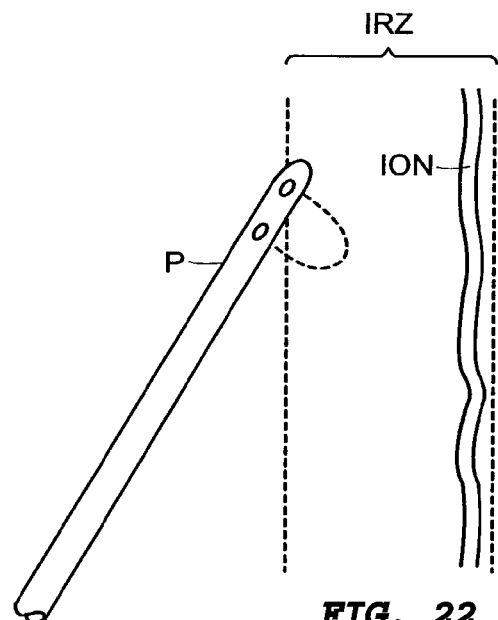
FIGS. 22 and 23 depict the difficulty of treating a BVN with a bipolar electrode.
Figure 23:
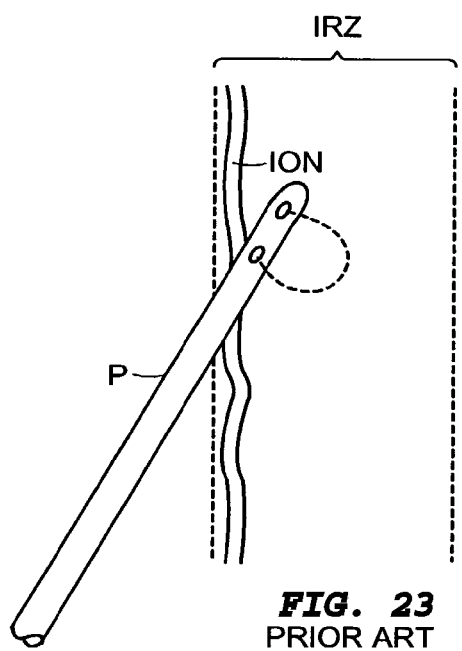
Figure 24:
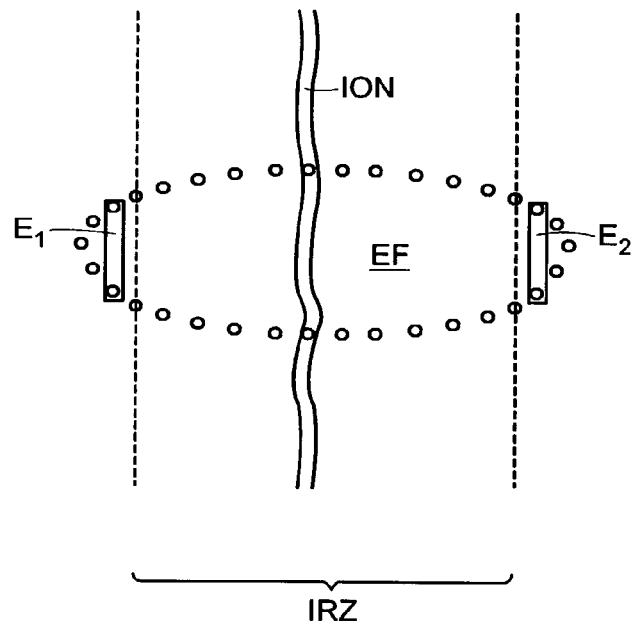
FIGS. 24 and 25, respectively, depict top views of an electric field and a heating zone produced within bone tissue.
Figure 25:
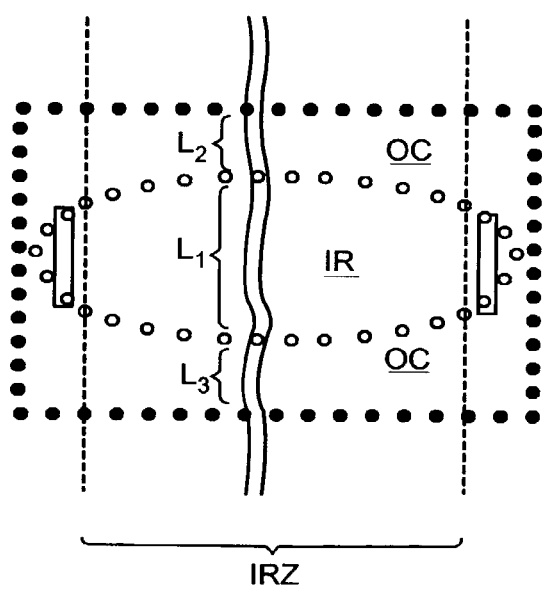
Figure 26:
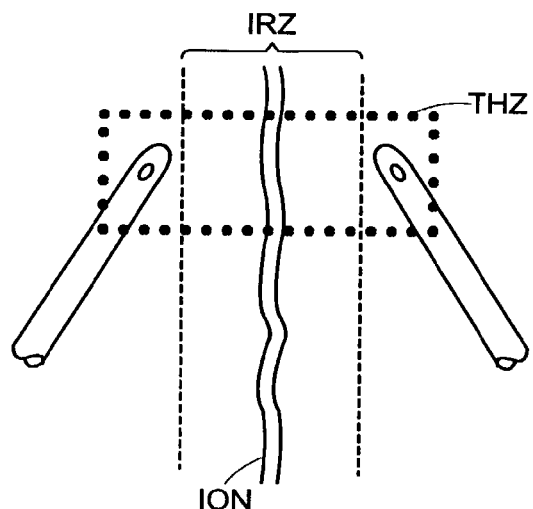
FIGS. 26-28 depict the treatment of the BVN with a bipolar electrode apparatus.
Figure 27:
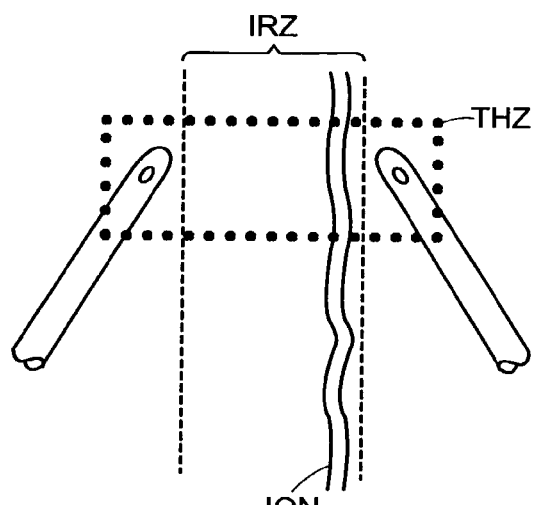
Figure 28:
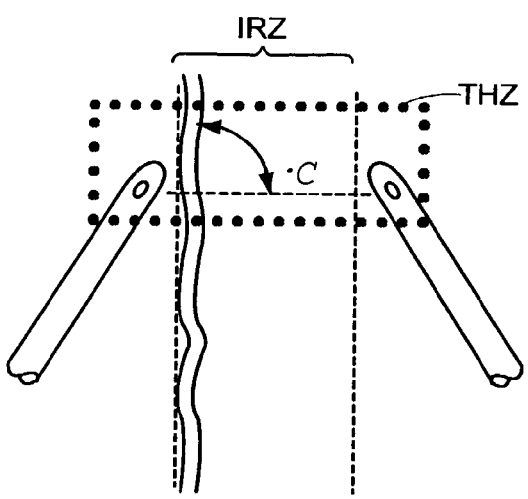

FIGS. 19A and 19B illustrate an alternative system 300 for generating a curved channel through bone. System 300 comprises a tubular trocar body 302, the proximal end (not shown) of which may comprise a portion or all of any of the previously described proximal ends for devices 10, 200, or 201 disclosed herein. The distal tip 334 comprises a leading edge surface for advancing through bone, and a radial or lateral window 304 allowing access to the central channel of the trocar body 302. The window 304 is positioned a short distance proximal to the distal tip 334.

A curveable cannula 322 is positioned in the trocar 302, the curveable cannula 322 having a distal end 324 coupled via linkage 326 to a pivotable arm 310. The proximal end (not shown) of the curveable cannula may comprise a portion or all of any of the previously described proximal ends for devices 10, 200, or 201 disclosed herein. The pivotable arm 310 has a first end pivotably coupled at joint 314 at a location at or near the distal tip 334 of the trocar 334. In a stowed configuration (illustrated in FIG. 19A), the pivotable arm is configured to lay axially in the trocar 302 within slot 306 that runs from pivot 314 proximally to the radial opening or window 304. The proximal (when stowed) end 312 of the arm 310 is coupled to the linkage 326.

As shown in FIG. 19B, the cannula 322 may be advanced laterally outward from window 304 by simply advancing the cannula 322 distally down the trocar 302. The pivotable arm 310 constrains the motion of the curveable end 320 of the cannula to a curved path of specified radius (determined by the length of arm 310. Once the pivotable arm has reached full rotation (shown approximately 90 degrees in FIG. 19B, however such angle may be specified to be any desired amount), the cannula end 320 has created a curved path outward from the trocar toward the desired treatment site. A probe, stylet or similar device (such as curved stylet 60, channeling stylet 90, or probe 100 of FIG. 1) may be positioned at the opening of the distal end 320 to facilitate generating the curved bore without allowing tissue or bone to enter the cannula. The probe or treatment and/or diagnostic device may then be routed through the cannula end 320 to a region of tissue or bone that is off-axis from the trocar body 302.

According to several embodiments, the above systems 201, 300 may be provided as a kit of instruments to treat different regions of the body. For example, the location, orientation and angle of the treatment device with respect to the trocar may be varied by providing a set of instruments at varying increments. This may be achieved by varying the curvature in the curveable cannula (230, 320). The curvature may be varied by varying the radius of curvature, the insertion depth (shaft length and tip length, and/or the final exit angle with respect to the trocar central bore. Thus, the physician may select a different kit for treating a lumber spine segment as opposed to a sacral or cervical spine segment, as the anatomy will dictate the path that needs to be channeled.

According to several embodiments, each of the instruments in the systems 10, 200, 201, and 300 detailed above may have any length, shape, or diameter desired or required to provide access to the treatment and/or diagnostic region (e.g. intraosseous nerve or basivertebral nerve trunk) thereby facilitating effective treatment/diagnostic of the target region. For example, the size of the intraosseous nerve to be treated, the size of the passageway in the bone (e.g. pedicle 138) for accessing the intraosseous nerve, and the location of the bone, and thus the intraosseous nerve, are factors that that may assist in determining the desired size and shape of the individual instruments. In several embodiments, the treatment device (e.g., RF probe) has a diameter between 1 mm and 5 mm (e.g., between 1 mm and 3 mm, between 2 mm and 4 mm, between 3 mm and 5 mm, 1 mm, 2 mm, 3 mm, 4 mm, 5 mm, or any diameter between the recited ranges).

The systems 10, 200, 201 and 300 described above may be used with a number of different treatment modalities for therapeutic treatment of the target region, which may be spinal or non-spinal. For example, in one embodiment, it is desirable to operate the treatment devices or probes in systems 100, 200, 201 and 300 in a manner that denervates (e.g., ablates) the tissue of the target region (e.g. BVN) to produce heat as described in U.S. Pat. No. 6,699,242, herein incorporated by reference in its entirety.

In another embodiment, the treatment device is configured to deliver therapeutic treatment that is targeted to block nerve conduction without ablating the nerve. For example, thermal treatment (e.g., a thermal energy dose) can be delivered to the nerve (e.g. via thermal therapy, agent or the like) that results in denervation of the BVN without necrosis of tissue. This non-ablative treatment may be achieved via delivery of a lesser amount of energy or agent to the tissue site (either in the form of less exposure time, concentration, intensity, thermal dose, etc.) than is required for ablation, but an amount sufficient to achieve some amount of temporary or permanent denervation.

In accordance with several embodiments, the treatment devices (e.g., probes) described herein may comprise non-therapy devices or elements, such as diagnostic devices (e.g.

ultrasound, cameras, sensors, or the like) to diagnose a region of tissue independent of or in connection with treatment of the region of tissue.

In several embodiments, individual elements of any of the systems 10, 200, 201, and 300 detailed above may be used interchangeably where applicable. For example, the curved stylet 60 shown in systems 10 and 200 may be temporarily implemented in place of the probe of systems 201 and 300 to provide additional curving bias to the curveable cannula (230, 320) while the cannula is being driven into the bone. Furthermore, the channeling stylet 90 may be used to further generate a channel beyond the curved path provided by the curveable cannula (230, 320).

FIGS. 25-51 illustrate additional embodiments of systems, devices and methods for modulation of nerves (e.g., intraosseous nerves or basivertebral nerves) within bone (e.g., vertebral bodies of the spine), as well as features, elements, structures, and method steps that may be incorporated into the embodiments described above.

As used herein, the "resistive heating zone," in addition to its ordinary meaning, is the zone of bone tissue that is resistively heated due to an energy loss incurred by current travelling directly through the bone tissue. Resistive heating, "joule" heating and "near-field" heating may be used interchangeably herein. The "conductive heating zone," in addition to its ordinary meaning, is the zone of bone tissue that is heated due to the conduction of heat from an adjacent resistive heating zone. The total heating zone (THZ) in a bone tissue includes both the resistive heating zone and the conductive heating zone. The border between the conductive and resistive heating zones is defined by the locations where the strength of the electric field is 10% of the maximum strength of the electric field between the electrodes. As used herein, the heating zones encompass the volume of bone tissue heated to at least 42° C. by embodiments described herein. As used herein, the "first and second sides" of a vertebral body are the lateral-lateral sides intersected by the BVN. The modulation of the ION may be carried out by resistive heating, conductive heating, or by hybrid heating.

In some embodiments, the therapeutic heating of the ION is provided by both resistive and conductive heating. In some embodiments thereof, as in FIG. 25, the electrodes are placed such that the ION passes through resistive heating zone IR, so that length $L_2$ of the ION is therapeutically heated by bone tissue in the resistive heating zone IR and lengths $L_2$ and $L_3$ of the ION are therapeutically heated by the bone tissue in the conductive heating zone OC.

In embodiments wherein the therapeutic heating of the ION is provided substantially by both resistive and conductive heating, it may be preferred that the length $L_1$ of the ION treated by resistive heating comprise at least 25% or at least 50% of the total therapeutically treated length of ION. In other embodiments, the length may be in the range of 10-25% of the treated length of ION, in the range of 40-60% of the treated length of ION, in the range of 50-70% of ION, greater than 70% of the treated length of ION, or overlapping ranges thereof. In several embodiments, the peak temperature in the resistive heating zone IR is between 40° C. and 60° C. greater than the peak temperature in the conductive heating zone OC. In some embodiments, the peak temperature in the resistive heating zone IR is between about 20° C. and 40° C. greater than the peak temperature in the conductive heating zone, between about 10° C. and 20° C. greater than the peak temperature in the conductive heating zone OC, between about 5° C. and 10° C. greater than the peak temperature in the conductive heating zone OC, between 0° C. and 5° C. greater than the peak temperature in the conductive heating zone OC in the range of 2° C. and 5° C. greater than the temperature in the conductive heating zone OC, or overlapping ranges thereof. In some embodiments, the peak temperature in the resistive heating zone IR is no more than 15° C. greater than the peak temperature in the conductive heating zone OC, no more than 10° C. greater than the peak temperature in the conductive heating zone OC, or no more than 5° C. greater than the peak temperature in the conductive heating zone OC.

Figure 29A:
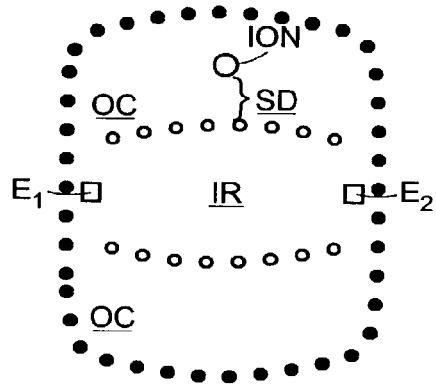
FIGS. 29A and 29B disclose anterior and upper cross-sectional views of a straddled ION that extends in a plane above the electrodes but within the total heating zone.
Figure 29B:
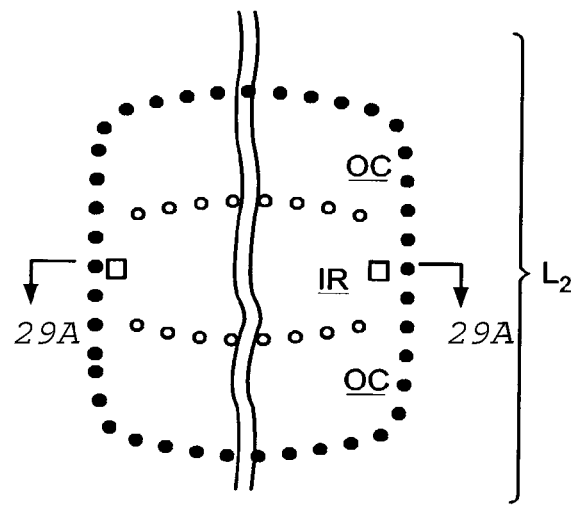
Figure 30:
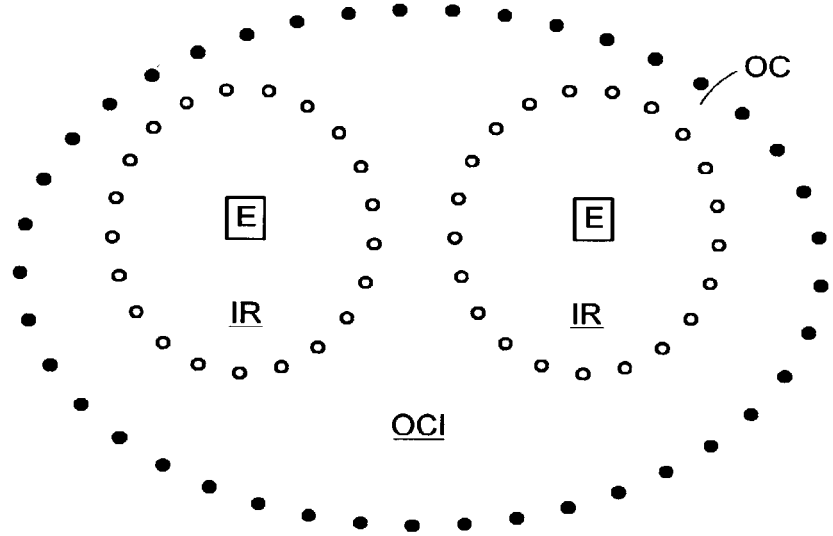
FIG. 30 is a cross-sectional anterior view of an embodiment in which the total heating zone has dumb-bell type resistive heating zones.

Now referring to FIGS. 29A and 29B, in some embodiments, the therapeutic heating of the ION is provided essentially by the conductive heating zone OC. This may occur when the ION is in fact located substantially far from the middle of the ION residence zone IRZ. In such an instance, the electrodes are placed such that the ION passes only through the conductive heating zone, so that length $L_2$ of the ION is therapeutically heated by bone tissue in the conductive heating zone OC.

In some embodiments thereof, it may be desired that the separation distance (SD) between the ION and the resistive heating zone IR be no more than 1 cm. This is desired because the closer the ION is to the resistive heating zone, the higher the temperature experienced by the ION length $L_2$. In some embodiments, the separation distance is no more than 0.5 cm or no more than 0.2 cm. In some embodiments, the SD is between 1 cm and 2 cm, between 0.75 and 1 cm, between 0.5 and 0.75 cm, between 0.3 cm and 0.6 cm, between 0.1 cm and 0.3 cm, between 0.02 cm to about 0.2 cm, or overlapping ranges thereof.

In some embodiments, as in FIGS. 29A and 29B, the electric field is sufficiently strong to be located substantially continuously between the two electrodes. This typically occurs when the electrodes are very close together (i.e., no more than 5 mm, no more than 4 mm, no more than 3 mm, no more than 2 mm apart). In other embodiments, however, as in FIG. 30, the electric field is relatively weak and so resides substantially only in the vicinity of the two electrodes. In such cases, and now referring to FIG. 30, inward energy flow from the resistive heating zone IR conductively heats the intermediate area of the conductive heating zone OCI. In several embodiments, the peak temperature in the resistive heating zone IR is no more than 15° C. greater than the peak temperature in the intermediate conductive heating zone OCI, no more than 10° C. greater than the peak temperature in the intermediate conductive heating zone OCI, or no more than 5° C. greater than the peak temperature in the intermediate conductive heating zone OCI.

In several embodiments, methods are carried out via a dual probe system. In particular, embodiments of the dual probe system comprise an energy delivery device comprising a first probe having an active electrode and a second probe having a return electrode. Now referring to FIG. 31, this dual probe embodiment can allow the surgeon to approach the BVN from separate sides of the vertebral body to easily straddle the IRZ with the electrodes. With such a device, the surgeon can place the first probe 601 having an active electrode 603 on a first side of the vertebral body and the second probe 611 having a return electrode 613 on a second side of the vertebral body, and then align the paired electrodes so that their activation produces a total heating zone that straddles the IRZ, and therefore the BVN therein.

In several embodiments, aligning the electrodes of such an apparatus to straddle the ION merely requires advancing the probes into the vertebral body and no complicated navigation is required. According to several embodiments, even if the location of the BVN were precisely known, conventional methods of accessing the BVN require either the BVN to be naturally located within the vertebral body so as to intersect the axis of the pedicle, or require a complicated probe configuration or navigation. In some embodiments, a dual probe approach simply requires substantially linear advance of a pair of substantially straight probes, and is much simpler and/or much more robust than the conventional methods of accessing nerves in bone. For example, the clinician may desirably access the vertebral body through the pedicles with substantially straight probes and have a high confidence that their activation can therapeutically treat the BVN.

In accordance with embodiments of the invention, there is provided a method of therapeutically treating a vertebral body having a BVN, comprising providing an energy device having an active electrode having a first face and a return electrode having a second face into the vertebral body, and placing the active electrode in the vertebral body to face a first direction. The return electrode can then be placed in the vertebral body to face a second direction, with the first and second faces defining an angle $2J$ of no more than 60 degrees. A sufficiently high frequency voltage difference can then be applied between the active and return electrodes to generate a current therebetween to produce a total heating zone to therapeutically heat (e.g., denervate or ablate) the BVN.

In accordance with embodiments of the invention, there is provided a method of therapeutically treating a vertebral body having a BVN comprising: providing an energy device having an active electrode and a return electrode, placing the active and return electrodes in the vertebral body to define an electrode axis, the axis forming an angle C of between 50 and 90 degrees with the BVN, and applying a sufficiently high frequency voltage difference between the active and return electrodes to generate a current therebetween to produce a total heating zone to therapeutically heat (e.g., denervate or ablate) the BVN.

Figure 32:
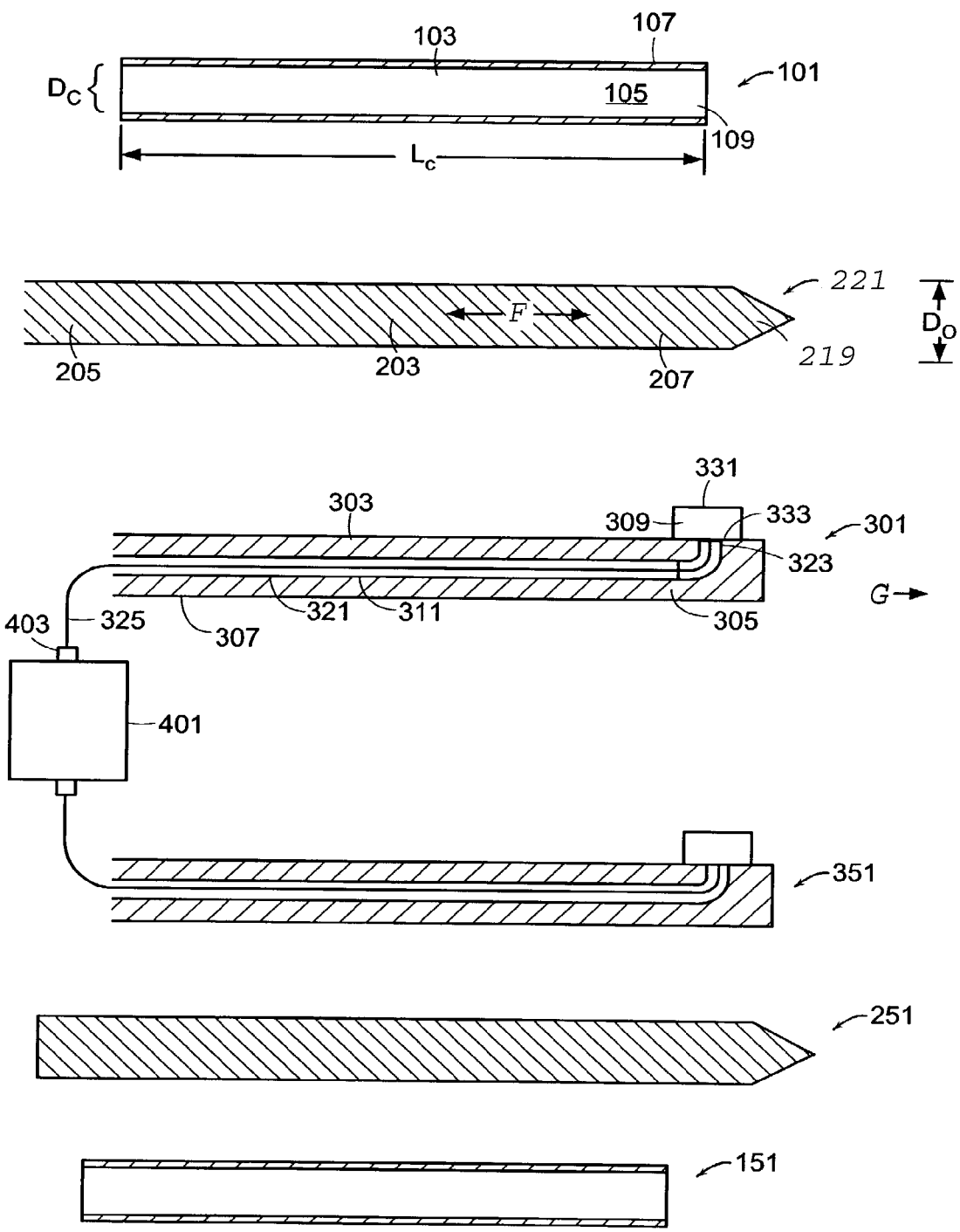
FIG. 32 discloses cross-sections of components of a dual probe apparatus.

Now referring to FIG. 32, there is provided a dual probe apparatus comprising first 101 and second 151 cannulae, first 221 and second 251 stylets, first 301 and second 351 probes, and a power supply 401 in electrical connection with the probes. For simplicity, only a single cannula, stylet and probe will be further described. However, many embodiments use two sets of such devices.

Now referring to FIG. 32, cannula 101 comprises a shaft 103 having a longitudinal bore 105 therethrough defining an inner diameter $D_C$. Distal opening 109 of the cannula provides a working portal for the probe. It is further sized to allow the distal end of the probe to advance past the distal end 107 of the cannula. The length $L_C$ of the cannula is sized to reach from the patient's skin to a location within the cancellous bone region of the target bone. In several embodiments, the cannula comprises metal and/or polymer (e.g., Nitinol or polyether ether ketone (PEEK). In many embodiments, the cannula is made of an insulating material in order to prevent stray current from the probe from contacting non-targeted tissue.

In some embodiments, the cannula is shaped so as to guide the probe towards the midline of the vertebral body. This inward guidance will help move the electrodes closer to the BVN. In some embodiments, at least a portion of the cannula bore is curved. In some embodiments, at least half of the length of the cannula bore is curved. In other embodiments, substantially only the distal end portion of the cannula bore is curved.

Stylet 221 comprises a shaft 203 having a longitudinal axis F and a proximal 205 and distal end 207. Disposed at the distal end of the shaft is a tip 219 adapted for boring or drilling through cortical bone. In some embodiments, the outer diameter $D_O$ of the stylet shaft is preferably adapted to be received within the inner diameter $D_C$ of the cannula.

The combination of the cannula and the stylet is sometimes referred to herein as a "cannulated needle." In some embodiments, access to the vertebral body is gained by first placing the stylet in the cannula to produce a cannulated needle, piercing the skin with the cannulated needle, and advancing the cannulated needle so that the stylet tip reaches a target tissue region within the cancellous portion of the vertebral body, and then withdrawing the stylet. At this point, the cannula is conveniently located at the target tissue region to receive a probe.

Probe 301 comprises a shaft 303 having a longitudinal axis G, a distal end portion 305 and a proximal end portion 307. Disposed near the distal end portion of the probe is a first electrode 309 having a first face 331 and a connection face 333. The probe 301 is designed so that the connection face 333 of the first electrode is placed in electrical connection with a first lead 403 of the power supply. In this particular embodiment, the shaft has a longitudinal bore 311 extending from the proximal end portion up to at-least the first electrode 309. Disposed within the bore is a wire 321 electrically connected at its first end 323 to the first electrode 309 and having a second end 325 adapted to be electrically connected to a first lead of a power supply.

Several embodiments of systems comprise a cannula having a longitudinal bore, a stylet having an outer diameter adapted to be received within the longitudinal bore, and a distal tip adapted to penetrate cortical bone. The systems may comprise a probe or other treatment device. In one embodiment, the probe includes an outer diameter adapted to be received within the longitudinal bore, a first electrode, and a lead in electrical connection with the first electrode. A second, third, or fourth electrode is provided in some embodiments. In several embodiments, second, third, or fourth probes are provided.

In some embodiments, the outer surface of the probe or other treatment device is provided with depth markings or other indicia so that the clinician can understand the extent to which it has penetrated the vertebral body.

In some embodiments in which a cannulated stylet is first inserted, the stylet is removed and the cannula remains in place with its distal opening residing in the target tissue while the probe is inserted into the cannula. In one embodiment, the cannula provides a secure portal for the probe, thereby ensuring that the probe can enter the bone safely. This embodiment may be particularly advantageous when the probe is made of a flexible material, is curved, or is shaped with an irregular cross-section that could undesirably catch on the bone during probe advancement into the bone.

In the FIG. 32 probe disclosed above, probe 301 has a blunt tip. In other embodiments; however, the probe carrying at least one electrode can be configured to possess a sharp distal tip having sufficient sharpness to penetrate cortical bone. With such a tip, the clinician can eliminate steps in the procedure that are related to either the stylet or the cannulated stylet, and thereby save time.

Figure 33:
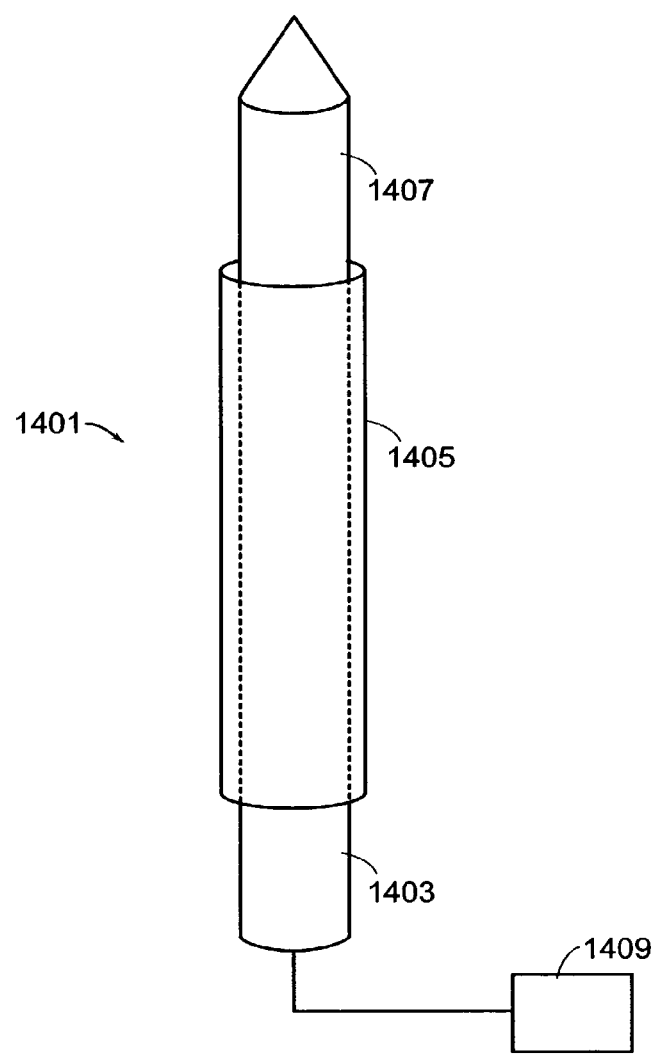
FIG. 33 discloses an embodiment in which a portion of the probe shaft acts as an electrode.

Now referring to FIG. 33, in some embodiments, the electrode may include a portion of the probe shaft. For example, in the case of probe 1401, the probe comprises: an inner electrically conductive shaft 1403 in electrical connection with a power supply 1409, and an outer insulating jacket 1405 wrapped around a portion of the shaft.

In this configuration, the placement of the jacket provides a distal uninsulated shaft portion 1407 that could be used as an electrode. In several embodiments, the distal uninsulated portion of the shaft has a length of between 3 mm and 8 mm (e.g., about 5 mm) In some embodiments thereof, the insulation is selected from the group consisting of polyimide tape, PTFE tape, and heat shrink tubing. Preferred thickness of the insulation may range from about 0.00025 to 0.0005 inches.

In some embodiments using insulating jackets, the jacket has either a longitudinally extending slit or slot that exposes a longitudinal surface area of the underlying shaft, thereby producing either an essentially linear or an essentially planar electrode. In such embodiments, the distal end of the shaft is insulated. In other embodiments using insulating jackets, the insulated portion may comprise a proximal jacket and a distal jacket positioned to provide a space therebetween that exposes a surface area of the underlying shaft to produce the electrode. In some embodiments, the proximal and distal jackets substantially encircle the shaft to provide an annular electrode therebetween.

In some embodiments in which a cannulated stylet is used, both the stylet and the cannula are removed, and the probe is inserted into the hole created by the cannulated stylet. In one embodiment, the hole provides a large portal for the probe. This embodiment conserves the annulus of bone removed by the cannula, and so may be preferred when the probe has a relatively large diameter (e.g., more than 8 mm in diameter). In some embodiments, the cannula remains to ensure that the probe tracks the hole and does not form its own pathway through the cancellous bone.

In some embodiments in which a cannulated stylet is used, the cannula comprises at least one electrode. In one embodiment, the cannula acts as the probe as well. With this embodiment, the clinician can eliminate steps in the procedure that are related to introducing a body into the cannula. In some embodiments, the outer surface of the cannula is provided with depth markings so that the clinician can understand the extent to which the cannula has penetrated the vertebral body.

In some embodiments in which a cannulated stylet is first inserted, the stylet comprises at least one electrode. In this embodiment, the stylet acts as the probe as well. With this embodiment, the clinician can eliminate steps in the procedure that are related to removing the stylet and introducing a body into the cannula. In some embodiments, the outer surface of the stylet is provided with depth markings so that the clinician can understand the extent to which it has penetrated the vertebral body.

Figure 31:
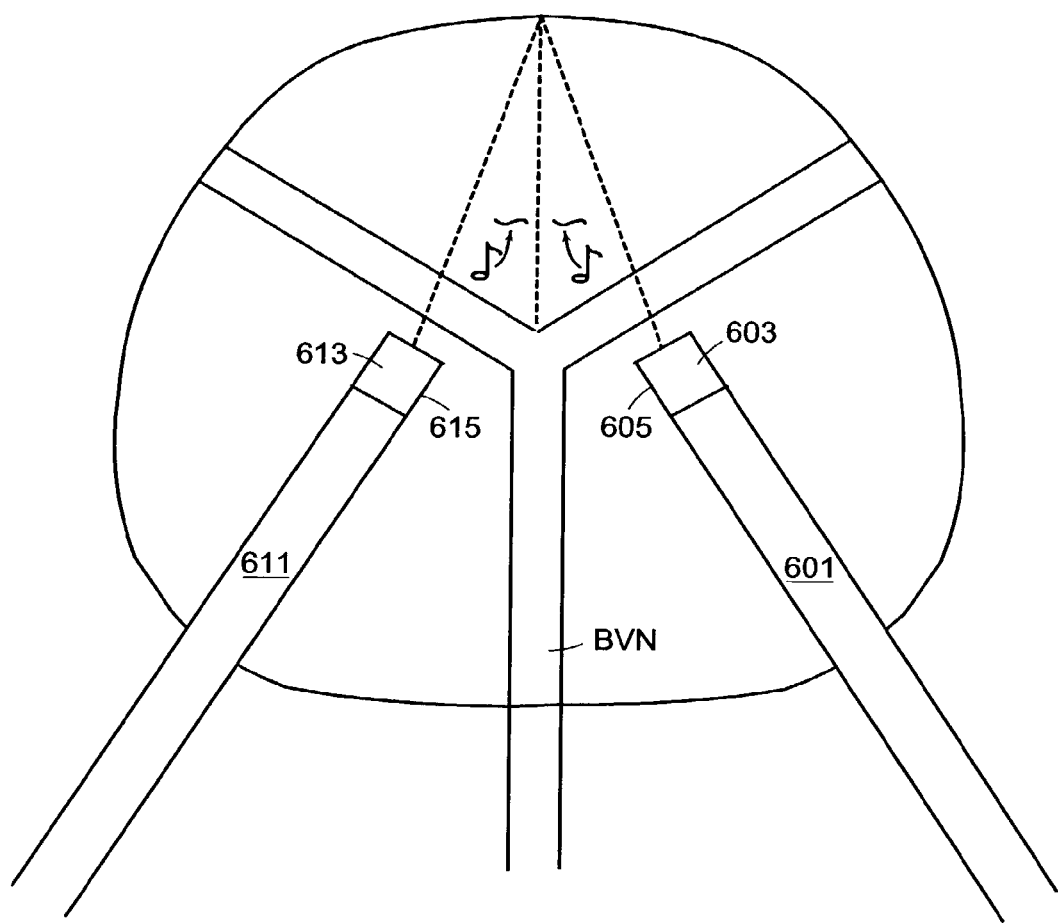
FIG. 31 depicts a top view of the treatment of the BVN with a bipolar electrode apparatus wherein the distal ends of the probes are located substantially at the midline of the vertebral body.

In conducting initial animal experiments with a dual probe embodiment, a bipedicle approach was used as shown in FIG. 31, so that each probe approached the ION at angle $\int$ of 45 to about 55 degrees. Since both the probes and the electrodes disposed thereon were essentially cylindrical, the inner faces 605, 615 of the electrodes produced an angle $2\int$. Subsequent testing of the configuration of FIG. 31 revealed somewhat higher temperatures at the distal portion of the electrodes and somewhat lower temperatures near the proximal portions of the electrodes. Without wishing to be bound by a particular theory, it is believed that the shorter path between the distal regions produced a lower resistance region (as compared to more proximal interelectrode regions) and so caused current to preferentially follow the path of the least resistance between the distal portions. Accordingly, the present inventors sought to improve upon the relatively uneven temperature profile produced by the electrode design of FIG. 31.

In accordance with embodiments of the invention, the electrode design can be modified to reduce the angle $2\int$ produced by the inner faces, so that the distance between the proximal end of the electrodes is more equal to the distance between the proximal end of the electrodes (e.g., the faces are more parallel). When the electrodes are provided in such a condition, their orientation reduces the significance of any path of least resistance, and so current flows more evenly across the face of each electrode, thereby providing even heating and greater control over the system.

In accordance with embodiments of the invention, there is provided an intraosseous nerve modulation system. In one embodiment, the modulation system comprises a first probe having an active electrode and a first lead, a second probe having a return electrode and a second lead, means for creating first and second bores within a bone for accommodating the first and second probes, and a power supply capable of generating a voltage difference between the active and return electrodes. In one embodiment, the power supply comprises third and fourth leads, wherein the first and third leads are in electrical connection, and the second and fourth leads are in electrical connection.

In some embodiments the electrodes are disposed so that the angle $2\int$ produced by the inner faces is less than 60 degrees (e.g., no more than 30 degrees). In other embodiments, the angle is less than 1 degree. In some embodiments, the inner faces are substantially parallel.

Figure 34:
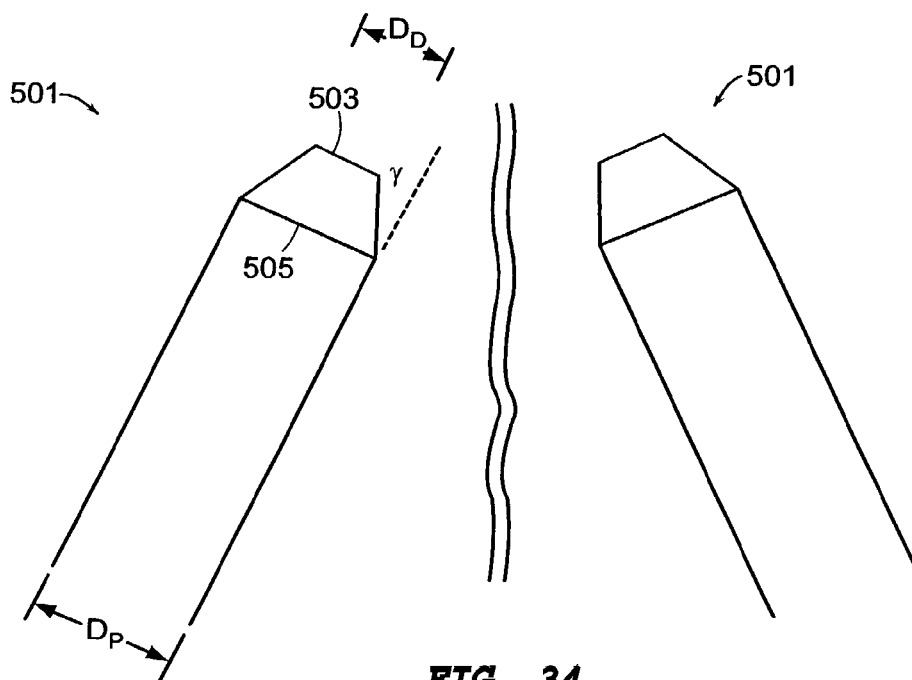
FIGS. 34-37 disclose four embodiments in which at least a portion of the electrode faces thereof are disposed in a substantially parallel relation.

Now referring to FIG. 34, in some embodiments, substantially parallel electrodes are provided by using conical electrodes 501 that taper distally. In FIG. 34, each cone electrode 501 has a distal end 503 having a diameter $D_D$ and a proximal end 505 having a diameter $D_P$, wherein the distal end diameter $D_D$ is larger than the proximal end diameter $D_P$. In several embodiments, the angle γ of the cone taper is substantially equal to the angle δ. In this condition, the inner faces of the conical electrodes will be essentially parallel to each other.

In accordance with embodiments of the invention, there is provided an intraosseous nerve denervation system comprising a first probe having a first electrode and a first lead in electrical connection with the first electrode, wherein the first electrode has a proximal end having a proximal diameter and a distal end having a distal diameter, and the proximal end diameter is less than the distal end diameter, and, optionally a second probe. In one embodiment, the second probe comprises a first electrode and a first lead in electrical connection with the first electrode. In one embodiment, the first electrode has a proximal end having a proximal diameter and a distal end having a distal diameter, wherein the proximal end diameter is less than the distal end diameter. In one embodiment, the first and second electrodes are disposed so that the electrodes are parallel. Non-parallel positioning is provided in other embodiments.

Figure 35:
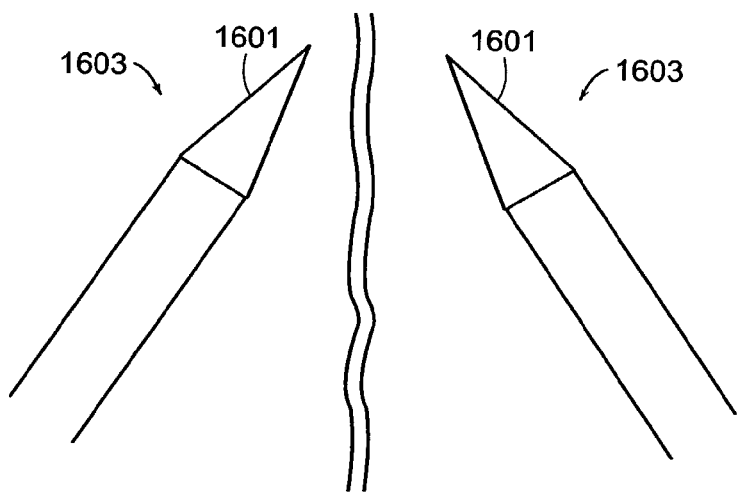

In FIG. 35, the conical shapes are frustoconical (i.e., they are portions of a cone). Frustoconical electrodes are desirable in situations where tissue charring needs to be avoided, as the relatively large diameter of the distal end of the electrode can not provide an avenue for high current density (relative to the proximal end of the electrode). Frustoconical electrodes are also desirable in situations where the probes are disposed at a relatively high angle γ, wherein the use of sharp tipped electrodes would substantially shorten the distance between the distal tips of the electrodes and thereby create an undesirable path of significantly less resistance.

In some embodiments, the frustoconical electrode is shaped so that the diameter of its distal end $D_D$ is between about 10% and 25% of the diameter of its proximal end $D_P$. In some embodiments, the frustoconical nature of the electrode is provided by physically severing the sharp distal end of the electrode. In others, the frustoconical nature of the electrode is provided by insulating the sharp distal end of an electrode.

As noted above, when the probes are placed such that their corresponding electrodes are parallel to each other, the electric field produced by electrode activation is substantially uniform between the distal and proximal portions of the electrodes. However, as the probes are oriented at an angle from parallel, the electric field becomes strongest where the electrodes are closer together. In order to compensate for this nonuniform electric field, in some embodiments, the distal ends of the electrodes are tapered. In this tapered state, the regions of the electrodes that are closer together (e.g., the tip) also have a smaller surface area (thereby reducing the electric field in that region), while the regions of the electrodes that are farther apart (e.g., the trunk) have a larger surface area (thereby increasing the electric field in that region). Typically, the effect is largely determined by the cone size, electrode spacing and tissue type therebetween.

In some embodiments of the tapered electrode, and now referring to FIG. 35, the distal end of the electrode terminates in a sharp tip, so that the electrode has a more completely conical shape. In several embodiments, the conical electrode is shaped so that the diameter of its distal end is no more than 20%, no more than 10%, or no more than 1% of the diameter of its proximal end. In addition to compensating for non-uniformity in the electric field, the sharp tip may also be adapted to penetrate the outer cortical shell of the vertebral body.

Figure 36:
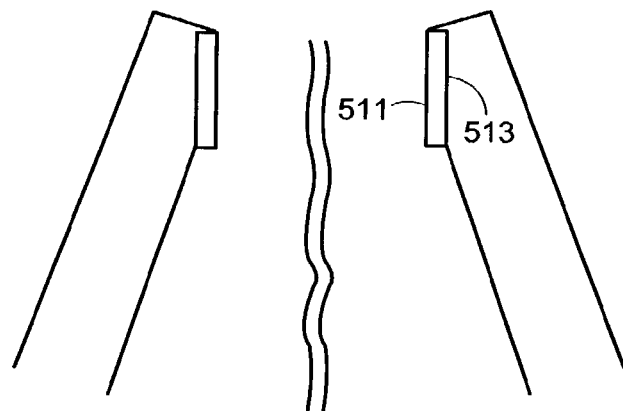

Now referring to FIG. 36, in some embodiments, current flows through an electrode having only a portion of the conical or frustoconical shape. When electrodes of this embodiment, termed "sectored cones," face each other, their use is advantageous because they ensure that current flows the least distance, and so provide efficiency. The sectored cones of this embodiment can be produced by first manufacturing planar electrodes 511 and placing the planar electrode upon a conveniently angled probe surface 513. Alternatively, this embodiment can be produced by first manufacturing the conical electrode configuration of FIG. 36, and then masking a portion of the conical electrode with an insulating material. Unlike the embodiment of FIG. 36, this sectored cone embodiment requires careful alignment of the electrode faces and may require in vivo rotation of the electrodes to achieve the desired alignment.

Figure 37:
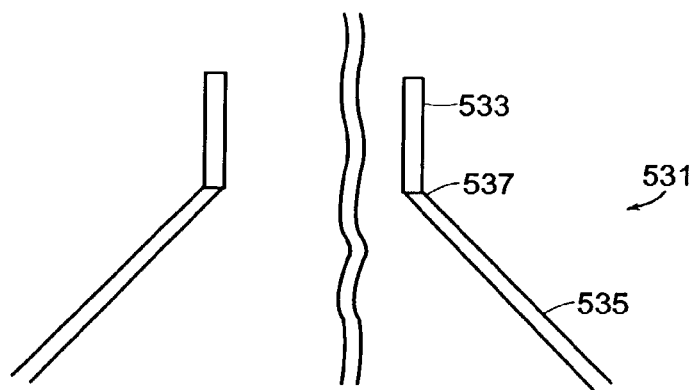

Now referring to FIG. 37, in other embodiments, substantially parallel electrodes can be provided by using elbowed probes 531. The elbowed probes can have a distal end 533 and a proximal end 535 meeting at an elbow 537. In some embodiments, the elbow may be produced during the manufacturing process (thereby requiring a smaller diameter probe in order to fit through the cannula). In other embodiments, the elbow is produced in vivo, such as through use of a pull-wire, a pivot or a memory metal disposed within the probe.

Figure 38:
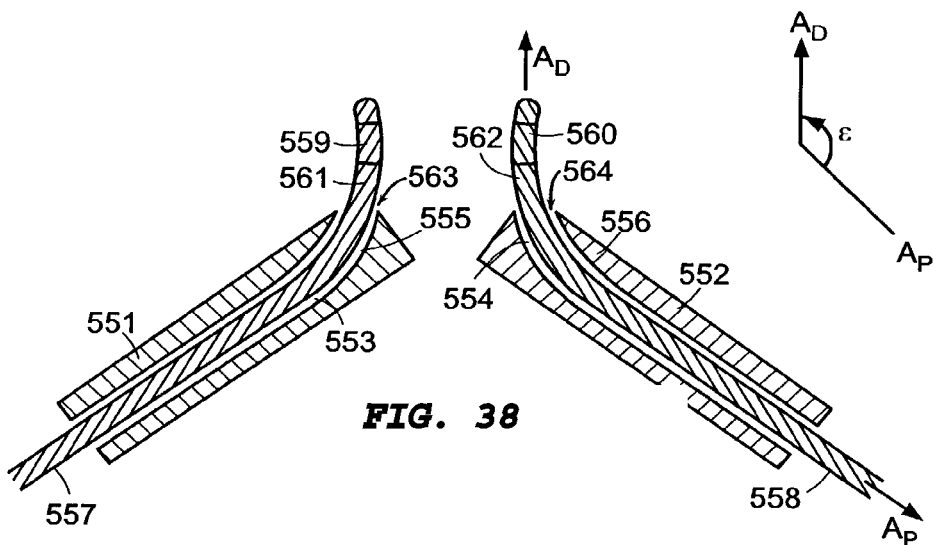
FIG. 38 discloses a cross-sectional view of an apparatus in which the cannula has a bore having a distal bend and a lateral opening.

Now referring to FIG. 38, in some embodiments, first 551 and. second 552 cannulae are each provided with a curved bore 553, 554 forming distal lateral openings 563, 564 in their respective distal end portions 555, 556. When flexible probes 557, 558 containing an electrode 559, 560 are passed through the curved bore, the distal end 561, 562 of the probe likewise conforms to the curved bore, thereby forming an intraprobe angle E determined by the proximal $A_P$ and distal $A_D$ axes of the probe. In several embodiments, this intraprobe angle is between 90 and 135 degrees, between 90 and 105 degrees, between 100 and 120 degrees, between 115 and 135 degrees, between 70 and 100 degrees, between 120 and 160 degrees, or overlapping ranges thereof. In several embodiments, the intra-probe angle is selected so that the distal axes $A_D$ of the probes exiting the cannulae form an angle of no more than 30 degrees, no more than 10 degrees, or form a substantially parallel relation. In some embodiments, the distal axes of the probes form an angle between 20-50 degrees, between 15-30 degrees between 5-15 degrees, between 0-8 degrees, or overlapping ranges thereof.

In accordance with embodiments of the invention, there is provided an intraosseous nerve denervation system, comprising a cannula having a longitudinal bore defining a first axis, a stylet having an outer diameter adapted to be received within the longitudinal bore and a distal tip adapted to penetrate cortical bone, and a first probe. In one embodiment, the first probe comprises an outer diameter adapted- to be received within the longitudinal bore, a first electrode, and a lead in electrical connection with the first electrode. Additional probes and/or electrodes are provided in other embodiments.

Figure 39A:
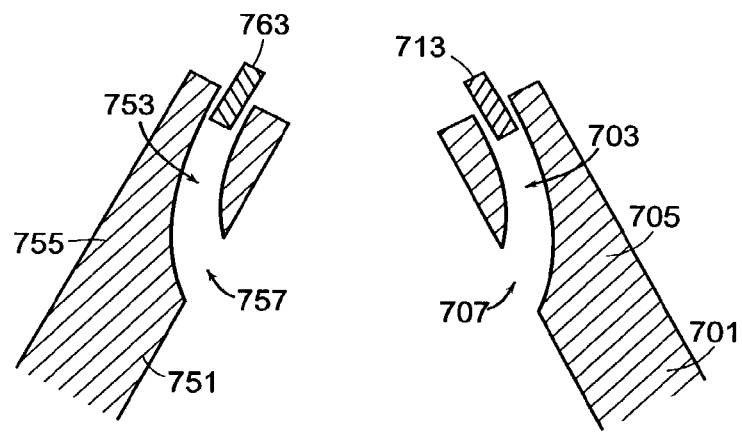
FIGS. 39A and 39B disclose cross-sectional views of an apparatus in which the cannula has a proximal bend.
Figure 39B:
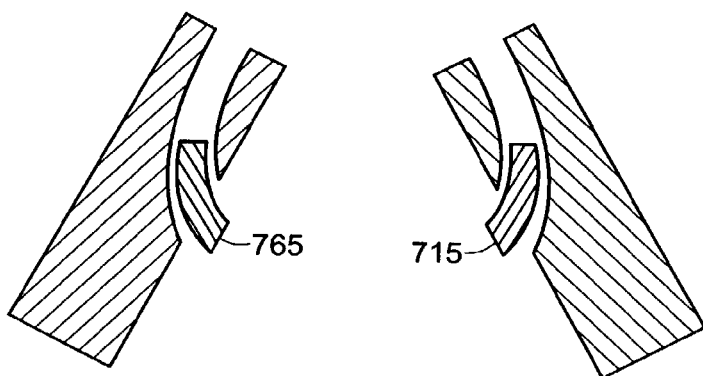

Now referring to FIGS. 39A and 39B, in some embodiments, first 701 and second 751 cannulae are each provided with a curved bore 703, 753 in their respective distal portions 705, 755, wherein each bore has a proximal lateral opening 707, 757. The apparatus further comprises first and second probes 711, 761, each containing an electrode 713, 763. In some embodiments, the probe may sit in a distal region of the bore (as in FIG. 39A) during advance of the cannula. Once the target tissue region is reached, then probes are moved proximally (by, for example, a pull wire—not shown) and exit the proximal lateral openings so that the inner faces 715, 765 of the electrodes face other.

Therefore, there is provided an intraosseous nerve denervation system, comprising a cannula having a longitudinal bore defining a first axis, a stylet having an outer diameter adapted to be received within the longitudinal bore and a distal tip adapted to penetrate cortical bone, and probe or other treatment device. In one embodiment, the probe or other treatment device comprises an outer diameter adapted to be received within the longitudinal bore, at least one electrode, and a lead in electrical connection with the at least one electrode. Multiple probes and multiple electrodes may be provided in some embodiments.

Figure 40A:
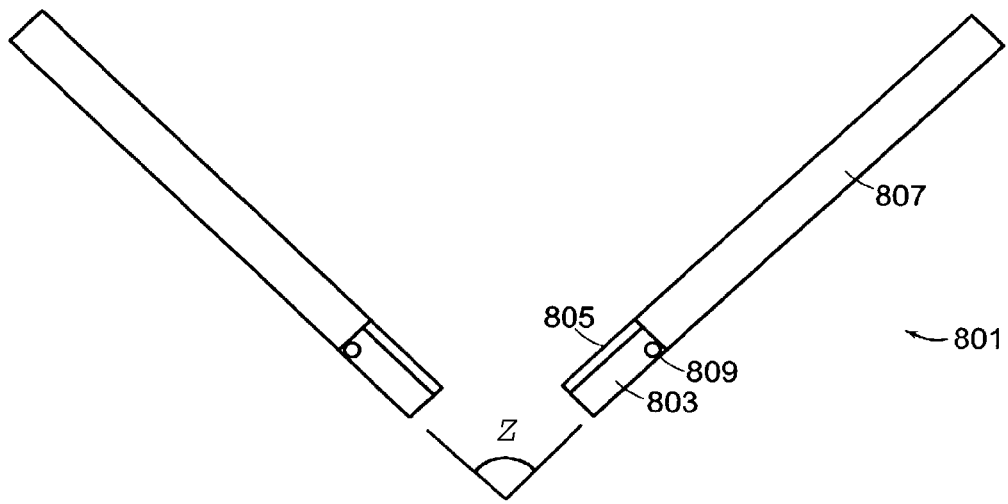
FIGS. 40A and 40B disclose-cross-sectional views of an apparatus in which the probe has a pivoted portion containing an electrode.
Figure 40B:
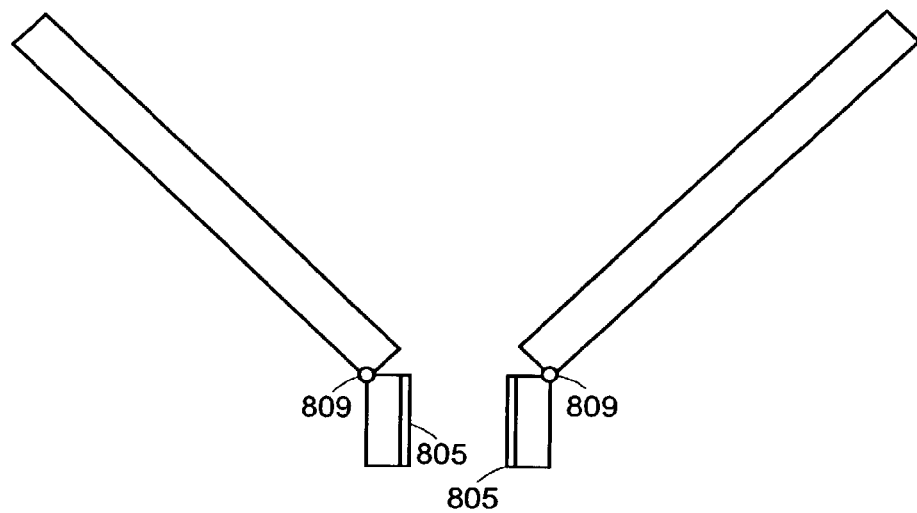
Figure 41:
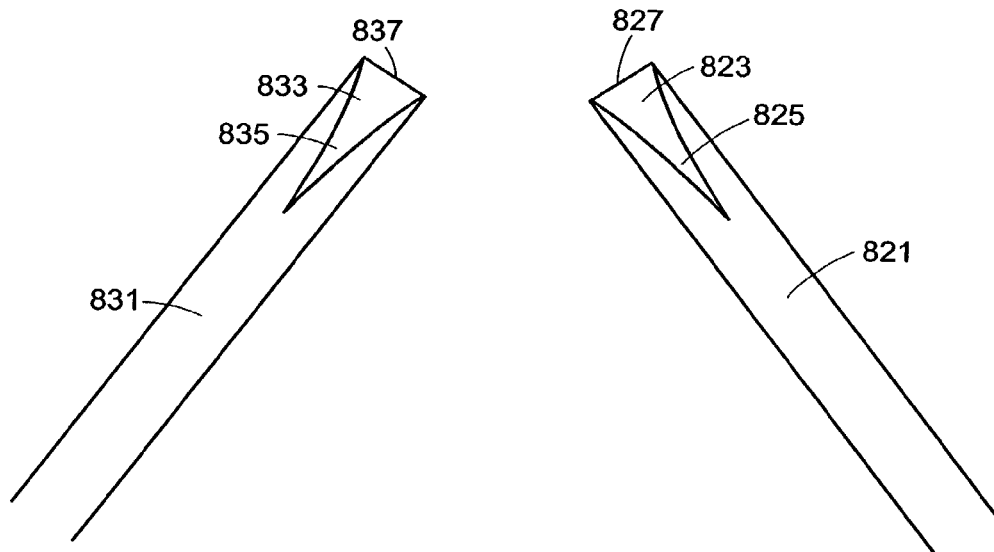
FIG. 41 discloses a probe having reverse conical electrodes.

Now referring to FIGS. 40A and 40B, in some embodiments, at least one probe 801 comprises a distal portion 803 having an electrode 805 and a proximal portion 807, with the distal portion being pivotally attached to the proximal portion by pivot 809. In some embodiments, two probes having such pivotally attached electrodes are introduced through the cannulae in a first linear mode (shown in FIG. 40A) to produce an angle Z between the electrodes. Next, the respective pivots may be actuated (by for example, a pull wire—not shown) to produce the angled configuration shown in FIG. 40B which reduces the angle between the electrodes. In accordance with several embodiments, the pivoting brings the electrodes into a substantially parallel relation.

In some embodiments, relatively even heating is provided by providing current density gradients. Now referring to FIG. 41, in some embodiments, first 821 and second 831 probes have first 823 and second 833 electrodes having a reverse conical shape. One or more electrodes can have a proximal end having a proximal diameter and a distal end having a distal diameter, with the proximal end diameter being less than the distal end diameter. In particular, each electrode may have a relatively thick distal portion 827, 837 and a relatively thin proximal portion 825, 835. When this probe is activated, it is believed that the current density of the electrodes will vary axially, with a relatively high current density present at the proximal portion of each electrode (due to the smaller surface area) and a relatively low current density present at the distal portion of the electrode (due to the larger surface area). This current density gradient may advantageously provide a more even heating zone when the electrodes themselves are oriented at a significant angle, as the preference for tip heating (caused by the angled orientation of the electrodes) is substantially balanced by the higher current density at the proximal portions of the electrodes.

Figure 42:
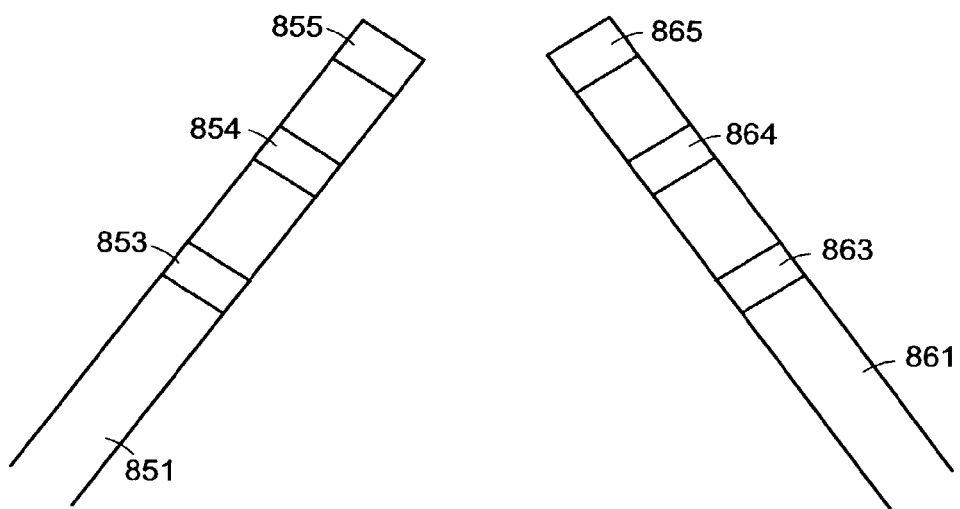
FIG. 42 discloses a probe having a plurality of active electrodes and a corresponding plurality of return electrodes.

Current density gradients can also be produced by providing a plurality of electrodes on each probe. Now referring to FIG. 42, in some embodiments, first and second electrodes each have a plurality of electrodes. In particular, first probe 851 has first 853, second 854 and third 855 active electrodes, while second probe 861 has first 863, second 864 and third 865 return electrodes. The voltage across the probes can be selected so that there is increasing voltage (and therefore current) across the more widely spaced electrodes (e.g., $V_{855-865} < V_{854-864} < V_{853463}$). In some embodiments, the probes of FIG. 42 are driven by multiple voltage sources (i.e., a first voltage source for providing voltage between first active electrode 853 and first return electrode 863, etc.).

In accordance with several embodiments, a method of therapeutically treating a vertebral body having a BVN comprises providing a first energy device having distal and proximal active electrodes, providing a second energy device having distal and proximal return electrodes, placing the first and second energy devices in the vertebral body to define a first distance between the distal active electrode and the distal return electrode, and a second distance between the proximal active electrode and the proximal return electrode. In one embodiment, the first distance is less than the second distance. In one embodiment, the method further comprises applying a first high frequency voltage between the distal active and distal return electrodes, and applying a second high frequency voltage between the proximal active and proximal return electrodes, with the first high frequency voltage being less than the second high frequency voltage.

Because multiple voltage sources may add complexity to the device, in other embodiments, the differences in voltage may be provided by a single voltage source by using a poorly conductive electrode. In particular, in some embodiments thereof, the probe comprises an electrically conductive probe shaft and a plurality of spaced apart insulating jackets, wherein the spacing produces the electrodes of FIG. 42. In this jacketed embodiment, the probe shaft can be made of a material that is a relatively poor electrical conductor (such as tantalum) so that, when a single driving force, is applied between the jacketed probes, the voltage is highest at the proximal electrode 853, but loss due to the poor conductance produces a substantially lower voltage at distal electrode 855. This jacketed embodiment may advantageously eliminate the need for multiple voltage sources.

Figure 43:
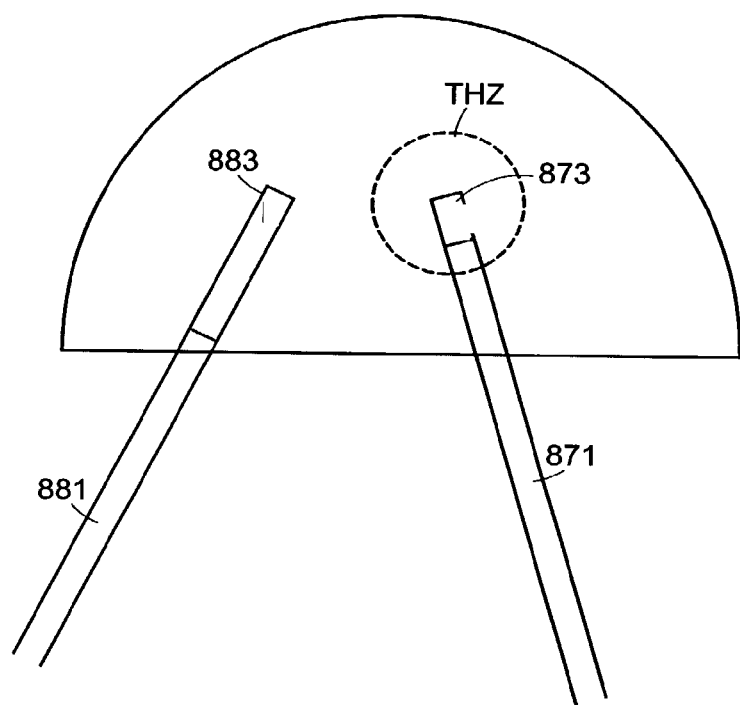
FIG. 43 discloses a bipolar probe in which the return electrode has a relatively large surface area.

In another dual probe approach, in some embodiments, and now referring to FIG. 43, there is provided an apparatus having first probe 871 having an active electrode 873, and a second 881 probe having a return electrode 883, wherein the ratio of the surface area of the active electrode to the surface area of the return electrode is very high, such as at least 2:1 (e.g., at least 5:1). In this condition, the current density can be very high at the active electrode and very low at the return electrode, so that the total heating zone THZ can occur essentially only around the active electrode. Since this device heats essentially only at the active electrode, this device substantially mimics, the heating profile of a monopolar electrode, but provides the desirable safety feature of locally directing the current to the return electrode.

Although the dual probe approach has many benefits in some embodiments, a single articulated probe having both active and return electrodes may be used in other embodiments. For example, a single probe may be placed such that a first electrode is on one side of midline (e.g., the left side) and a second electrode is on the other side of midline (e.g., the right side) of the vertebral body, or vice-versa. In some embodiments, the probe is curved such that one electrode is at or near the tip of the probe while the second electrode is near the beginning point of the curved region of the probe. The curved probe may be placed such that one electrode is opposite the other and both occupy similar positions relative to the anterior and posterior limits of the vertebral body. This can advantageously allow placement such that the two electrodes effectively straddle the BVN instead of using two separate probes. In some embodiments, the active electrode is at or near the tip of the probe, while in other embodiments, the return electrode is at or near the tip of the probe. In some embodiments, the first electrode comprises a tip electrode and the second electrode comprises a ring electrode.

Figure 44:
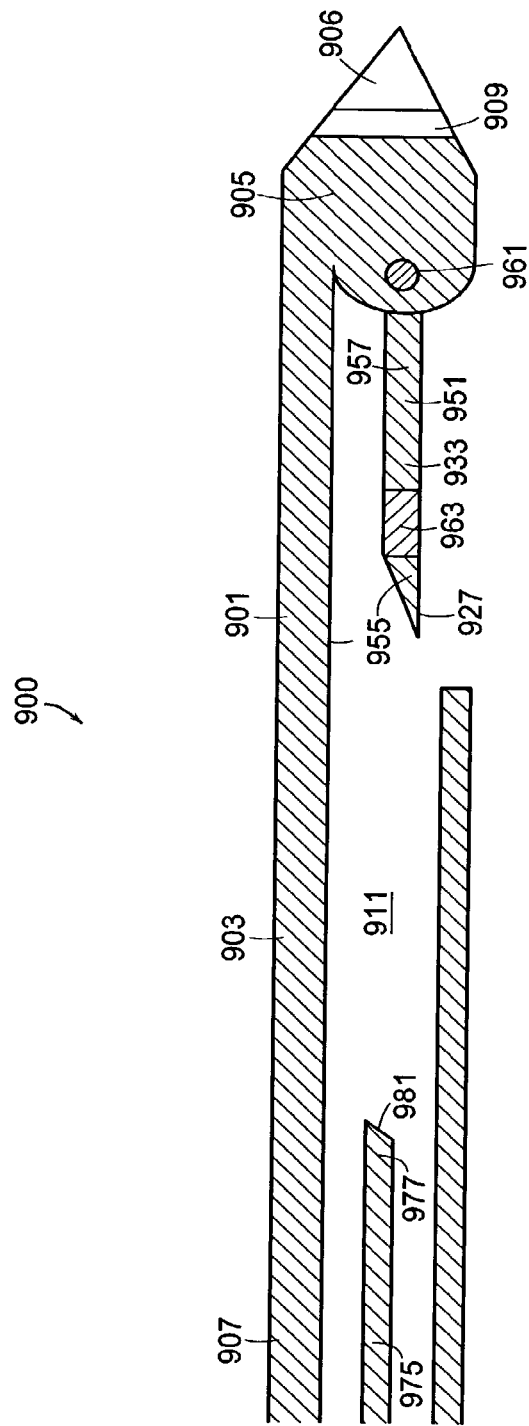
FIG. 44 presents a cross-sectional view of an articulated probe having both active and return electrodes.

Now referring to FIG. 44, there is provided a articulated device. In some embodiments, this device 900 comprises a fixed probe 901 and a pivotable probe 951. Fixed probe 901 comprises a shaft 903 having a longitudinal axis and a distal end portion 905 comprising sharpened distal tip 906 and a proximal end portion 907. Disposed near the distal end portion of the probe is first electrode 909. The fixed probe may be designed so that the first electrode is placed in electrical connection with a first lead of a power supply. In this particular embodiment, the shaft has a longitudinal bore 911 running from the proximal end portion up to at least the first electrode disposed within the bore is a first wire (not shown) electrically connected at its first end to the first electrode 909 and having a second end adapted to be electrically connected to a first lead of a power supply (not shown). The fixed probe 901 also comprises a recess 927 forming a lateral opening in the shaft and designed to house the pivotable probe 951 when in its undeployed mode.

Pivotable probe 951 comprises a shaft 953 having a longitudinal axis, a distal end portion 955, and a proximal end portion 957 pivotally attached to the fixed probe 901 by pivot 961. The pivot allows the pivoting probe 951 to pivot about the fixed probe 901. Disposed near the distal end portion of the pivotable probe 951 is second electrode 963. The probe is designed so that the second electrode 963 is placed in electrical connection with a second lead of the power supply.

In several embodiments, the pivotable probe has an undeployed mode and a deployed mode. In the undeployed mode, the pivotable probe is seated within the recess of the fixed probe so that the axis of its shaft is essentially in line with the axis of the fixed probe shaft. In this state, the pivotable probe essentially hides within the fixed probe. In the deployed mode, the pivotable probe extends at a significant angle from the fixed probe so that the axis of its shaft forms an angle of at least 10 degrees with the axis of the fixed probe shaft.

In some embodiments, a pusher rod is used to deploy the pivotable probe. Pusher rod 975 comprises a proximal handle (not shown) for gripping and a distal end portion 977 having a shape for accessing the bore of the fixed probe. Distal end portion has a tip 981 having a shape which, when advanced distally, can push the distal end portion of the pivotable probe laterally out of the recess.

In several embodiments, the pivotable device has both an active and a return electrode, and the device is introduced through a single pedicle. The location of these electrodes may vary depending upon the use of the pivotable device. For example, when the active electrode is located on the pivotable probe, the return electrode may be positioned in a location on the fixed probe distal of the pivot (as in FIG. 25), a location on the fixed probe proximal of the pivot; a location on the pivotable probe located nearer the pivot, a location on the pusher rod, or other locations. In other embodiments, the locations of the active and return electrodes are reversed from those described above.

In general, it may be desirable to operate embodiments of the invention in a manner that produce a peak temperature in the target tissue of between about 80° C. and 95° C. When the peak temperature is below 80° C., the off-peak temperatures may quickly fall below about 45° C. When the peak temperature is above about 95° C., the bone tissue exposed to that peak temperature may experience necrosis and produce charring. This charring reduces the electrical conductivity of the charred tissue, thereby making it more difficult to pass RF current through the target tissue beyond the char and to resistively heat the target tissue beyond the char. In some embodiments, the peak temperature is between 86° C. and 94° C., between 80° C. and 90° C., 85° C., overlapping ranges thereof, or any temperature value between 80° C. and 95° C.

It may be desirable to heat the volume of target tissue to a minimum temperature of at least 42° C. When the tissue experiences a temperature above 42° C., nerves within the target tissue may be desirably damaged. However, it is believed that denervation is a function of the total quantum of energy delivered to the target tissue; i.e., both exposure temperature and exposure time determine the total dose of energy delivered. Accordingly, if the temperature of the target tissue reaches only about 42° C., then it is believed that the exposure time of the volume of target tissue to that temperature should be at least about 30 minutes and preferably at least 60 minutes in order to deliver the dose of energy believed necessary to denervate the nerves within the target tissue.

It may be desirable to heat the volume of target tissue to a minimum temperature of at least 50° C. If the temperature of the target tissue reaches about 50° C., then it is believed that the exposure time of the volume of target tissue to that temperature need only be in the range of about 2 minutes to 10 minutes (e.g., about 2-4, 4-6, 6-8, 8-10 minutes) or any duration therebetween to achieve denervation. Shorter time periods may also be used.

It may be even more desirable to heat the volume of target tissue to a minimum temperature of at least 60° C. If the temperature of the target tissue reaches about 60° C., then it is believed that the exposure time of the volume of target tissue to that temperature need only be in the range of about 0.01 minutes to 1.5 minutes to achieve denervation (e.g., 0.1 minutes to 0.25 minutes).

Typically, the period of time that an ION is exposed to therapeutic temperatures is in general related to the length of time in which the electrodes are activated. In some embodiments, the electrodes, when the peak temperature is between 80° C. and 95° C., may be activated between 10 and 20 minutes, between 10 and 15 minutes, 12 minutes, 15 minutes, less than 10 minutes, greater than 20 minutes, or any duration of time between 10 and 20 minutes, to achieve the minimum target tissue temperature such that the nerve tissue is modulated (e.g., denervated). However, since it has been observed that the total heating zone remains relatively hot even after power has been turned off (and the electric field eliminated), the exposure time can include a period of time in which current is not running through the electrodes.

In general, the farther apart the electrodes, the greater the likelihood that the ION will be contained within the total heating zone. Therefore, in some embodiments the electrodes are placed at least 5 mm apart or at least 10 mm apart. However, if the electrodes are spaced too far apart, the electric field takes on an undesirably extreme dumbbell shape. Therefore, in many embodiments, the electrodes are placed apart a distance of between 1 mm and 25 mm, between 5 mm and 15 mm, between 10 mm and 15 mm between 3 mm and 10 mm, between 8 mm and 13 mm, between 10 mm and 18 mm, between 12 mm and 20 mm between 20 and 25 mm, between 1 mm and 3 mm, or any integer or value between 1 mm and 25 mm.

In some embodiments, it is desirable to heat the target tissue so that at least about 1 cc of bone tissue experiences the minimum temperature. This volume corresponds to a sphere having a radius of about 0.6 cm. Alternatively stated, it is desirable to heat the target tissue so the minimum temperature is achieved by every portion of the bone within 0.6 cm of the point experiencing the peak temperature.

In accordance with several embodiments, it is desirable to heat the target tissue so that at least about 3 cc of bone experiences the minimum temperature. This volume corresponds to a sphere having a radius of about 1 cm (e.g., 0.7 cm, 0.8 cm. 0.9 cm, 1.0 cm, 1.1 cm, 1.2 cm, 1.3 cm, 1.4 cm).

Some embodiments provide a steady-state heated zone having a peak temperature of between 80° C. and 95° C. (e.g., between 86° C. and 94° C., between 80° C. and 90° C., or overlapping ranges thereof), and heat at least 1 cc of bone (e.g., at least 2 cc of bone, at least 3 cc of bone, at least 4 cc of bone, at least 5 cc of bone) to a temperature of at least 50° C. (e.g., 60° C.).

In accordance with several embodiments, a method of therapeutically treating a vertebral body having a BVN comprises providing an energy device having an active and a return electrode, inserting the active electrode into the vertebral body, inserting the return electrode into the vertebral body, and applying a sufficiently high frequency voltage difference between the active and return electrodes to generate a current therebetween to produce a total heating zone having a diameter of at least 0.5 cm and a steady state temperature of at least 50° C.

As noted above, a peak temperature below about 100° C. or below about 105° C. is desirable in order to prevent charring of the adjacent tissue, steam formation and tissue popping. In some embodiments, this is accomplished by providing the power supply with a feedback means that allows the peak temperature within the heating zone to be maintained at a desired target temperature, such as 90° C. In some embodiments, the peak temperature is in the range of 85° C. to 95° C. In other embodiments, the peak temperature is between about 70° C. and 90° C.

In some embodiments, between about 24 watts and 30 watts of power is first supplied to the device in order to rapidly heat the relatively cool bone, with maximum amperage being obtained within about 10-15 seconds. In other embodiments, between about 28 watts and 32 watts of power, between about 20 watts and 26 watts of power, between 30 watts and 40 watts of power, between 15 watts and 24 watts of power, overlapping ranges thereof, or any power level within the ranges, is first supplied to the device. In some embodiments, the maximum amperage may be obtained within 5-10 seconds, within about 15-25 seconds, within about 7-12 seconds, within about 13-18 seconds, overlapping ranges thereof, or any duration within the recited ranges. As the bone is further heated to the target temperature, the feedback means gradually reduces the power input to the device to between about 6-10 watts. In some embodiments, the power input is reduced to between 4-7 watts, about 8-12 watts, between 2-6 watts, between about 7-15 watts, or overlapping ranges thereto.

Cooling may be employed for any of the neuromodulation devices (e.g., energy delivery devices) described herein. In several embodiments, a cooling balloon or other cooling device or fluid (e.g., heat removal elements, heat sinks, cooling fluid circulating through one or more lumens of the neuromodulation device) is used for cooling the treatment zone or location or the area surrounding the treatment zone or location.

If the active electrode has no active cooling means, it may become subject to conductive heating by the heated tissue, and the resultant increased temperature in the electrode may adversely affect performance by charring the adjacent bone tissue. Accordingly, in some embodiments, a cool tip active electrode may be employed. The cooled electrode helps maintain the temperature of the electrode at a desired temperature. Cooled tip active electrodes are known in the art. Alternatively, the power supply may be designed to provide a pulsed energy input. It has been found that pulsing the current favorably allows heat to dissipate from the electrode tip, and so the active electrode stays relatively cooler.

In various embodiments, the neuromodulation device comprises an electrosurgical probe having a shaft with a proximal end, a distal end, and at least one active electrode at or near the distal end. A connector may be provided at or near the proximal end of the shaft for electrically coupling the active electrode to a high frequency voltage source. In some embodiments, a return electrode coupled to the voltage source is spaced a sufficient distance from the active electrode to substantially avoid or minimize current shorting therebetween. The return electrode may be provided integral with the shaft of the probe or it may be separate from the shaft In some embodiments, the electrosurgical probe or catheter comprises a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

In several embodiments, the shaft is a rigid needle that is introduced through a percutaneous penetration in the patient. However, for endoscopic procedures within the spine, the shaft may have a suitable diameter and length to allow the surgeon to reach the target site (e.g., a disc) by delivering the shaft through the thoracic cavity, the abdomen or the like. Thus, the shaft may have a length in the range of about 5.0 to 30.0 cm (e.g., about 5-10, 10-15, 10-20, or 10-30 cm, or overlapping ranges thereof), and a diameter in the range of about 0.2 mm to about 10 mm (e.g., about 0.2-1, 1-2, 2-4, 2-6, 6-8, or 5-10 mm, or overlapping ranges thereof). In any of these embodiments, the shaft may also be introduced through rigid or flexible endoscopes.

The probe may include one or more active electrode(s) for applying electrical energy to tissues within the spine. The probe may include one or more return electrode(s), or the return electrode may be positioned on the patient's back, as a dispersive pad. In either embodiment, sufficient electrical energy is applied through the probe to the active electrode(s) to either necrose the blood supply or nerves within the vertebral body.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft may include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific deployment means will be described in detail in connection with the figures hereinafter.

In some embodiments, the electrically conductive wires may run freely inside the catheter bore in an unconstrained made, or within multiple lumens within the catheter bore.

The tip region of the instrument may comprise many independent electrode terminals designed to deliver electrical energy in the vicinity of the tip. The selective application of electrical energy is achieved by connecting each individual electrode terminal and the return electrode to a power source having independently controlled or current limited channels. The return electrode(s) may comprise a single tubular member of conductive material proximal to the electrode array. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing or preventing energy delivery to surrounding (non-target) tissue, such as the spinal cord.

Temperature probes associated with the apparatus may be disposed on or within the electrode carrier; between the electrodes (may be preferred in bipolar embodiments); or within the electrodes (may be preferred for monopolar embodiments). In some embodiments wherein the electrodes are placed on either side of the ION, a temperature probe is disposed between the electrodes or in the electrodes. In alternate embodiments, the deployable portion of the temperature probe comprises a memory metal.

The electrode terminal(s) may be supported within or by an inorganic insulating support positioned near the distal end of the instrument shaft. The return electrode may be located on the instrument shaft, on another instrument or on the external surface of the patient (i.e., a dispersive pad). In some embodiments, the close proximity of the dual needle design to the intraosseous nerve makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) may include the appropriate electrical connections for coupling the return electrode(s) and the electrode terminal(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes can include the use of formed wire (e.g., by drawing round wire through a shaping die) to form electrodes with a variety of cross-sectional shapes, such as square, rectangular, L or V shaped, or the like. The electrodes may be tip electrodes, ring electrodes, plate electrodes, cylindrical electrodes, frustoconical electrodes, or any other shape electrodes. Electrode edges may also be created by removing a portion of the elongate metal electrode to reshape the cross-section. For example, material can be ground along the length of a round or hollow wire electrode to form D or C shaped wires, respectively, with edges facing in• the cutting direction. Alternatively, material can be removed at closely spaced intervals along the electrode length to form transverse grooves, slots, threads or the like along the electrodes. In other embodiments, the probe can be sectored so that a given circumference comprises an electrode-region and an inactive region. In some embodiments, the inactive region is masked.

The return electrode is typically spaced proximally from the active electrode(s) a suitable. In most of the embodiments described herein, the distal edge of the exposed surface of the return electrode is spaced about 1 to 25 mm (or any distance therebetween) from the proximal edge of the exposed surface of. the active electrode(s), in dual needle insertions. Of course, this distance may vary with different voltage ranges, the electrode geometry and depend on the proximity of tissue structures to active and return electrodes. In several embodiments, the return electrode has an exposed length in the range of about 1 to 20 mm, about 2 to 6 mm, about 3 to 5 mm, about 1 to 8 mm, about 4 to 12 mm, about 6 to 16 mm, about 10 to 20 mm, 4 mm, 5 mm, 10 mm, or any length between 1 and 20 mm. The application of a high frequency voltage between the return electrode(s) and the electrode terminal(s) for appropriate time intervals effects modifying the target tissue. In several embodiments, the electrodes have an outer diameter of between 1 and 2 mm (e.g., between 1 and 1.5 mm, between 1.2 and 1.8 mm, between 1.5 and 1.7 mm, between 1.6 and 2 mm, 1.65 mm, or any outer diameter between the recited ranges). In several embodiments, the electrodes have an inner diameter of between 0.5 and 1.5 mm (e.g., between 0.5 and 0.8 mm, between 0.75 and 0.9 mm, between 0.8 and 1 mm, between 1 mm and 1.5 mm, 0.85 mm, or any inner diameter between the recited ranges).

Embodiments may use a single active electrode terminal or an array of electrode terminals spaced around the distal surface of a catheter or probe. In the latter embodiment, the electrode array usually includes a plurality of independently current limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other. electrode terminals in the array or to circuitry which limits or interrupts current flow to the electrode terminal when low resistivity material (e.g., blood) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In one embodiment, lower impedance paths may automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of me till, such as platinum).

In one embodiment of the invention, the active electrode comprises an electrode array having a plurality of electrically isolated electrode terminals disposed over a contact surface, which may be a planar or non-planar surface and which may be located at the distal tip or over a lateral surface of the shaft, or over both the tip and lateral surface(s). The electrode array may include at least two or more electrode terminals and may further comprise a temperature sensor. In one embodiment, each electrode terminal may be connected to the proximal connector by an electrically isolated conductor disposed within the shaft. The conductors permit independent electrical coupling of the electrode terminals to a high frequency power supply and control system with optional temperature monitor for operation of the probe. The control system may advantageously incorporate active and/ or passive current limiting structures, which are designed to limit current flow when the associated electrode terminal is in contact with a low resistance return path back to the return electrode.

The use of such electrode arrays in electrosurgical procedures may be particularly advantageous as it has been found to limit the depth of tissue necrosis without substantially reducing power delivery. The voltage applied to each electrode terminal causes electrical energy to be imparted to any body structure which is contacted by, or comes into close proximity with, the electrode terminal, where a current flow through all low electrical impedance paths is preferably but not necessarily limited. Since some of the needles are hollow, a conductive fluid could be added through the needle and into the bone structure for the purposes of lowering the electrical impedance and fill the spaces in the cancellous bone to make them better conductors to the needle.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes, twizzle shapes, spring shapes, twisted metal shapes, cone shapes, annular or solid tube shapes or the like. Alternatively, the electrode(s) may comprise a plurality of filaments, rigid or flexible brush electrode(s), side-effect brush electrode(s) on a lateral surface of the shaft, coiled electrode(s) or the like.

The voltage difference applied between the return electrode(s) and the electrode terminal(s) can be at high or radio frequency (e.g., between about 50 kHz and 20 MHz, between about 100 kHz and 2.5 MHz, between about 400 kHz and 1000 kHz, less than 600 kHz, between about 400 kHz and 600 kHz, overlapping ranges thereof, 500 kHz, or any frequency within the recited ranges. The RMS (root mean square) voltage applied may be in the range from about 5 volts to 1000 volts, in the range from about 10 volts to 200 volts, between about 20 to 100 volts, between about 40 to 60 volts, depending on the electrode terminal size, the operating frequency and the operation mode of the particular procedure. Lower peak-to-peak voltages may be used for tissue coagulation, thermal heating of tissue, or collagen contraction and may be in the range from 50 to 1500, from 100 to 1000, from 120 to 400 volts, from 100 to 250 volts, from 200 to 600 volts, from 150 to 350 volts peak-to-peak, overlapping ranges thereof, or any voltage within the recited ranges. As discussed above, the voltage may be delivered continuously with a sufficiently high frequency (e.g., on the order of 50 kHz to 20 MHz) (as compared with e.g., lasers claiming small depths of necrosis, which are generally pulsed about 10 to 20 Hz). In addition, the sine wave duty cycle (i.e., cumulative time in anyone-second interval that energy is applied) may be on the order of about 100%, as compared with pulsed lasers which typically have a duty cycle of about 0.0001%. In various embodiments, the current ranges from 50 to 300 mA (e.g., from 50 to 150 mA, from 100 to 200 mA, from 150 to 300 mA, overlapping ranges thereof, or any current level within the recited ranges).

A power source may deliver a high frequency current selectable to generate average power levels ranging from several milliwatts to tens of watts per electrode, depending on the volume of target tissue being heated, and/or the maximum allowed temperature selected for the instrument, tip. The power source allows the user to select the power level according to the specific requirements of a particular procedure.

The power source may be current limited or otherwise controlled so that undesired heating of the target tissue or surrounding (non-target) tissue does not occur. In one of the presently preferred embodiments, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909. Additionally, current limiting resistors may be selected. In several embodiments, microprocessors are employed to monitor the measured current and control the output to limit the current.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) can be formed at the distal tip of the electrosurgical instrument shaft, frequently being planar, disk-shaped, ring-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

The devices may be suitably used for insertion into any hard tissue in the human body. In some embodiments, the hard tissue is bone. In other embodiments, the hard tissue is cartilage. In some embodiments when bone is selected as the tissue of choice, the bone is a vertebral body. In several embodiments, devices are adapted to puncture the hard cortical shell of the bone and penetrate at least a portion of the underlying cancellous bone. In some embodiments, the probe advances into the bone to a distance of at least ⅓ of the cross-section of the bone defined by the advance of the probe. Some method embodiments are practiced in vertebral bodies substantially free of tumors. In others, method embodiments are practiced in vertebral bodies having tumors.

In some embodiments using two separate probes, the device enters the hard tissue (e.g., bone such as the vertebral body) through two access points. In some embodiments, the pair of separate probes is adapted to denervate the BVN and enter through separate pedicles transpedicularly. In other embodiments, the pair of separate probes each enters the vertebral body extrapedicularly. In other embodiments, a first of the pair of separate probes enters the vertebral body extrapedicularly and the second enters the vertebral body transpedicularly. In embodiments using a single device, the device enters via a single pedicle. In such embodiments, both the active and return electrodes may be disposed on a single probe, which may be placed transpedicularly via either the left pedicle or the right pedicle, such that one electrode crosses the midline and the second electrode remains on the same side of the midline as the pedicle entered. Thus, energy transmitted between the two electrodes effectively targets the BVN, which is disposed between the two electrodes. In some embodiments, this may be accomplished by utilizing a curved probe, such that the distal electrode may be placed at or near the tip of the probe and the proximal electrode may be placed at or near the starting point of the curve. Therefore, upon deployment of the probe in the vertebral body, the two electrodes of the single probe end up on either side of the midline at approximately the same anterior-posterior position. In other embodiments, a single probe with a fixed segment and a pivotable segment, in which at least one active and one return electrode are located on the single probe. Either or both electrodes may be located on the fixed segment or the pivotable segment. A single probe, with two electrodes placed on the probe, may also be used via extrapedicular entrance to the vertebral body.

Figure 45:
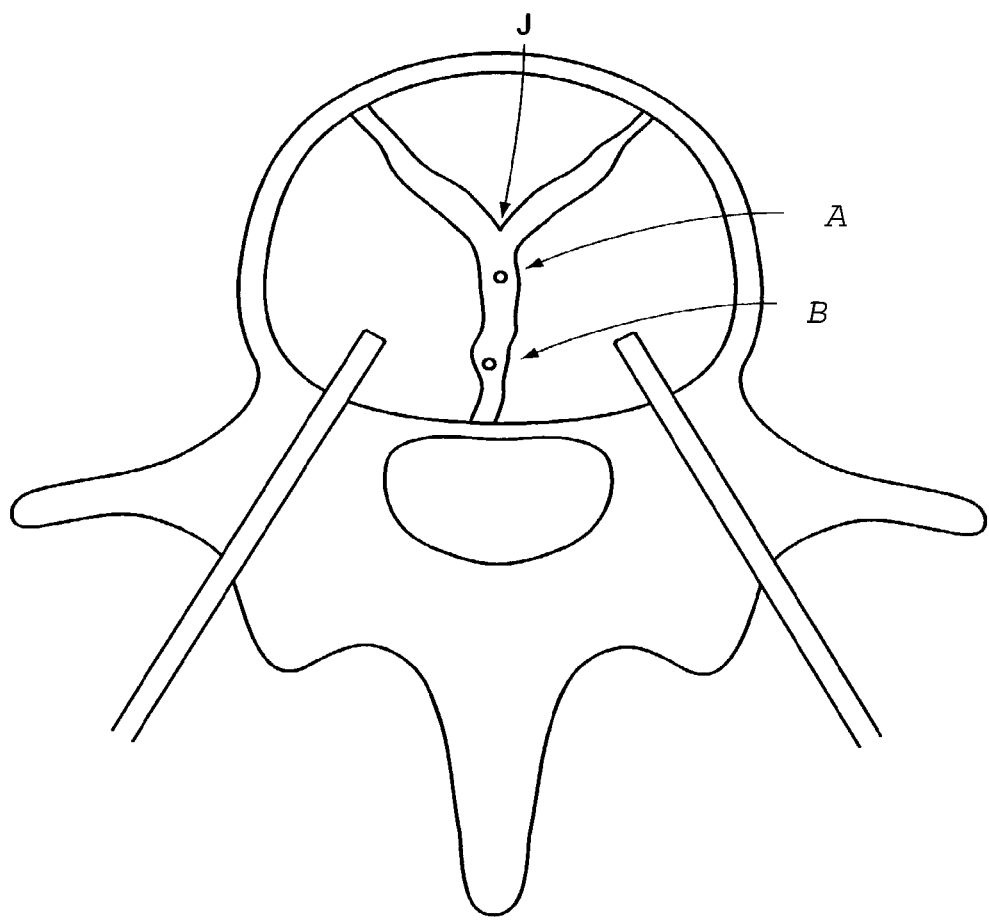
FIG. 45 discloses the treatment of a posterior portion of the BVN with a bipolar electrode apparatus.
Figure 46A:
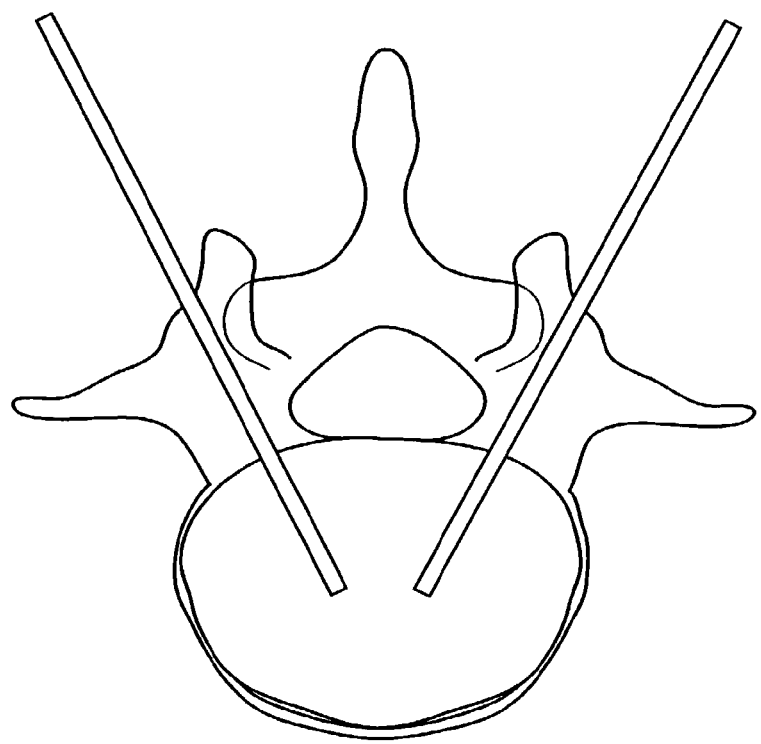
FIGS. 46A-46D disclose respective top, anterior, lateral and perspective views of the placement of a bipolar electrode apparatus within a vertebral body.
Figure 46B:
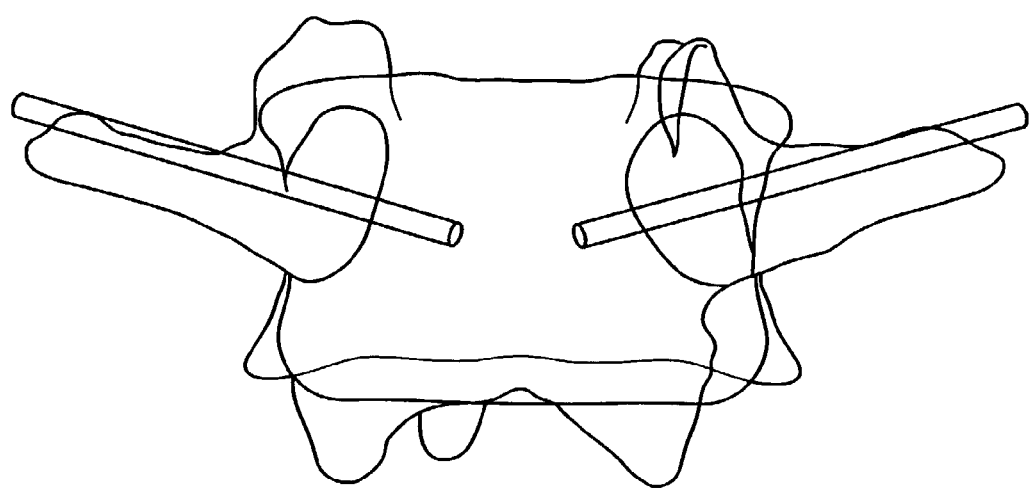
Figure 46C:
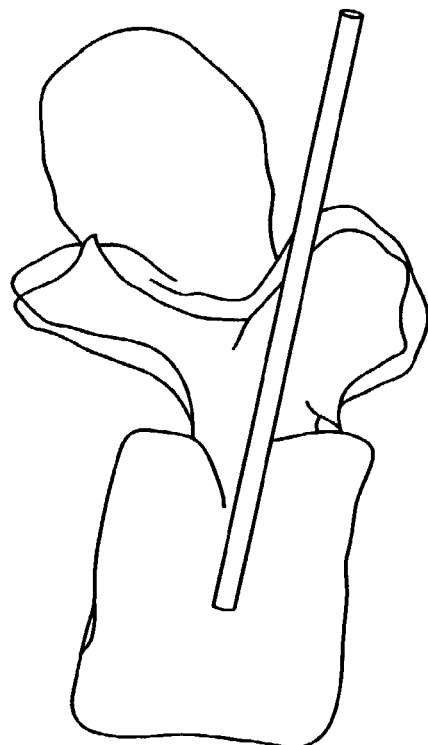
Figure 46D:
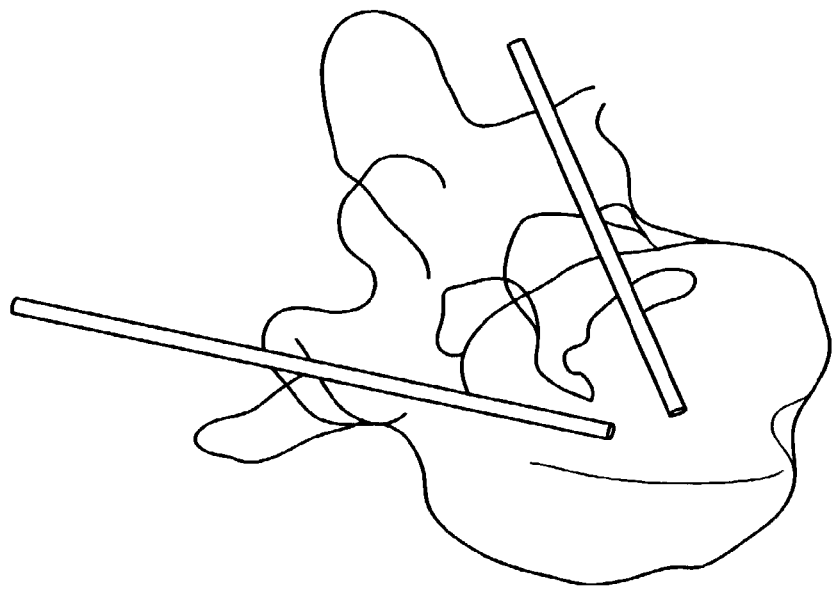

Now referring to FIG. 45, in some embodiments, the target region of the BVN is located within the cancellous portion of the bone (i.e., to the interior of the outer cortical bone region) and proximal to the junction J of the BVN having a plurality of branches. In accordance with several embodiments, treatment in this region is advantageous because only a single portion of the BVN or a small number of initial branches need be effectively treated to denervate the entire system. In some embodiments, treatment of the BVN in locations more downstream than the junction J or treatment location T may require the denervation of each branch.

EXAMPLES

The following Examples illustrate some embodiments of the invention and are not intended in any way to limit the scope of the disclosure. Moreover, the methods and procedures described in the following examples, and in the above disclosure, need not be performed in the sequence presented.

Example I

This example describes an embodiment of a method of use of one of the dual probe embodiments.

First, after induction of an appropriate amount of a local anesthesia, the human patient is placed in a prone position on the table. The C-arm of an X-ray apparatus is positioned so that the X-rays are perpendicular to the axis of the spine. This positioning provides a lateral view of the vertebral body, thereby allowing the surgeon to view the access of the apparatus into the vertebral body.

Next, a cannulated stylet comprising an inner stylet and an outer cannula are inserted into the skin above each of the respective pedicles so that the distal tip of each stylet is in close proximity to the respective pedicle.

Next, the probe is advanced interiorly into the body so that the stylet tips bores through the skin, into and through the pedicle, and then into the vertebral body. The stylet is advanced until the tips reach the anterior-posterior midline of the vertebral body.

Next, the stylet is withdrawn and probe is inserted into the cannula and advanced until the first and second electrodes thereof each reach the midline of the vertebral body. The location of the two probes is shown from various perspectives in FIGS. 46A-46D. As shown, the probes can be inserted using a transpedicular access approach.

Next, the power supply is activated to provide a voltage between the first and second electrodes. The amount of voltage across the electrodes is sufficient to produce an electric current between the first and second electrodes. This current provides resistive heating of the tissue disposed between the electrodes in an amount sufficient to raise the temperature of the local portion of the BVN to at least 45° C., thereby denervating the BVN.

Example II

This example describes the efficacy of heating a large zone of a vertebral body with an embodiment of a bipolar energy device. In accordance with one embodiment, the testing procedure was performed as follows:

A pair of probes was inserted into a vertebral body of an ovine animal model so that the tips of the electrodes were located substantially at the midline and separated by about 4 mm. Each electrode had a cylindrical shape, a length of about 20 mm, and an outer diameter of about 1.65 mm (16 gauge) to produce a surface area of about 100 $mm^2$.

Figure 47A:
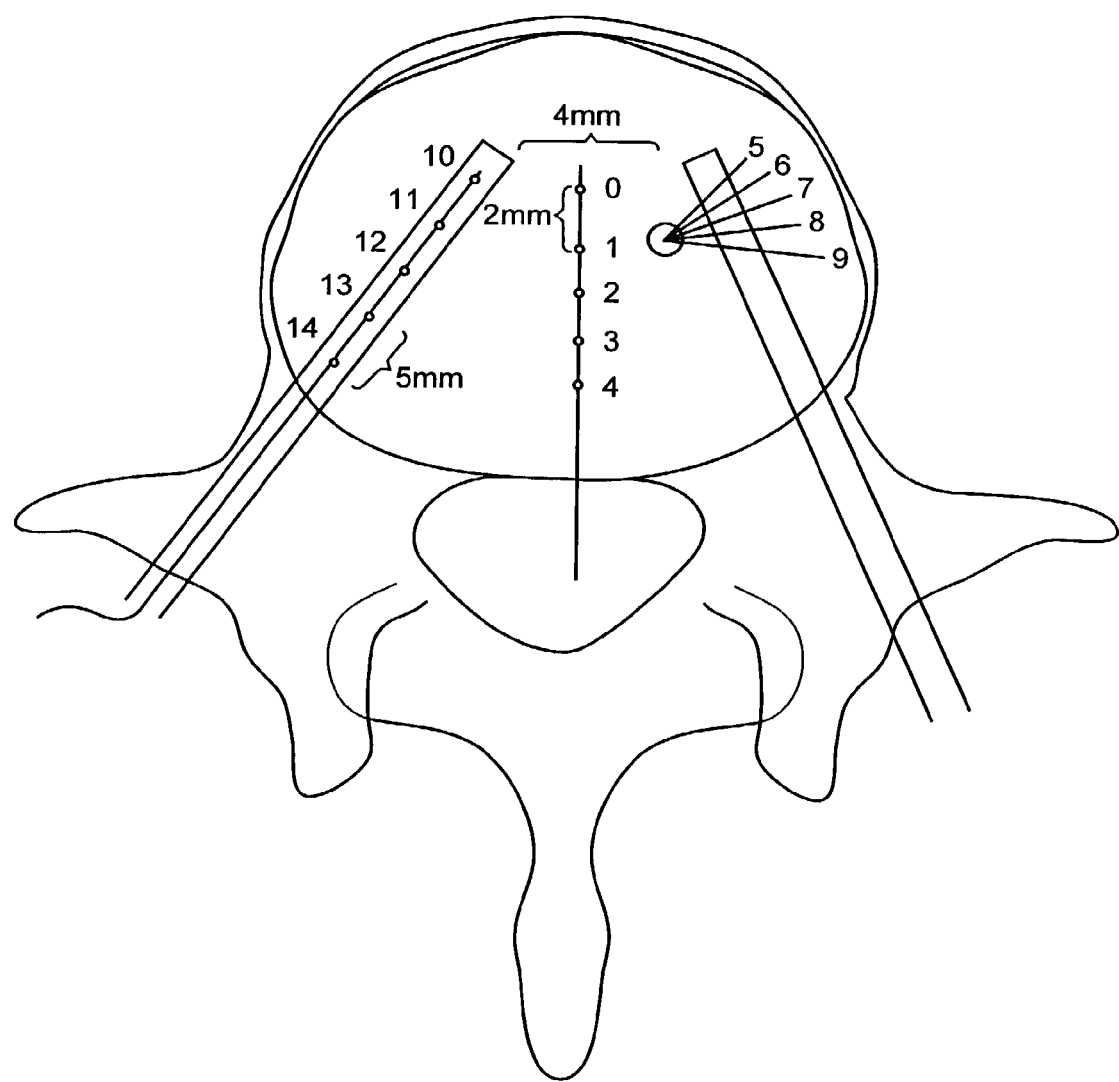
FIGS. 47A and 47B show the location of thermocouples T0-T14 within the vertebral body.
Figure 47B:
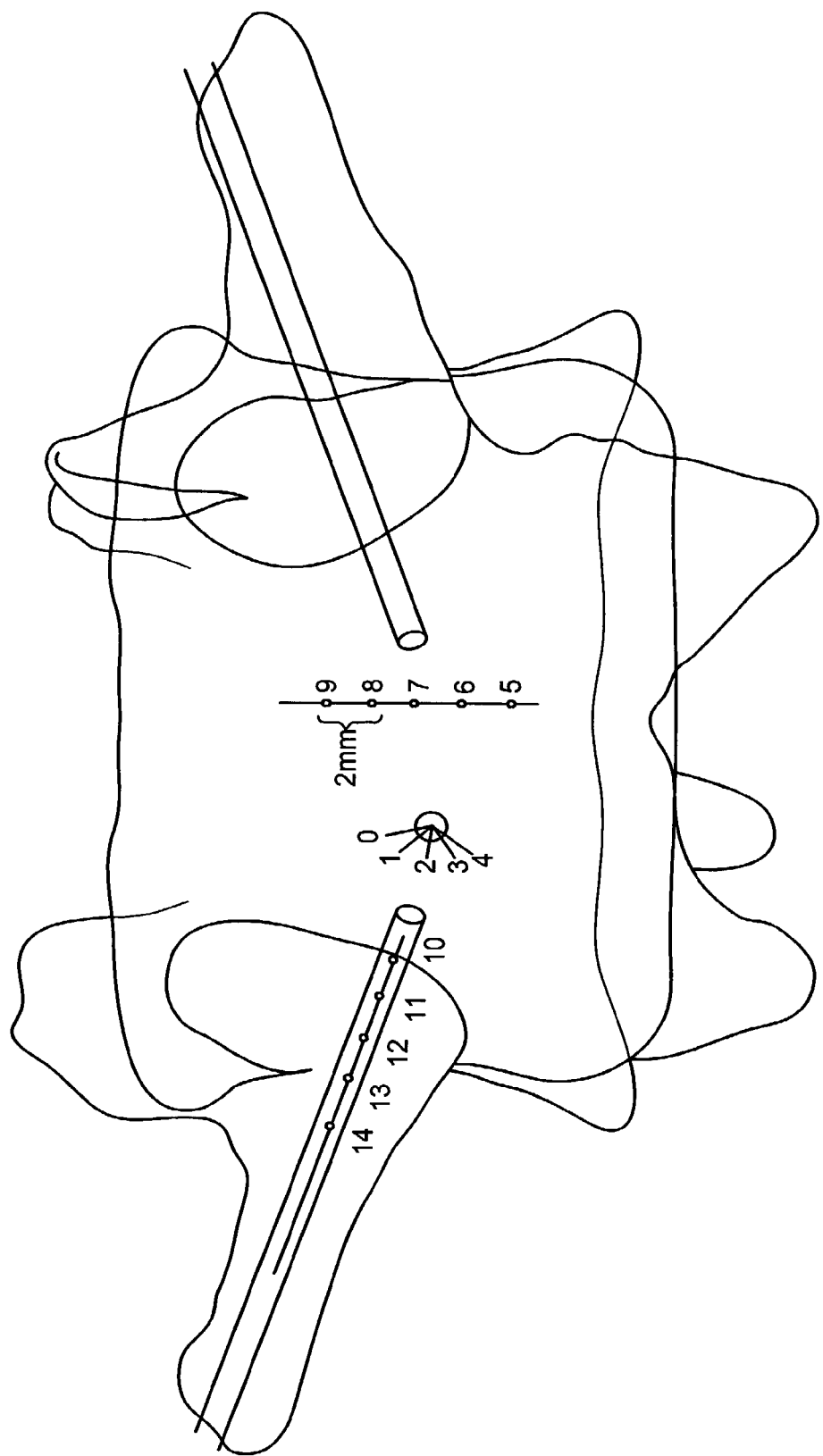
Figure 48A:
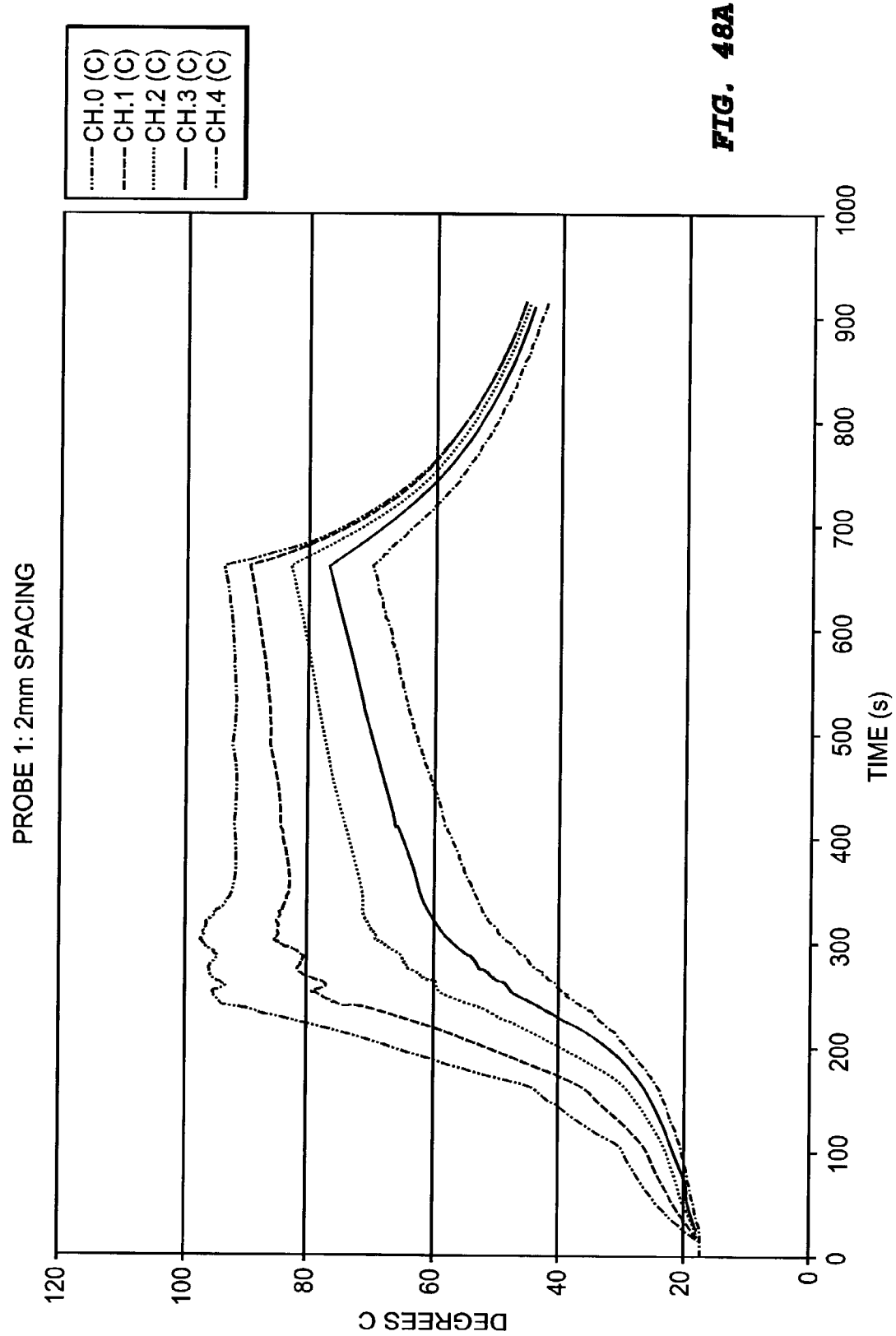
Figure 48B:
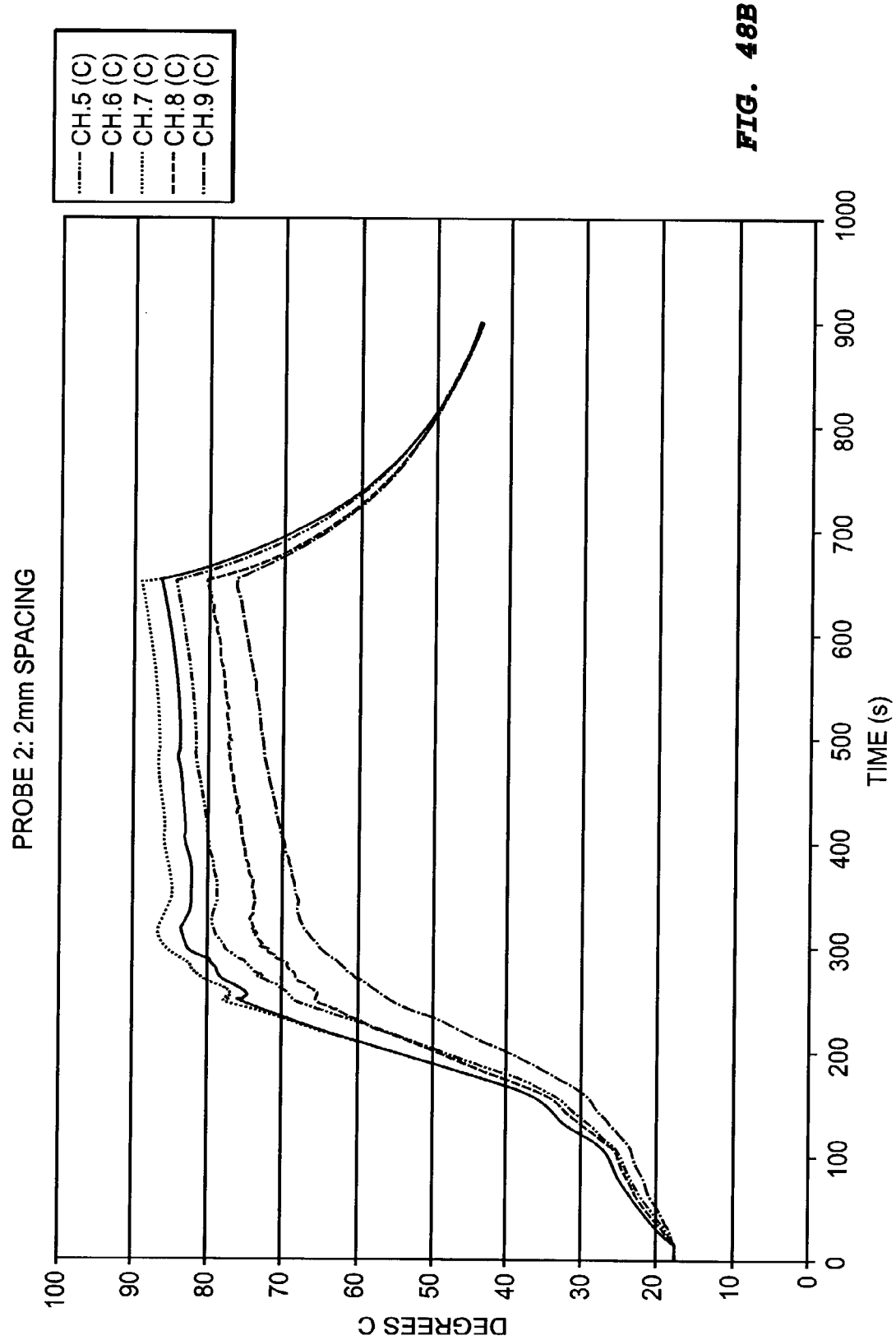

Next, and now referring to FIGS. 47A and 47B, thermocouples 0-14 were placed within the vertebral body at the 15 locations. Thermocouples 0-4 were placed halfway between the electrode tips and were separated by a distance of 2 mm. Thermocouples 5-9 were placed about at the midpoint between the probe tips, and were vertically separated by a distance of 2 mm Thermocouples 10-14 were placed along the distal portion of the probe and were separated by a distance of 5 mm.

Next; about 57 volts of energy was applied across the electrodes, and the temperature rise in the tissue was recorded at the thermocouple sites. These temperatures are provided in FIGS. 48A-48C. In general, the temperature at each site rose somewhat steadily from about 22° C. to its peak temperature in about 200-300 seconds, whereupon feedback controls maintained the peak temperatures.

Figure 49A:
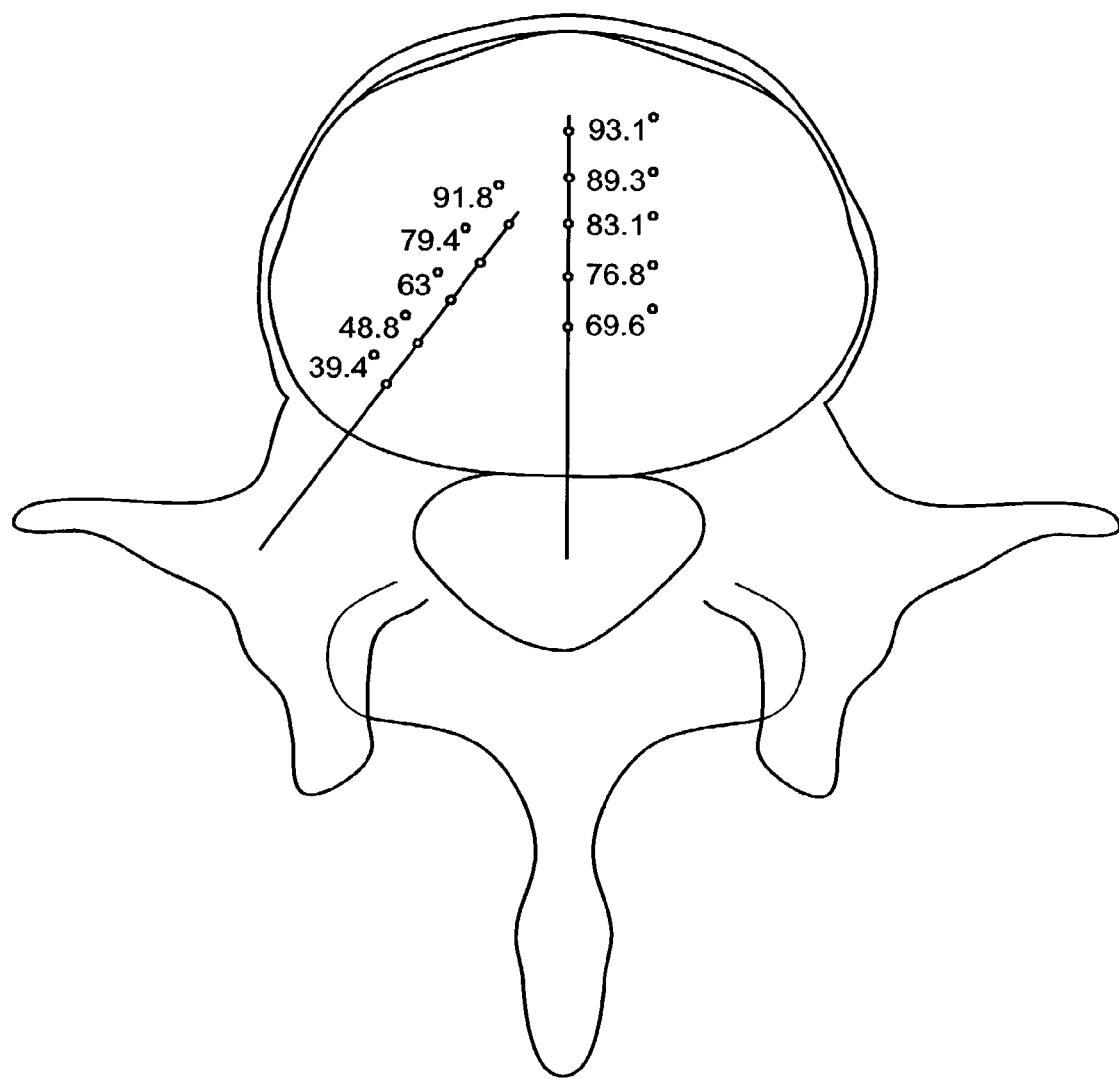
FIGS. 49A and 49B present the peak temperatures recorded by thermocouples T0-T14 within the vertebral body.
Figure 49B:
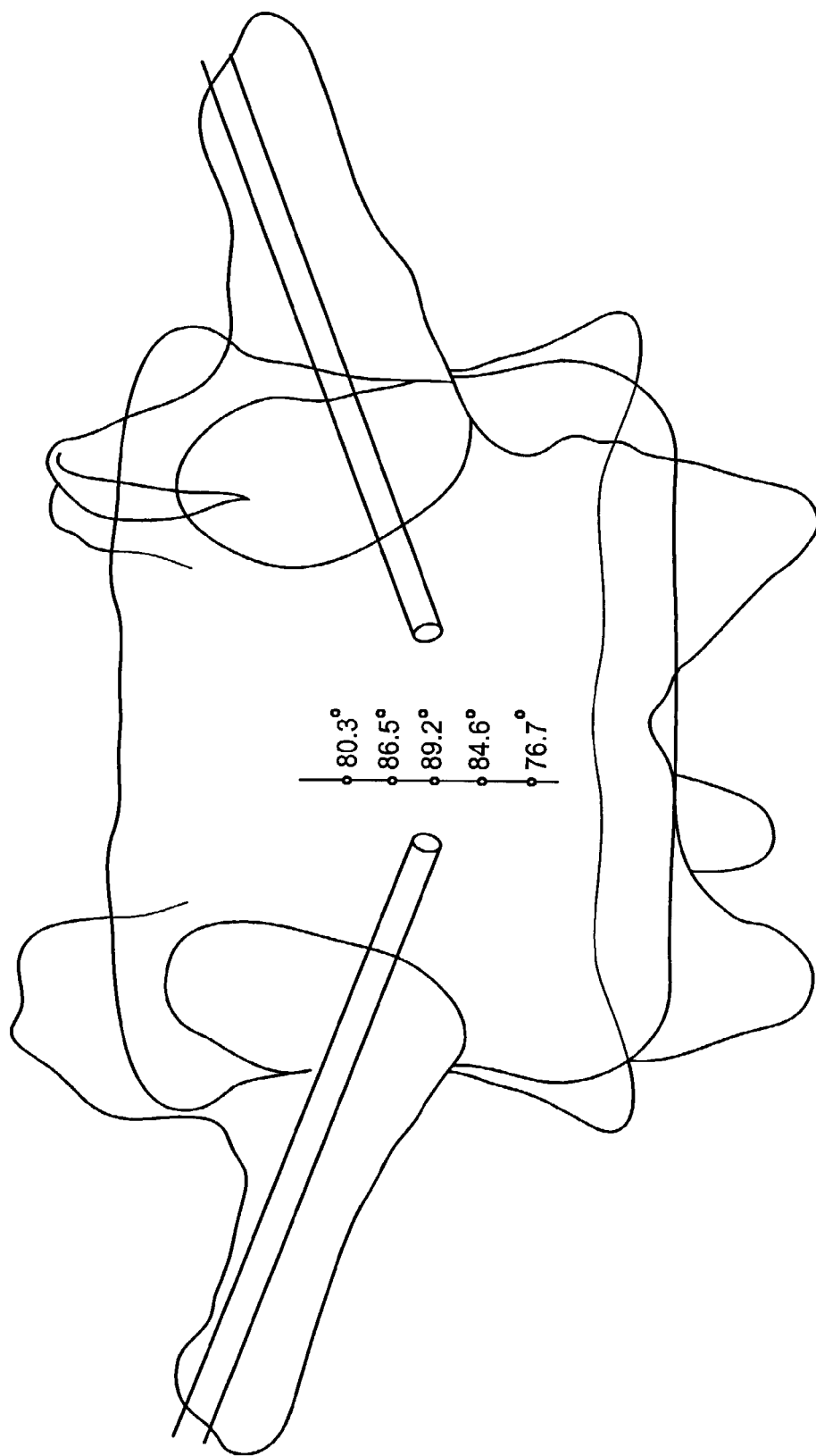

FIGS. 49A and 49B provide the peak-temperatures recorded by each thermocouple. Analysis of the results in FIGS. 49A and 49B reveals that peak temperatures of between about 80° C. and 95° C. were able to be sustained over substantial distances. In particular, a temperature of 79.4 degrees was reached about 10 mm along the electrode (T11); temperatures of between 76.7 and 80.3° C. were reached at a depth of about 4 mm within the tissue (T5 and T9); and a temperature of 76.8° C. was reached about 10 mm along the electrode (T3).

The positive results provided by this example have great significance to the problem of therapeutically heating IONs, and the BVN in particular. In particular, the results of thermocouples T5-9 indicates that if an ION were located along the z-axis within 2 mm of the presumed center of the IRZ, then the ION could be sufficiently treated to at least 80° C. Similarly, the results of thermocouples T 0-4 indicate that as much as a 16 mm length of ION could be sufficiently treated to at least 80° C. Lastly, the results of thermocouples T 10-14 indicate that the ION could be off-center laterally in the IRZ by as much as 2 mm and at least about 10 mm of its length could be sufficiently treated to at least 80° C.

Example III

This embodiment describes an example of a method of use of an articulated probe. In accordance with one embodiment, the method is performed as follows:

The initial steps described above in Example I can be carried out so that the articulated probe is poised on the patient's skin and held in place by a ratchet type gun. See FIG. 50A.

Next, the distal end of the articulated probe is inserted into the skin above a pedicle so that the distal end of the fixed probe is in close proximity to the pedicle.

Figure 50A:
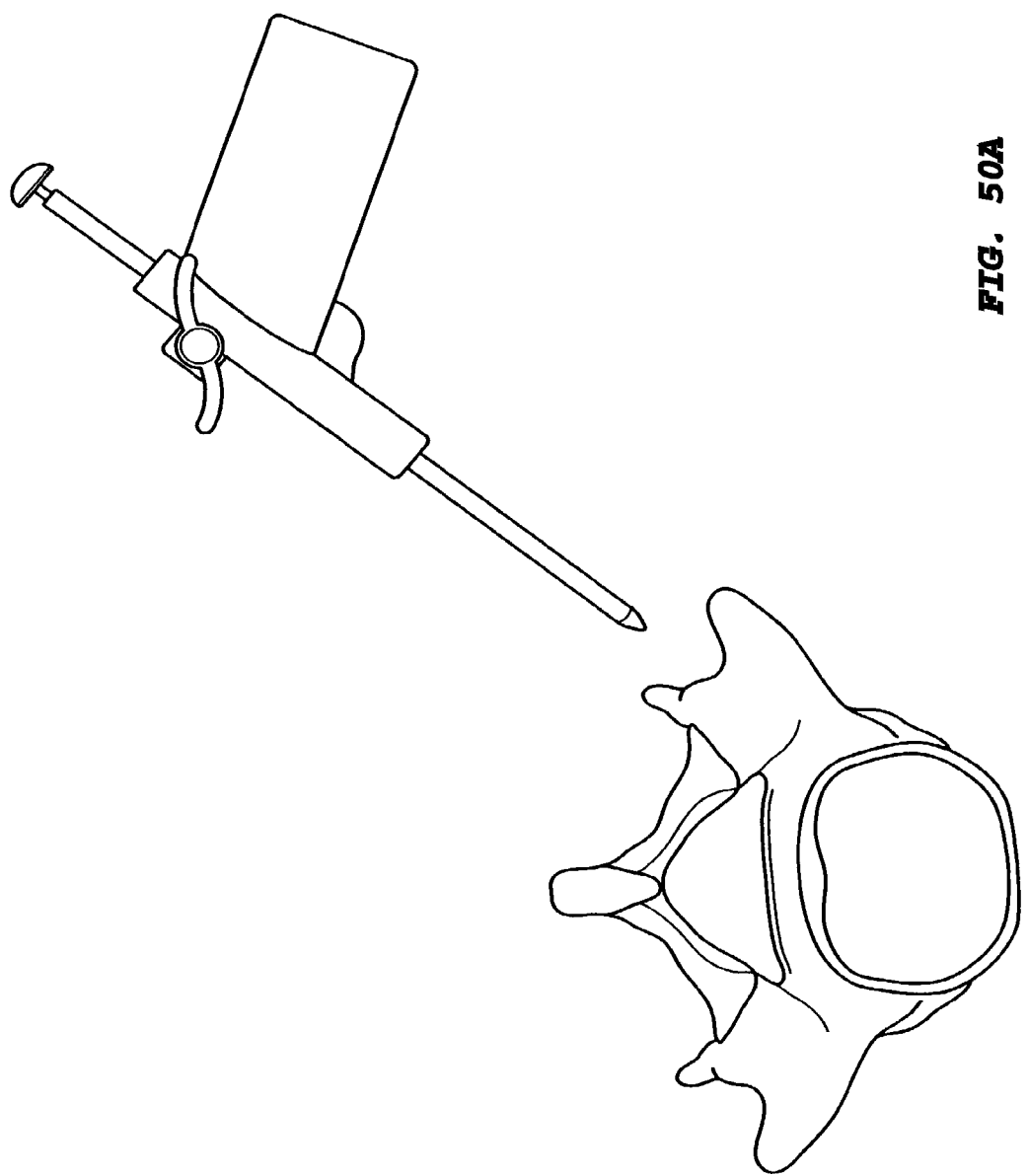
FIGS. 50A-50E present top views of a use of the articulated probe of FIG. 44.
Figure 50B:
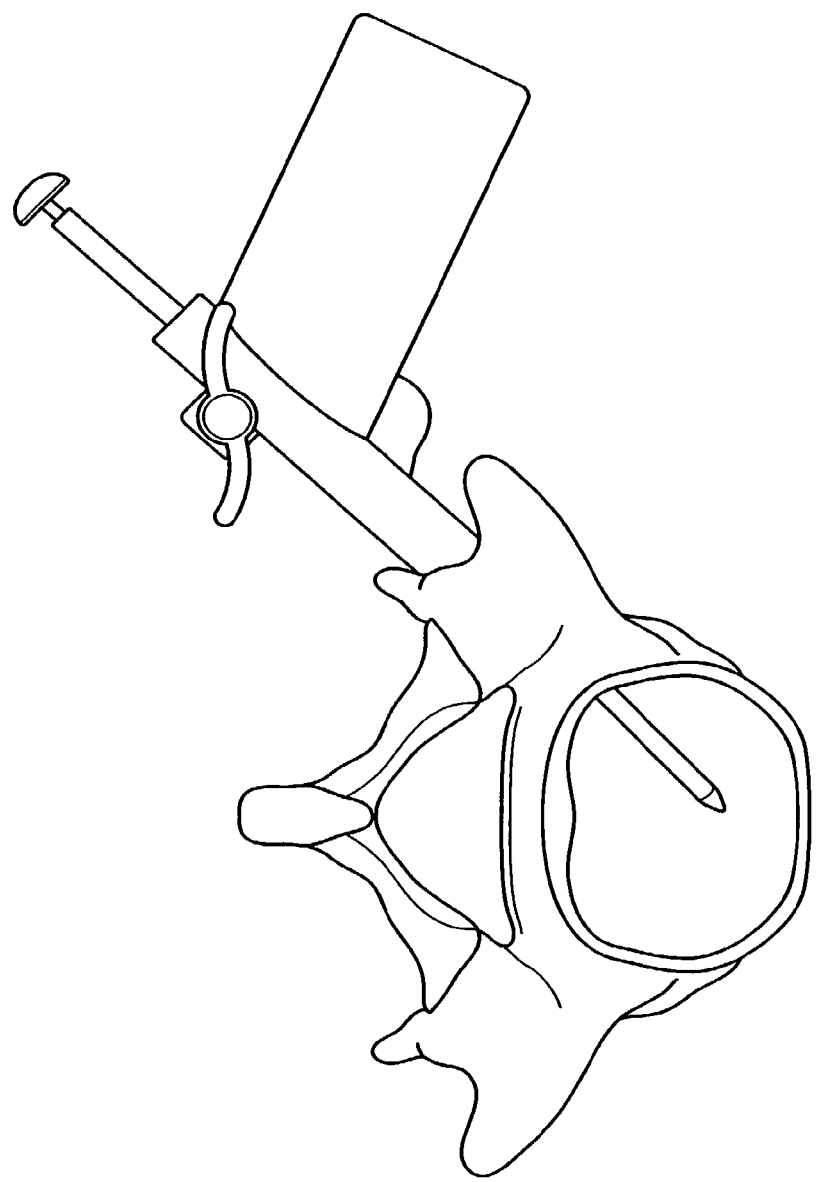

Now referring to FIG. 50B, the probe is advanced interiorly into the body so that the distal tip bores through the skin, into and through the pedicle, and then into the vertebral body. The distal tip is advanced until it reaches about 30% beyond the anterior posterior midline of the vertebral body.

Figure 50C:
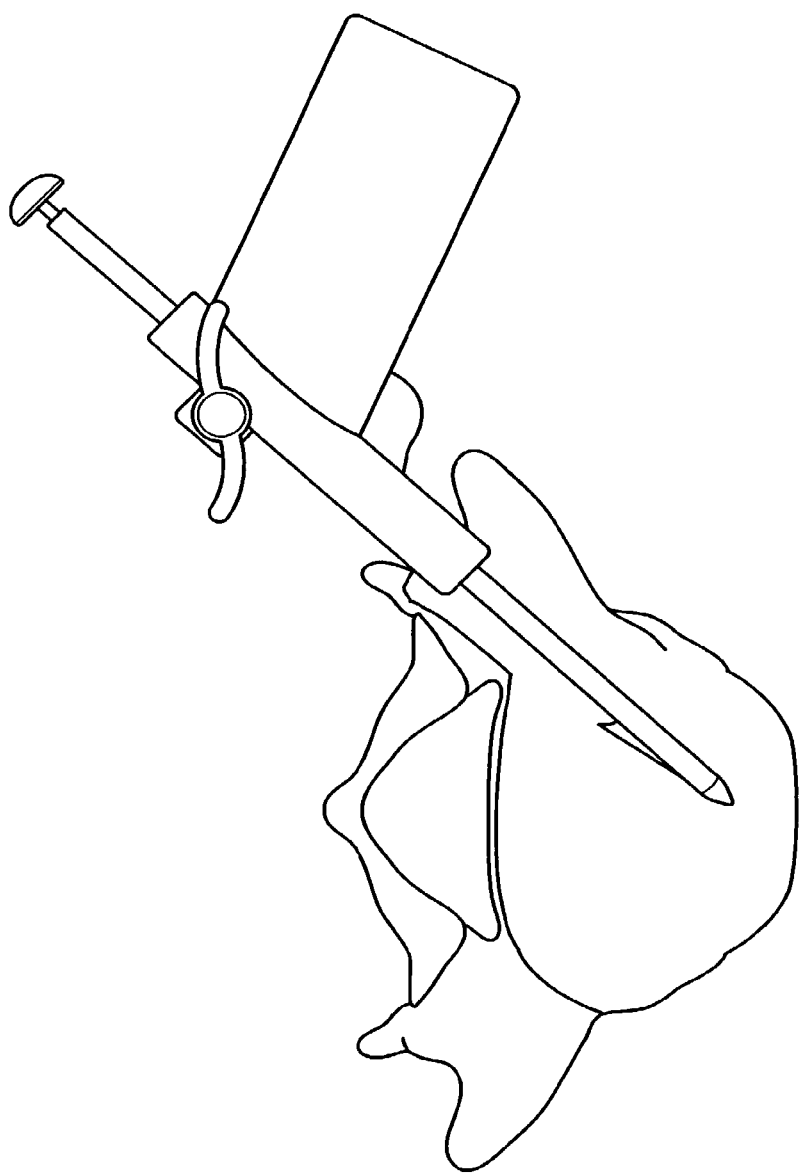

Now referring to FIG. 50C, the distal end of the pusher rod is inserted into the bore of the fixed probe and advanced until the angled portion of the pusher rod contacts the angled portion of the pivotable probe, thereby nudging the pivotable probe out of the recess. The pivotable probe is now in a partially deployed mode.

Figure 50D:
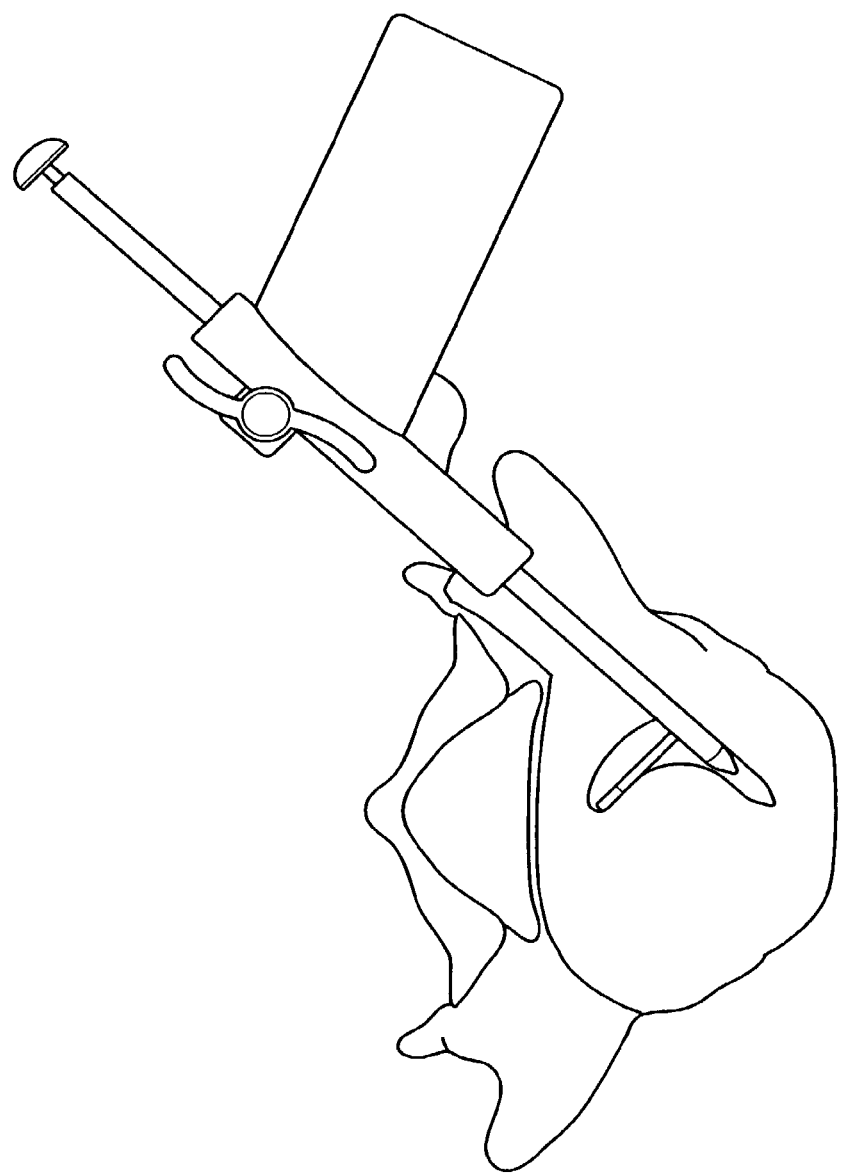
Figure 50E:
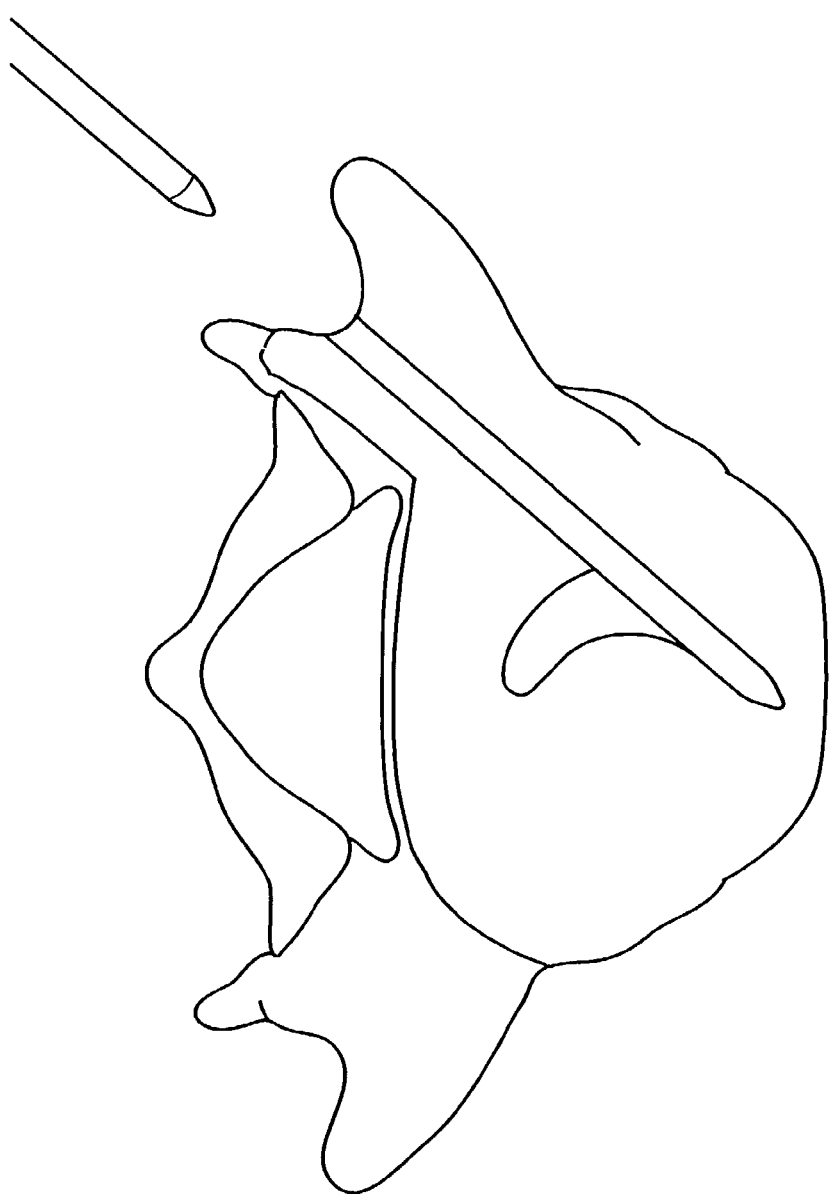

Now referring to FIG. 50D, the apparatus is slightly withdrawn from the body. As this occurs, the bone disposed between the pivotable and fixed probes prevents the pivotable probe from withdrawing along with the fixed probe, but rather forces open the pivoting means, thereby bringing the axis of the pivotable probe to a position substantially normal to the axis of the fixed probe. The pivotable probe is now in extended mode.

Next, the power supply is activated to provide a voltage between the first and second electrodes. The amount of voltage across the electrodes is sufficient to produce an electric current between the first and second electrodes. This current provides resistive heating of the tissue disposed between the electrodes in an amount sufficient to raise the temperature of the local portion of the BVN to at least 45° C., thereby denervating the BVN. In some embodiments, the temperature of the local portion of the BVN may be raised to between 40° C. and 100° C., between 40° C. and 60° C., between about 45° C. and 55° C., between 50° C. and 90° C., between 60° C. and 80° C., or in overlapping ranges thereof.

Next, the fixed probe is pushed forward to bring the pivotable probe back into the recess. Now referring to FIG. 50E, the probe is removed from the body.

Example IV

Figure 51:
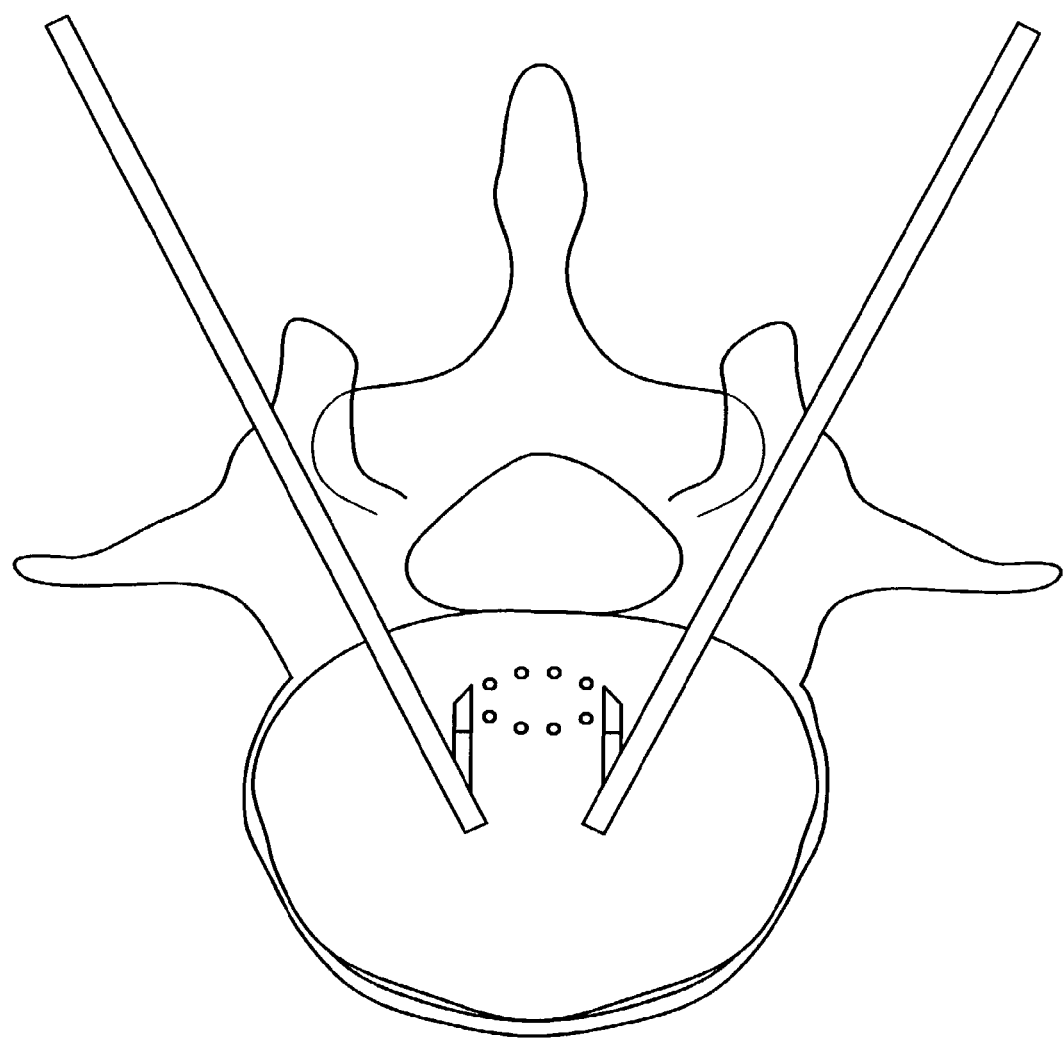
FIG. 51 presents a dual articulated needle embodiment.

Now referring to FIG. 51, there is provided a dual articulated needle embodiment wherein the articulated needles are each advanced down the pedicles of the vertebral body, and each of the pivotable probes are deployed at an angle of less than 90 degrees, so that the electrodes thereon align themselves in an essentially parallel relationship. Because the electric field produced by this embodiment is relatively even between the electrodes, the resulting total heating zone is also desirably homogeneous. Because the electrodes deploy in the central posterior portion of the vertebral body, the BVN is desirably denervated near its trunk (e.g., at or posterior to a junction or terminus of the BVN).

Example V

A pilot human clinical study was performed to determine efficacy of a minimally invasive technique involving ablation of the basivertebral nerve in providing relief to patients with chronic lower back pain.

In the present study, a radiofrequency device was used to ablate the nerves within the vertebral bone that transmit pain signals. The study involved treatment of 16 human patients with chronic (greater than 6 months) isolated lower back pain who were unresponsive to at least 3 months of non-surgical conservative care. The patients treated and observed in the study were an average of 47.6 years old and had undergone an average of 32.4 months of conservative treatment. The patients all had Oswestry Disability Index (ODI) scores greater than 30 and either pathologic changes or positive provocative discography at the targeted degenerated disc level.

In accordance with several embodiments, the intraosseous course of the basivertebral foramen for the targeted vertebral bodies was visualized and mapped using MRI imaging (e.g., anteroposterior and lateral still images). CT or other imaging techniques can also be used. In the study, treatment was performed using intraoperative fluoroscopy and a trans-pedicular approach; however, other visualization and approach techniques can be used. The treatment device used during the study was a bipolar radiofrequency probe with a curved obturator. In the study, the bipolar RF probe was inserted through a bone biopsy needle and guided to the target treatment location under fluoroscopy. The bipolar RF probe was then used to ablate the basivertebral nerve in a controlled manner. The RF energy delivered in the study had a frequency of 500 kHz, the temperature at the electrodes was 85° C., and the duration of treatment varied between 5 and 15 minutes. In accordance with several embodiments, the RF energy delivered may be between 400 and 600 kHz (e.g., 450 kHz, 500 kHz, 550 kHz), the temperature at the electrodes may be between 80° C. and 100° C. (e.g., 85° C., 90° C., 95° C.), and the duration of treatment may be between 4 and 20 minutes (e.g., 6 minutes, 8 minutes, 10 minutes, 12 minutes, 15 minutes).

In accordance with several embodiments, the treatment was limited to the L3, L4, L5 and S1 vertebrae. Two-level and three-level intraosseous ablation treatments were performed on various patients. The multiple levels treated during the study were at adjacent levels. Twelve patients were treated at the L4 and L5 levels, two patients were treated at L3 through L5 levels, and two patients were treated at the L5 and S1 levels.

Radiographs found no fractures during the follow-up period, and no remodeling of bone was observed. Thirteen of the sixteen patients reported "profound and immediate relief." The treatment procedure resulted in improved ODI scores and Visual Analogue Pain Scale (VAS) values, which were sustained at one year. ODI scores were significantly improved at six weeks, three months, six months, and twelve months. The mean decrease in ODI scores at 1 year was 31 points. VAS values decreased from a preoperative average of 61.1 to an average of 45.6 at the 1-year follow-up. No device-related serious adverse events were reported. Accordingly, in one embodiment, basivertebral nerve ablation is a safe, simple procedure that is applicable during the early stages of treatment for patients with disabling back pain.

Conditional language, for example, among others, "can," "could," "might," or "may," unless specifically stated otherwise, or otherwise understood within the context as used, is generally intended to convey that certain embodiments include, while other embodiments do not include, certain features, elements and/or steps.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein.

For purposes of this disclosure, certain aspects, advantages, and novel features of the inventions are described herein. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section. The features or elements from one embodiment of the disclosure can be employed by other embodiments of the disclosure. For example, features described in one figure may be used in conjunction with embodiments illustrated in other figures.

Although the description above contains many details, these should not be construed as limiting the scope of the invention(s) but as merely providing illustrations of some of the embodiments of this invention. Therefore, the scope of the invention(s) described herein fully encompasses other contemplated embodiments, as well as their equivalents. The scope of the invention should be viewed in light of the appended claims. References herein to an element in the singular is not intended to mean "one and only one" unless explicitly so stated, but rather "one or more."

What is claimed is:

1. A method of treating back pain, the method comprising:
  inserting a cryotherapy device within a vertebral body,
  wherein the vertebral body is a vertebral body of a lumbar vertebra or a sacral vertebra;
  applying cooling at a target treatment location within the vertebral body using the cryotherapy device,
  wherein the target treatment location comprises a portion of a basivertebral nerve,
  wherein the cooling is configured to provide localized treatment sufficient to disrupt transmission of pain signals along the portion of the basivertebral nerve,
  wherein the cooling comprises use of liquid nitrous oxide,
  wherein the cooling is configured to cool tissue of the target treatment location within the vertebral body to a temperature of between −20 and −40 degrees Celsius wherein the temperature is maintained for 5 to 20 minutes, and
  wherein the cooling is delivered in one or more freeze cycles; and
  performing diagnostic stimulation of the portion of the basivertebral nerve within the vertebral body.

2. The method of claim 1:
  wherein the vertebral body is a vertebral body of an L5 vertebra or an S1 vertebra,
  wherein the cooling is sufficient to permanently disrupt transmission of pain signals along the portion of the basivertebral nerve,
  wherein inserting the cryotherapy device within the vertebral body comprises inserting the cryotherapy device through an introducer previously inserted within the vertebral body,
  wherein the method further comprises performing imaging prior to inserting the cryotherapy device to identify the target treatment location within the vertebral body, and
  wherein the method further comprises removing the cryotherapy device from the vertebral body.

3. The method of claim 1, wherein the cooling is sufficient to permanently disrupt transmission of pain signals along the portion of the basivertebral nerve.

4. The method of claim 1, wherein the cooling is sufficient to ablate the basivertebral nerve.

5. The method of claim 1, wherein the cooling is delivered in two or more freeze cycles, and wherein the freeze cycles comprise freeze-thaw cycles.

6. A method of treating back pain, the method comprising:
  inserting a cryotherapy device within a vertebral body,
  applying cooling at a target treatment location within the vertebral body using the cryotherapy device,
  wherein the target treatment location comprises a portion of a basivertebral nerve,
  wherein the cooling is configured to provide localized treatment sufficient to disrupt transmission of pain signals along the portion of the basivertebral nerve,
  wherein the cooling is configured to cool tissue of the target treatment location within the vertebral body to a temperature of between −20 and −80 degrees Celsius, and
  wherein the cooling is delivered in two or more freeze-thaw cycles; and
  performing diagnostic stimulation of the portion of the basivertebral nerve within the vertebral body.

7. The method of claim 6:
  wherein the vertebral body is a vertebral body of an L5 vertebra or an S1 vertebra,
  wherein the cooling is sufficient to permanently disrupt transmission of pain signals along the portion of the basivertebral nerve,
  wherein inserting the cryotherapy device within the vertebral body comprises inserting the cryotherapy device through an introducer previously inserted within the vertebral body, and
  wherein the method further comprises removing the cryotherapy device from the vertebral body.

8. The method of claim 6, wherein the cooling comprises circulating fluid within one or more lumens of the cryotherapy device.

9. The method of claim 6, wherein the temperature is between −20 and −50 degrees Celsius.

10. The method of claim 6, wherein the temperature is between −20 and −40 degrees Celsius.

11. The method of claim 6, further comprising performing imaging prior to inserting the cryotherapy device to identify the target treatment location within the vertebral body.

12. The method of claim 6, wherein the cooling comprises use of liquid nitrous oxide.

13. A method of treating back pain, the method comprising:
  inserting a cryotherapy device to a location of a vertebral body,
  applying cooling to a portion of a basivertebral nerve associated with the vertebral body using the cryotherapy device,
  wherein the cooling is configured to provide localized treatment sufficient to disrupt transmission of pain signals along the portion of the basivertebral nerve,
  wherein the cooling is configured to cool the portion of the basivertebral nerve to a temperature of between −20 and −80 degrees Celsius, and
  wherein the cooling is delivered in two or more freeze-thaw cycles.

14. The method of claim 13:
  wherein the vertebral body is a vertebral body of an L5 vertebra or an S1 vertebra, wherein the cooling is sufficient to permanently disrupt transmission of pain signals along the portion of the basivertebral nerve, wherein the temperature is between −20 and −40 degrees Celsius, and wherein inserting the cryotherapy device to a location of the vertebral body comprises inserting the cryotherapy device within the vertebral body.

15. The method of claim 14, further comprising performing imaging prior to inserting the cryotherapy device to identify the location of the vertebral body.

16. The method of claim 13, further comprising performing diagnostic stimulation of the portion of the basivertebral nerve.

17. The method of claim 13, wherein the cooling comprises circulating fluid within one or more lumens of the cryotherapy device.

18. The method of claim 13, wherein the temperature is between −20 and −50 degrees Celsius.

19. The method of claim 13, wherein the temperature is between −20 and −40 degrees Celsius.

20. The method of claim 13, wherein the cooling comprises use of liquid nitrous oxide.

\* \* \* \* \*